US008217017B2

(12) United States Patent
Dobie

(10) Patent No.: US 8,217,017 B2
(45) Date of Patent: *Jul. 10, 2012

(54) MODULATION OF INSULIN LIKE GROWTH FACTOR I RECEPTOR EXPRESSION

(75) Inventor: Kenneth W. Dobie, Carlsbad, CA (US)

(73) Assignee: Antisense Therapeutics Limited, Victoria (AU)

( * ) Notice: Subject to any disclaimer, the term of this patent is extended or adjusted under 35 U.S.C. 154(b) by 110 days.

This patent is subject to a terminal disclaimer.

(21) Appl. No.: 12/342,025

(22) Filed: Dec. 22, 2008

(65) Prior Publication Data

US 2009/0286849 A1 Nov. 19, 2009

Related U.S. Application Data

(63) Continuation of application No. 10/545,354, filed as application No. PCT/AU2004/000160 on Feb. 11, 2004, now Pat. No. 7,468,356.

(30) Foreign Application Priority Data

Feb. 11, 2003 (AU) ................................ 2003900609
May 27, 2003 (AU) ................................ 2003902610

(51) Int. Cl.
*C07H 21/02* (2006.01)
*C07H 21/04* (2006.01)
*A61K 31/70* (2006.01)
*C12Q 1/68* (2006.01)

(52) U.S. Cl. ..................... 514/44 A; 536/23.1; 536/24.1; 536/24.5

(58) Field of Classification Search ........................ None
See application file for complete search history.

(56) References Cited

U.S. PATENT DOCUMENTS

| 5,801,154 | A | 9/1998 | Baracchini et al. |
| 5,998,148 | A * | 12/1999 | Bennett et al. ..................... 435/6 |
| 6,710,163 | B1 | 3/2004 | Buchardt et al. |
| 7,196,067 | B2 * | 3/2007 | Gleave et al. ............... 514/44 A |
| 7,468,356 | B2 | 12/2008 | Wraight et al. |
| 2004/0171149 | A1 | 9/2004 | Wraight et al. |
| 2009/0111767 | A1 | 4/2009 | Wraight et al. |

FOREIGN PATENT DOCUMENTS

| WO | WO-94/22486 A1 | 10/1994 |
| WO | WO-96/10401 A1 | 4/1996 |
| WO | WO-98/22579 A1 | 5/1998 |
| WO | WO-99/23259 A1 | 5/1999 |
| WO | WO-02/06345 A2 | 1/2002 |
| WO | WO-02/24717 A1 | 3/2002 |
| WO | WO-02/086105 A1 | 10/2002 |

OTHER PUBLICATIONS

*Data on ATL1101 prostate tumour suppression published in scientific journal & Australian patent granted* (Feb. 3, 2010). Antisense Therapeutics, 2 pages.

Furukawa, J. et al. (2010). "Antisense oligonucleotide targeting of insulin-like growth factor-I receptor (IGF-IR) in prostate cancer," *The Prostate* 70:206-218.

Bohula, E. A. et al. (May 2, 2003). "The Efficacy of Small Interfering RNAs Targeted to the Type 1 Insulin-Like Growth Factor Receptor (IGF1R) is Influenced by Secondary Structure in the IGF1R Transcript," *The Journal of Biological Chemistry* 278(18):15991-15997.

EMBL Accession No. BQ366237, last updated Feb. 26, 2004, located at <http://www.ebi.ac.uk/cgi-bin/emblfetch?style=html&id=BQ366237> visited on Jul. 23, 2009. (2 pages).

EMBL Accession No. M69229, last updated Nov. 14, 2006, located at <http://www.ebi.ac.uk/cgi-bin/emblfetch?style=html&id=M69229> visited on Jul. 23, 2009. (2 pages).

Fogarty, R.D. et al. (Dec. 2002). "Sequence Dependence of C5-Propynyl-dU, dC-Phosphorothioate Oligonucleotide Inhibition of the Human IGF-I receptor: mRNA, Protein, and Cell Growth," *Antisense and Nucleic Acid Drug Development* 12(6):369-377.

International Search Report mailed Apr. 29, 2004, for PCT Application No. PCT/AU2004/000160 filed Feb. 11, 2004, 7 pages.

Pietrzkowski, Z. et al. (Sep. 1992). "Roles of Insulinlike Growth Factor 1 (IGF-1) and the IGF-1 Receptor in Epidermal Growth Factor-Stimulated Growth of 3T3 Cells," *Molecular and Cellular Biology* 12(9):3883-3889.

Porcu, P. et al. (Nov. 1992). "The Growth-Stimulatory Effect of Simian Virus 40 T Antigen Requires the Interaction of Insulinlike Growth Factor 1 with its Receptor," *Molecular and Cellular Biology* 12(11):5069-5077.

Resnicoff, M. et al. (Apr. 15, 1994). "Rat Glioblastoma Cells Expressing an Antisense RNA to the Insulin-Like Growth Factor-1 (IGF-1) Receptor are Nontumorigenic and Induce Regression of Wild-Type Tumors," *Cancer Research* 54:2218-2222.

Shapiro, D. N. et al. (May 1992). "Antisense-Mediated Reduction in Insulin Like Growth Factor-I Receptor Expression Suppresses the Malignant Phenotype of a Human Rhabdomyosarcoma," *Proceedings of the Annual Meeting of the American Associate for Cancer Research*, New York, NY, USA 33:354. Supplementary Partial European Search Report mailed Dec. 12, 2006, for EP Application No. 04709958.5 filed on Feb. 11, 2004, 8 pages.

Wallenfiedman, M.A. et al. (Apr. 1996). "Effects of IGF-1R Antisense and Nonsense Oligonucleotide Administration on 9L Glioblastoma and MAT B3 Breast Cancer Tumor Growth in Fischer 344 Rats," *Proceedings of the 87th Annual Meeting of the American Association for Cancer Research*, Philadelphia, AACR, USA 37:354.

(Continued)

*Primary Examiner* — Sean McGarry
(74) *Attorney, Agent, or Firm* — Morrison & Foerster LLP

(57) ABSTRACT

The present invention provides compositions and methods for modulating the expression of growth factor gene. In particular, this invention relates to compounds, particularly oligonucleotide compounds, which, in preferred embodiments, hybridize with nucleic acid molecules encoding the Insulin Like Growth Factor I receptor (IGF-I receptor or IGF-IR) and in particular human IGF-IR. Such compounds are exemplified herein to modulate proliferation which is relevant to the treatment of proliferative and inflammatory skin disorders and cancer. It will be understood, however, that the compounds can be used for any other condition in which the IGF-IR is involved including inflammatory condition.

2 Claims, 21 Drawing Sheets

OTHER PUBLICATIONS

White, P. et al. (Jun. 2006). "C-5 Propyne-Modified Oligonucleotides Penetrate the Epidermis in Psoriatic and Not Normal Human Skin after Topical Application," *The Journal of Investigative Dermatology* 118(6):1003-1007.

White, P. J. et al. (Jun. 2000). "Antisense Inhibition of IGF Receptor Expression in HaCaT Keratinocytes: A Model for Antisense Strategies in Keratinocytes," *Antisense & Nucleic Acid Drug Development* 10(3):195-203.

Wraight, C. J. et al. (May 2000). "Reversal of Epidermal Hyperproliferation in Psoriasis by Insulin-Like Growth Factor I Receptor Antisense Oligonucleotides," *Nature Biotechnology* 18:521-526.

GenBank Accession No. NM000875, "*Homo sapiens* insulin-like growth factor 1 receptor (IGF1R), mRNA", available at http://www.ncbi.nlm.nih.gov/nuccore/NM_000875, accessed on Feb. 23, 2012, 1 page.

* cited by examiner

```
 481  gtgtgcgcgg  gccagggcgc  cgcgcgcgcg  agccccc gt  gtgtgcagc  ggcggcggcg
                                                  ↑
 541  gcgcggcgag  gctgggggctc  ttgtttacca  gcattaactc  gctgagcgga  aaaaaaagg
 601  gaaaaaaccc  gaggaggagc  gagcgcacca  ggcgaactcg  agagaggcgg  gagagcgaga
 661  gggacgccgc  cagcgagcct  gcccacggcc  ggcgtcgca  gacccctcgg  cccgctcccc
 721  ggatccccc   gcgcctcca   cgccccctcc  gcgcgggggc  agctccacgg  cgcgcctcgc
 781  ct¹cggctgtg  accttcagcg  ag¹ccggagcc  cccgcgcaga  gcaggcggcg  gcgggcgggg
 841  gccggggcgg  ggccggggcg  gggcgggcgg  ccgggcagag  ccgggcggcg  cggcgggagt
 901  gctgagcgcg  gcgcggggcg  cccgccgctt  tgtgtgtgtc  ctggatttgg  gaaggagctc
 961  gccgcggcgg  cggcgctgag  ggaggaggcg  gccgagagcg  gagccaggag  gaggaggagg
1021  agga²ggggga  gccgctcatt  catt²ttgact  ccgcgtttct  gcccctcgcc  ggcctcgcct
1081  gtgacccgga  cttcggggcg  atctgcgaa   ctgcgtcgcg  ccctccgcg   gcggaagctc
1141  gggcgtccgg  ccgcctcccg  cgcgccaggg  ccggcttgt   ttttcctcgc  ctaggcagat
1201  ttgggctttg  cccccttct   ttgcagtttt  ccccccttcc  tgcctctccg  ggtttgaaaa
1261  tggagccga   cgacgccgac  agcccgcccc  ggcgcgcctc  ggttcccga   ctccgccgag
1321  ccctgggccg  ctgctgccgg  cgctgaggcgg  ccgcgaggggg  ccgccgcccc  cgtccgcgca
1381  cccggagggc  cccggcgggcg  gccct³tcgga  gtattgtttc  cttcg³cccttt  gttttggag
1441  ggggagcgaa  gactgagttt  gagacttgtt  tcctttcatt  tccttttttt  cttcttttt
1501  cttttttttt  tttttttttt  ttttgagaa   agggaattt   catcccaaat  aaaaggaATG Code
¹ASO  175314
²ASO  175323
³ASO  175317
```

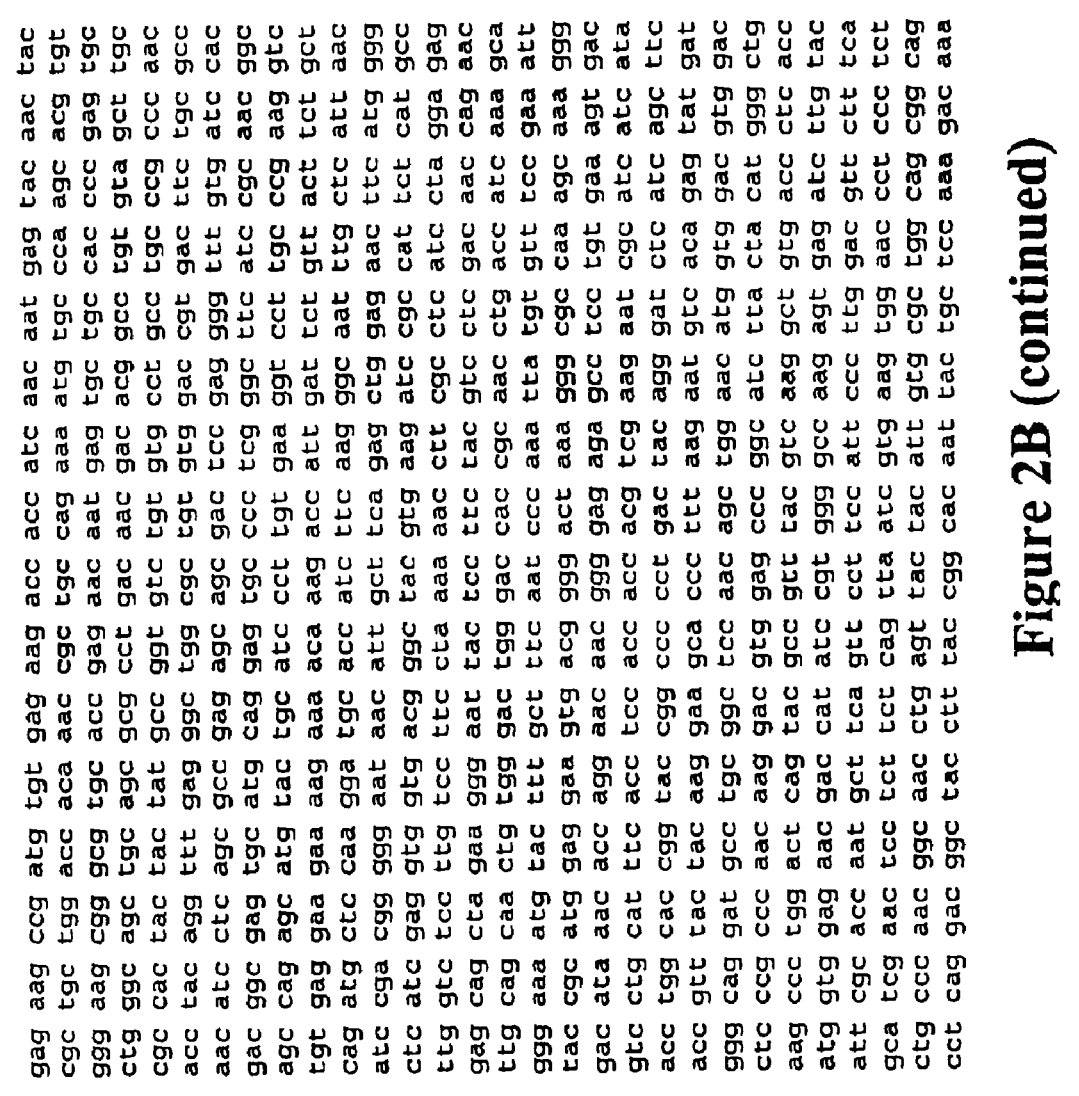

```
gag aag ccg atg tgt gag aag acc at

Figure 2B (continued)

```
aca gtc aaa atc gga gat ttt ggt atg acg cga gat atc tat gag aca
gac tat cgg aaa gga ggc aag ggg ctg ctg ccc gtg cgc tgg atg
tct cct gag tcc ctc gat ctc gga gtc tgg gtc acc act tac tcg gac gtc
tgg tcc ttc ggg gtc gtc ttg aac gag caa atc gag gcc gag cag
ccc tac cag ggc ttg tcc aag cca gac tgt cct cgc gtc ctg ttt gaa
ggc atg cgc ctg atg cgc agc tgg cag tat aac gac atg agg cct tcc ttc
ctg gag atc atc tac agc agc atc aaa gag gag atg gag cct ggc ttc cgg
gag gtc tcc ttc tac tac ctg gcc gag gag aac atg gtc gag cct ggc ttc cgg
gag ctg gac ctg gag cca cca cct ggg c

| ASO Leads | Sequence | AccNo.Pos | Region | |
|---|---|---|---|---|
| ISIS 175314 | 5'-CTCGCTGAAGGTCACAGCCG-3' | M69229.0783 | 5'UTR | [SEQ ID NO:26] |
| ISIS 175317 | 5'-CGAAGGAAACAATACTCCGA-3' | M69229.1406 | 5'UTR | [SEQ ID NO:29] |
| ISIS 175323 | 5'-AATGAATGAGCGGCTCCCCC-3' | M69229.1025 | 5'UTR | [SEQ ID NO:35] |

| Control Oligonucleotides | | |
|---|---|---|
| ISIS 129692 | 5' ACATGGGCGCGCGACTAAGT 3' | [SEQ ID NO:50] |
| ISIS 129691 | 5' ATGCATACTACGAAAGGCCG 3' | [SEQ ID NO:51] |
| ISIS 122291 | 5' TATTCCACGAACGTAGGCTG 3' | [SEQ ID NO:52] |

*2'MOE modifications are indicated by underline

Figure 3C

```
                                                                                          [SEQ ID NO:41]
   1 tttttttt tttgagaaa gggaatttca tcccaaataa aaggaatgaa gtctgctcc
  61 ggaggaggt cccgacctc gctgtggggg ctcctgtttc tctccgccgc gctctgctc
 121 tgccgacga gtggagaaat ctgcgggcca ggcatcgaca tccgcaacga ctatcagcag
 181 ctgaagcgcc tggagaactg cacgtgatc gaggctacc tccacatcct gctcatctcc
 241 aaggccgagc actaccgcag ctaccgcttc ccaagctca cggtcattac cgagtacttg
 301 ctgctgttcc gagtggctgg cctcgagagc ctcgagacc tcttcccaa cctcacggtc
 361 atccgcggct ggaaactctt ctacaactac gcctggtca tcttcgagat gaccaatctc
 421 aaggatattg ggctttacaa cctgaggaac attactcggg gggccatcag gattgagaaa
 481 aatgctgacc tctgttacct ctccactgtg gactgtccc tgatcctgga tgcggtgtcc
 541 aataactaca ttgtgggaa aaggaatgtg gggacctgtg tccaggacc
 601 atggagaga agccgatgtg tgagaagacc accatcaaca atgagtacaa ctaccgctgc
 661 tggaccacaa accgctgcca gaaaatgtgc ccaagcacgt gtgggaagcg ggcgtgcacc
 721 gagaacaatg ccccgagtgc ctgggcagct ctggccagct gcagcgcgcc tgacaagac
 781 acggcctgtg tagcttgccg ccactactac tatgccggtg tctgtgtgcc tgcctgccg
 841 cccaacacct acaggtttga gggctgcgc tgtgtgacc gtgacttctg cgccaacatc
 901 ctcagcgccg agagcagcga ctccgagggg tttgtgatcc acgacggga gtgcatgcag
 961 gagtgcccct cggctgccat cgcaacggc agcagagca tgtactgat ccctgtgaa
1021 ggtcctgcc cgaaggtctg tgagaagaa aagaaaaca agaccattga tctgttact
1081 tctgctcaga tgctccaagg atgcaagca ttcaagggca aacttgtcat taacatccga
1141 cggggaata acattgcttc agagctggag aacttcatgg ggctcatcga ggtgtgacg
1201 ggctacgtga agatccgcca ttctcatgcc ttgtctcct tgtcttcct aaaaaacctt
1261 cgcctcatcc taggagagga gcagctagaa gggaattact cctcctacgt cctgacaac
1321 cagaacttgc agcaactgtg ggactgggac caccgcaaac tgaccatcaa agcaggaaa
1381 atgtactttg ctttcaatcc caaattatgt gttttcggca tttaccgcat cggggagaga
1441 acgggggacta aagggcgcca aagcaaaggg gacataaaca ccaggaacaa cggagagaga
1501 gcctcctgtg aaagtgacgt cctgcatttc ccggcccccc gactacgcga gaatcgcatc
1561 atcataacct ggcaccgta aagcaaaggg gactacaggg atctcatcag cttcaccgtt
1621 tactacaagg aagcaccctt taagaatgtc acagagtatg atgggcagga tgcctgcggc
1681 tccaacagct ggaacatggt ggacgtggac ctcccgccca acaaggacgt ggagcccggc
1741 atcttactac atgggctgaa gcccctgact gcctacgccg cagtacgcc tttacgtcaa gctgtgacc
1801 ctcaccatgg tggagaacga ccatatccgt gggccaaga gtgagatctt gtacattcgc
```

Figure 7

```
1861  accaatgctt cagttcc tc cattccctcg gacgttcttt cagcatcgaa ctcctcttct
1921  cagttaatcg tgaagtgaa ccctccctct ctgcccaacg gcaacctgag ttactacatt
1981  gtgcgctggc agcggcagcc tcaggacggc tacctttacc ggcacaatta ctgtccaaa
2041  gacaaaatcc ccatcaggaa gtatgccgac ggcaccatcg acattgagga ggtcacagag
2101  aacccaaga ctgaggtgtg tgtggggag aaagggcctt gctgcgcctg cccaaaact
2161  gaagccgaga agcaggccga gaaggaggag gctgaatacc gcaaagtctt tgagaatttc
2221  ctgcacaact ccatcttcgt gcccagacct gaaaggaagc ggagagatgt catgcaagtg
2281  gccaacacca ccatgtccag ccgaagcagg aacaccacgg cgcagacac ctacaacatc
2341  accgacccgg aagagctgga gacagagtac ccttctttg agagcagagt ggataacaag
2401  gagagaactg tcatttctaa ccttcggcct ttcacattgt accgcatcga tatccacagc
2461  tgcaaccacg aggctgagaa gctgggctgc agcgcctcca acttcgtctt tgcaaggact
2521  atgcccgcag aaggagcaga tgacattcct gggcagtga cctggagcc aaggctgaa
2581  aactccatct tttaaagtg gccggaacct gagaatccca atggattgat tctaatgtat
2641  gaaataaaat acggatcaca agttgaggat cagcgagaat gtgtgtccag acaggaatac
2701  aggaagtatg gaggggccaa gctaaaccgg ctaaaccgg ggaactacac agcccggatt
2761  caggccacat ctctctctgg gaatgggtcg tggacagatc ctgttctt ctatgtccag
2821  gccaaaacag gatatgaaaa cttcatccat ctgatcatcg ctctgcccgt cgctgtcctg
2881  ttgatcgtgg gagggttggt gattatgctg tacgtcttcc atagaaagag aaataacagc
2941  aggctgggga atggagtgct ctgatgagtg ggagttggct gtgaaccgg agtacttcag cgctgctgat
3001  gtgtacgttc ctgatgagtg ggaggtgtg cggagaaga tcaccatgag ccggatcag cggaacttc
3061  gggcagggt cgtttgggat ggtctatgaa ggagttgcca ggagttgcca ggagttgcca caagctgcg
3121  cctgaaacca gagtggccat taaaacagtg aacgaggcg gagttcaatt gtcaccatgt ggtcgatg
3181  gagttctca acgaagcttc tgtgatgaag gagttcatca ctggtcatca tggaactgat gacacgggc
3241  ctggtgtgg tgtcccaagg ccagcaaca gtctctgagg ccagaaatgg agaataatcc agtcctagca
3301  gatctcaaaa gttatctccg gtctcagat ttgcagacgg catgcatac
3361  cctccaagcc tgagcaagat gattcagatg gccgagaga ttgcagacgg catgcatac
3421  ctcaacgcca ataagtcgt ccacagagac ctgctgccc gaattgcat ggtagccga
3481  gattccacag tcaaaatccg agattttggt atgacgcgag atatctatga gacagactat
3541  taccggaaag gagggcaaag gctgctgccc ctgtcctcg tgttcctga gtccctcaag
3601  gatggagtct tcaccactta ctcggacgtb tggtccttcg gggtcgtcct ctgggagatc
3661  gccacactgg ccgagcagcc caagcagcac ttgtccaacg agcaagtcct tcgcttcgtc
3721  atggagggcg gcttctgaa aactgtcctg acatgctgtt tgaactgatg
3781  cgcatgtgct ggcagtataa ccccaagatg aggccttct tcctggagat catcagcagc
```

Figure 7 (continued)

MODULATION OF INSULIN LIKE GROWTH FACTOR I RECEPTOR EXPRESSION

This application is a Continuation application of U.S. patent application Ser. No. 10/545,354, entitled MODULATION OF INSULIN LIKE GROWTH FACTOR I RECEPTOR EXPRESSION, filed on Aug. 11, 2005; which claims priority to PCT/AU2004/000160, entitled MODULATION OF INSULIN LIKE GROWTH FACTOR I RECEPTOR EXPRESSION, filed on Feb. 11, 2004; which claims priority to Australian application No. AU 2003902610; entitled MODULATION OF INSULIN LIKE GROWTH FACTOR I RECEPTOR EXPRESSION, filed on May 27, 2003; which claims priority to Australian application No. AU2003900609; entitled MODULATION OF INSULIN LIKE GROWTH FACTOR I RECEPTOR EXPRESSION, filed on Feb. 11, 2003; all of which are incorporated herein by reference in their entireties.

FIELD OF THE INVENTION

The present invention provides compositions and methods for modulating the expression of a growth factor receptor gene. In particular, this invention relates to compounds, particularly oligonucleotide compounds, which, in preferred embodiments, hybridize with nucleic acid molecules encoding the Insulin Like Growth Factor I receptor (IGF-I receptor or IGF-IR). Such compounds are exemplified herein to modulate proliferation which is relevant to the treatment of proliferative and inflammatory skin disorders and cancer. It will be understood, however, that the compounds can be used for any other condition in which the IGF-IR is involved including inflammatory conditions.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in any country.

Psoriasis and other similar conditions are common and often distressing proliferative and/or inflammatory skin disorders affecting or having the potential to affect a significant proportion of the population. The condition arises from over proliferation of basal keratinocytes in the epidermal layer of the skin associated with inflammation in the underlying dermis. Whilst a range of treatments have been developed, none is completely effective and free of adverse side effects. Although the underlying cause of psoriasis remains elusive, there is some consensus of opinion that the condition arises at least in part from over expression of local growth factors and their interaction with their receptors supporting keratinocyte proliferation via keratinocyte receptors which appear to be more abundant during psoriasis.

One important group of growth factors are the dermally-derived insulin-like growth factors (IGFs) which support keratinocyte proliferation. In particular, IGF-I and IGF-2 are ubiquitous polypeptides each with potent mitogenic effects on a broad range of cells. Molecules of the IGF type are also known as "progression factors" promoting "competent" cells through DNA synthesis. The IGFs act through a common receptor known as the Type I receptor or IGF-IR, which is tyrosine kinase linked. They are synthesized in mesenchymal tissues, including the dermis, and act on adjacent cells of mesodermal, endodermal or ectodermal origin. The regulation of their synthesis involves growth hormone (GH) in the liver, but is poorly defined in most tissues (Sara, *Physiological Reviews* 70: 591-614, 1990).

Particular proteins, referred to as IGF binding proteins (IGFBPs), appear to be involved in autocrine/paracrine regulation of tissue IGF availability (Rechler and Brown, *Growth Regulation* 2: 55-68, 1992). Six IGFBPs have so far been identified. The exact effects of the IGFBPs is not clear and observed effects in vitro have been inhibitory or stimulatory depending on the experimental method employed (Clemmons, *Growth Regn.* 2:80, 1992). There is some evidence, however, that certain IGFBPs are involved in targeting IGF-I to its cell surface receptor.

Skin, comprising epidermis and underlying dermis, has GH receptors on dermal fibroblasts (Oakes et al., *J. Clin. Endocrinol. Metab.* 73: 1368-1373, 1992). Fibroblasts synthesize IGF-1 as well as IGFBPs-3, -4, -5 and -6 (Camacho-Hubner et al., *J. Biol. Chem.* 267: 11949-11956, 1992) which may be involved in targeting IGF-1 to adjacent cells as well as to the overlaying epidermis. The major epidermal cell type, the keratinocyte, does not synthesize IGF-I, but possesses IGF-I receptors and is responsive to IGF-I (Neely et al., *J. Inv. Derm.* 96: 104, 1991).

In the last decade, there have been many reports of the use of antisense oligonucleotides to explore gene function and in the development of nucleic acid based drugs. Antisense oligonucleotides inhibit mRNA translation via a number of alternative ways including destruction of the target mRNA through RNaseH recruitment, or interference with RNA processing, nuclear export, folding or ribosome scanning. More recently, a better understanding of intracellular sites of action of the various antisense modalities and improvements in oligonucleotide chemistry have increased the number of reports of validated expression inhibition.

In work leading up to the present invention, the inventors focused on the use of the antisense approach to inhibit the growth of human epidermal keratinocytes, particularly in human epidermal growth disorders such as psoriasis. Psoriasis is a common and disfiguring skin condition associated with severe epidermal hyperplasia. Existing psoriasis therapies are only partially effective, however, treatments targeting the epidermis have shown promise (Jensen et al., *Br. J. Dermatol.* 139: 984-991, 1998; van de Kerkhof, *Skin Pharmacol. Appl. Skin Physiol.* 11: 2-10, 1998). One strategy is to develop antisense inhibitors of IGF-IR expression and to use these to block IGF-I-stimulated cell division and survival in the epidermis.

The IGF-IR is a tyrosine kinase linked cell surface receptor (Ullrich et al., *EMBO J.* 5: 2503-2512, 1986) that regulates cell division, transformation and apoptosis in many cell types (LeRoith et al., *Endocr. Rev.* 16: 143-163, 1995; Rubin and Baserga, *Laboratory Investigation* 73: 311-331, 1995). Human epidermal keratinocytes are highly responsive to IGF-IR activation (Ristow and Messmer, *J. Cell Physiol.* 137: 277-284, 1988; Neely et al., *J. Invest. Dermatol.* 96: 104-110, 1991; Wraight et al., *J. Invest. Dermatol.* 103: 627-631, 1994) and several studies point to an important role for IGF-1R activation in the pathogenesis of psoriasis (Krane et al., *J. Invest. Dermatol.* 96: 419-424, 1991; Krane et al., *J. Exp. Med.* 175: 1081-1090, 1992; Ristow, *Growth Regul.* 3: 129-137, 1993; Hodak et al., *J. Invest. Dermatol.* 106: 564-570, 1996; Xu et al., *J. Invest. Dermatol.* 106: 109-112, 1996; Ristow, *Dermatology* 195: 213-219, 1997; Wraight et al., *J. Invest. Dermatol.* 108: 452-456, 1997). The IGF-IR has been targeted previously by antisense approaches in fibroblasts, haemopoietic cells and glioblastoma cells to investigate its role in transformation and cell cycle progression (Pietrzkowski et al., *Mol. Cell. Biol.* 12: 3883-3889, 1992; Porcu et al., *Mol. Cell. Biol.* 12: 5069-5077, 1992; Reiss et al., *Oncogene* 7: 2243-2248, 1992; Resnicoff et al., *Cancer Res.* 54: 2218-2222, 1994).

The identification of propynylated phosphorothioate oligonucleotides have been reported which are capable of reducing IGF-IR mRNA levels when efficiently delivered to the keratinocyte nucleus (White et al., *Antisense Nucleic Acid Drug Dev.* 10: 195-203, 2000; Wraight et al., *Nat. Biotechnol.* 18: 521-526, 2000). These oligonucleotides were also effective at reducing IGF-I binding, receptor activation and cell proliferation in vitro and epidermal proliferation in vivo (Wraight et al., 2000, supra).

Propyne-modified phosphorothioate oligonucleotides were selected (Flanagan et al., *Nat. Biotechnol.* 14: 1139-1145, 1996b; Flanagan and Wagner, *Mol. Cell. Biochem.* 172: 213-225, 1997) because their increased affinity for target mRNA allows mRNA inhibition with lower concentrations (Wagner et al., 1993, supra) and shorter oligonucleotide length (Flanagan et al., *Nucleic Acids Res.* 24: 2936-2941, 1996a) than unmodified phosphorothioates, theoretically reducing the incidence of aptameric effects on target cells.

Whilst success has been demonstrated with the propyne-modified phosphorothioate oligonucleotides, alternative chemistries need to be considered to reduce toxicity, increase stability, increase specificity profile, improve penetration and/or to enhance potency and biological, chemical or physical properties. Oligonucleotides of alternative chemistries can also provide other advantages including known large scale manufacture, human clinical development knowhow, and/or known approval as drugs.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention is directed to compounds, especially nucleic acid and nucleic acid-like oligomers, which are targeted to a nucleic acid encoding a growth factor receptor and in particular Insulin Like Growth Factor I Receptor (IGF-IR), and even more particularly human IGF-IR and which modulate the expression of IGF-1R. Pharmaceutical and other compositions comprising the compounds of the invention are also provided. Further provided are methods of screening for modulators of IGF-IR gene expression and methods of modulating the expression of the IGF-IR gene in cells, tissues or animals comprising contacting said cells, tissues or animals with one or more of the compounds or compositions of the invention. Methods of treating an animal, particularly a human, suspected of having or being prone to a disease or condition associated with expression of IGF-IR or its ligand, IGF-I, are also set forth herein. Such methods comprise administering a therapeutically or prophylactically effective amount of one or more of the compounds or compositions of the invention to the person in need of treatment.

The preferred compounds of the present invention are referred to herein as antisense oligonucleotides or ASOs. The ASOs referred to in the subject specification are listed in Table 1. The ASOs are identified by an "ISIS" number as well as a SEQ ID number.

One group of particularly preferred ASOs include ISIS 175308 (SEQ ID NO:116), ISIS 175302 (SEQ ID NO:110), ISIS 175314 (SEQ ID NO:122), ISIS 175307 (SEQ ID NO:115), ISIS 175317 (SEQ ID NO:125) and ISIS 175323 (SEQ ID NO:131).

Another group of particularly preferred ASOs include ISIS 323744 (SEQ ID NO:50), ISIS 323747 (SEQ ID NO:53), ISIS 323767 (SEQ ID NO:73), ISIS 323762 (SEQ ID NO:68) and ISIS 323737 (SEQ ID NO:43).

An even more particularly preferred ASO is ISIS 175317 (SEQ ID NO:125).

TABLE 1

Summary of nucleic acid molecules

| ISIS # | REGION | TARGET SEQ ID NO | TARGET SITE | SEQUENCE/DESCRIPTION | % INHIB | SEQ ID NO |
|---|---|---|---|---|---|---|
| 323695 | 5'UTR | NM_000875.2 | 25 | CCTTTTATTTGGGATGAAAT | 50 | 1 |
| 323696 | Start Codon | NM_000875.2 | 37 | CCAGACTTCATTCCTTTTAT | 44 | 2 |
| 323697 | Coding | NM_000875.2 | 157 | TGATAGTCGTTGCGGATGTC | 73 | 3 |
| 323698 | Coding | NM_000875.2 | 162 | GCTGCTGATAGTCGTTGCGG | 72 | 4 |
| 323699 | Coding | NM_000875.2 | 167 | CTTCAGCTGCTGATAGTCGT | 74 | 5 |
| 323700 | Coding | NM_000875.2 | 196 | CCCTCGATCACCGTGCAGTT | 56 | 6 |
| 323701 | Coding | NM_000875.2 | 223 | TTGGAGATGAGCAGGATGTG | 65 | 7 |
| 323702 | Coding | NM_000875.2 | 228 | CGGCCTTGGAGATGAGCAGG | 66 | 8 |
| 323703 | Coding | NM_000875.2 | 233 | GTCCTCGGCCTTGGAGATGA | 71 | 9 |
| 323704 | Coding | NM_000875.2 | 238 | CGGTAGTCCTCGGCCTTGGA | 71 | 10 |
| 323705 | Coding | NM_000875.2 | 367 | TTGTAGAAGAGTTTCCAGCC | 52 | 11 |
| 323706 | Coding | NM_000875.2 | 396 | TGGTCATCTCGAAGATGACC | 5 | 12 |

TABLE 1-continued

Summary of nucleic acid molecules

| ISIS # | REGION | TARGET SEQ ID NO | TARGET SITE | SEQUENCE/DESCRIPTION | % INHIB | SEQ ID NO |
|---|---|---|---|---|---|---|
| 323707 | Coding | NM_000875.2 | 401 | GAGATTGGTCATCTCGAAGA | 20 | 13 |
| 323708 | Coding | NM_000875.2 | 406 | TCCTTGAGATTGGTCATCTC | 41 | 14 |
| 323709 | Coding | NM_000875.2 | 411 | CAATATCCTTGAGATTGGTC | 29 | 15 |
| 323710 | Coding | NM_000875.2 | 416 | AAGCCCAATATCCTTGAGAT | 43 | 16 |
| 323711 | Coding | NM_000875.2 | 443 | CCCCCGAGTAATGTTCCTCA | 41 | 17 |
| 323712 | Coding | NM_000875.2 | 459 | TCTCAATCCTGATGGCCCCC | 56 | 18 |
| 323713 | Coding | NM_000875.2 | 527 | GTTATTGGACACCGCATCCA | 31 | 19 |
| 323714 | Coding | NM_000875.2 | 532 | ATGTAGTTATTGGACACCGC | 64 | 20 |
| 323715 | Coding | NM_000875.2 | 537 | CCACAATGTAGTTATTGGAC | 65 | 21 |
| 323716 | Coding | NM_000875.2 | 571 | CACAGGTCCCCACATTCCTT | 42 | 22 |
| 323717 | Coding | NM_000875.2 | 576 | CTGGACACAGGTCCCCACAT | 45 | 23 |
| 323718 | Coding | NM_000875.2 | 616 | ATGGTGGTCTTCTCACACAT | 69 | 24 |
| 323719 | Coding | NM_000875.2 | 621 | TGTTGATGGTGGTCTTCTCA | 66 | 25 |
| 323720 | Coding | NM_000875.2 | 626 | CTCATTGTTGATGGTGGTCT | 81 | 26 |
| 323721 | Coding | NM_000875.2 | 632 | GTTGTACTCATTGTTGATGG | 73 | 27 |
| 323722 | Coding | NM_000875.2 | 637 | CGGTAGTTGTACTCATTGTT | 71 | 28 |
| 323723 | Coding | NM_000875.2 | 642 | AGCAGCGGTAGTTGTACTCA | 70 | 29 |
| 323724 | Coding | NM_000875.2 | 647 | GGTCCAGCAGCGGTAGTTGT | 60 | 30 |
| 323725 | Coding | NM_000875.2 | 652 | TTTGTGGTCCAGCAGCGGTA | 67 | 31 |
| 323726 | Coding | NM_000875.2 | 674 | TGGGCACATTTTCTGGCAGC | 57 | 32 |
| 323727 | Coding | NM_000875.2 | 1283 | GGAGTAATTCCCTTCTAGCT | 21 | 33 |
| 323728 | Coding | NM_000875.2 | 1324 | TCCCACAGTTGCTGCAAGTT | 73 | 34 |
| 323729 | Coding | NM_000875.2 | 1678 | ATGTTCCAGCTGTTGGAGCC | 72 | 35 |
| 323730 | Coding | NM_000875.2 | 1683 | CCACCATGTTCCAGCTGTTG | 78 | 36 |
| 323731 | Coding | NM_000875.2 | 1750 | GTCCAGGGCTTCAGCCCATG | 74 | 37 |
| 323732 | Coding | NM_000875.2 | 1786 | GTGAGGGTCACAGCCTTGAC | 59 | 38 |
| 323733 | Coding | NM_000875.2 | 1791 | CCATGGTGAGGGTCACAGCC | 78 | 39 |
| 323734 | Coding | NM_000875.2 | 1846 | TTGGTGCGAATGTACAAGAT | 61 | 40 |
| 323735 | Coding | NM_000875.2 | 2029 | ATTTTGTCTTTGGAGCAGTA | 65 | 41 |
| 323736 | Coding | NM_000875.2 | 2203 | AGGAAATTCTCAAAGACTTT | 43 | 42 |
| 323737 | Coding | NM_000875.2 | 2290 | CTGCTTCGGCTGGACATGGT | 84 | 43 |
| 323738 | Coding | NM_000875.2 | 2295 | TGTTCCTGCTTCGGCTGGAC | 76 | 44 |
| 323739 | Coding | NM_000875.2 | 2368 | CTGCTCTCAAAGAAAGGGTA | 58 | 45 |
| 323740 | Coding | NM_000875.2 | 2373 | CCACTCTGCTCTCAAAGAAA | 0 | 46 |
| 323741 | Coding | NM_000875.2 | 2378 | GTTATCCACTCTGCTCTCAA | 57 | 47 |
| 323742 | Coding | NM_000875.2 | 2383 | TCCTTGTTATCCACTCTGCT | 58 | 48 |
| 323743 | Coding | NM_000875.2 | 2446 | TTGCAGCTGTGGATATCGAT | 53 | 49 |

TABLE 1-continued

Summary of nucleic acid molecules

| ISIS # | REGION | TARGET SEQ ID NO | TARGET SITE | SEQUENCE/DESCRIPTION | % INHIB | SEQ ID NO |
|---|---|---|---|---|---|---|
| 323744 | Coding | NM_000875.2 | 2451 | CGTGGTTGCAGCTGTGGATA | 85 | 50 |
| 323745 | Coding | NM_000875.2 | 2456 | AGCCTCGTGGTTGCAGCTGT | 75 | 51 |
| 323746 | Coding | NM_000875.2 | 2461 | TTCTCAGCCTCGTGGTTGCA | 62 | 52 |
| 323747 | Coding | NM_000875.2 | 2466 | CCAGCTTCTCAGCCTCGTGG | 85 | 53 |
| 323748 | Coding | NM_000875.2 | 2471 | GCAGCCCAGCTTCTCAGCCT | 77 | 54 |
| 323749 | Coding | NM_000875.2 | 2476 | GCGCTGCAGCCCAGCTTCTC | 71 | 55 |
| 323750 | Coding | NM_000875.2 | 2578 | TTTAAAAAGATGGAGTTTTC | 8 | 56 |
| 323751 | Coding | NM_000875.2 | 2583 | GCCACTTTAAAAAGATGGAG | 77 | 57 |
| 323752 | Coding | NM_000875.2 | 2677 | TCCTGTCTGGACACACATTC | 66 | 58 |
| 323753 | Coding | NM_000875.2 | 2791 | AAGAACACAGGATCTGTCCA | 38 | 59 |
| 323754 | Coding | NM_000875.2 | 2796 | CATAGAAGAACACAGGATCT | 33 | 60 |
| 323755 | Coding | NM_000875.2 | 2992 | GGAACGTACACATCAGCAGC | 36 | 61 |
| 323756 | Coding | NM_000875.2 | 3076 | ACTCCTTCATAGACCATCCC | 26 | 62 |
| 323757 | Coding | NM_000875.2 | 3301 | CGGAGATAACTTTTGAGATC | 35 | 63 |
| 323758 | Coding | NM_000875.2 | 3306 | GAGACCGGAGATAACTTTTG | 29 | 64 |
| 323759 | Coding | NM_000875.2 | 3478 | ATTTTGACTGTGAAATCTTC | 13 | 65 |
| 323760 | Coding | NM_000875.2 | 3643 | GCGATCTCCCAGAGGACGAC | 72 | 66 |
| 323761 | Coding | NM_000875.2 | 3870 | TGTAGTAGAAGGAGACCTCC | 26 | 67 |
| 323762 | Coding | NM_000875.2 | 4000 | GCCTTGTGTCCTGAGTGTCT | 84 | 68 |
| 323763 | Stop Codon | NM_000875.2 | 4139 | ATCCAAGGATCAGCAGGTCG | 69 | 69 |
| 323764 | 3'UTR | NM_000875.2 | 4329 | GCTGCTTGCATATTGAAAAA | 77 | 70 |
| 323765 | 3'UTR | NM_000875.2 | 4334 | AAAAGCTGCTTGCATATTG | 74 | 71 |
| 323766 | 3'UTR | NM_000875.2 | 4366 | GCCCATGTCAGTTAAGGGTT | 69 | 72 |
| 323767 | 3'UTR | NM_000875.2 | 4822 | CCAGCGTGTCTCTCAAATGG | 84 | 73 |
| 323768 | Intron | NT_035325.2 | 62268 | GGAGTTTAAAGGACAGTGCC | 59 | 74 |
| 323769 | Exon: Intron Junction | NT_035325.2 | 280527 | CATCACTGACCTCTTTCTAT | 0 | 75 |
| IG-IR 5' (M69229) | | | | 5' untranslated sequence of human IGF-IR | | 76 |
| IGF-IR (NM0008 75) | | | | Nucleotide sequence encoding human IGF-IR | | 77 |
| DT1064 | | | | Nucleotide sequence encoding IGF-IR C5 propyne lead CAC AGU UGC UGC AAG DT1064$_2$ | | 78 |
| 13920 | | | | antisense oligonucleotide control to human H-ras | | 79 |
| 18078 | | | | antisense oligonucleotide control to human JNK | | 80 |
| 15770 | | | | antisense oligonucleotide control to mouse and rat c-raf | | 81 |

TABLE 1-continued

Summary of nucleic acid molecules

| ISIS # | REGION | TARGET SEQ ID NO | TARGET SITE | SEQUENCE/DESCRIPTION | % INHIB | SEQ ID NO |
|---|---|---|---|---|---|---|
| 161212 | | | | PCR primer to hIGF-RI | | 82 |
| 161214 | | | | PCR primer to hIGF-RI | | 83 |
| 161215 | | | | PCR primer t hIGF-RI | | 84 |
| 129692 | | | | Negative control ASO | | 85 |
| 121691 | | | | Negative control ASO | | 86 |
| 122291 | | | | Negative control ASO | | 87 |
| R451 | | | | ASO used for localization study | | 88 |
| 251741 | | | | ASO used for localization study | | 89 |
| 13920 | | | | ASO used for localization study | | 90 |
| 147979 | | | | ASO used for localization study | | 91 |
| | | | | exemplified sense strand | | 92 |
| | | | | exemplified antisense strand | | 93 |
| | | | | PCR primer for hGAPDH | | 94 |
| | | | | PCR primer for hGAPDH | | 95 |
| | | | | PCR probe to hGAPDH | | 96 |
| | IGF-IR | | | Nucleotide Sequence of IGF-IR mRNA with 3' and 5' untranslated regions | | 97 |
| | | | | 391 amino acid sequence of IGF-IR protein | | 98 |
| 298948 | | | | Negative Control ASO | | 99 |
| 175292 | 5'UTR | SEQ ID NO: 97 | 930 | agtctcaaaactcagtcttcg | 78 | 100 |
| 175293 | 5'UTR | SEQ ID NO: 97 | 42 | gttaatgctggtaaacaaga | 40 | 101 |
| 175294 | 5'UTR | SEQ ID NO: 97 | 558 | gaagtccgggtcacaggcga | 77 | 102 |
| 175295 | 5'UTR | SEQ ID NO: 97 | 29 | aacaagagccccagcctcgc | 76 | 103 |
| 175296 | 5'UTR | SEQ ID NO: 97 | 38 | atgctggtaaacaagagccc | 57 | 104 |
| 175297 | 5'UTR | SEQ ID NO: 97 | 37 | tgctggtaaacaagagcccc | 61 | 105 |
| 175298 | 5'UTR | SEQ ID NO: 97 | 516 | ggagtcaaaatgaatgagcg | 74 | 106 |
| 175299 | 5'UTR | SEQ ID NO: 97 | 665 | aatctgcctaggcgaggaaa | 78 | 107 |
| 175300 | 5'UTR | SEQ ID NO: 97 | 36 | gctggtaaacaagagcccca | 54 | 108 |
| 175301 | 5'UTR | SEQ ID NO: 97 | 671 | agcccaaatctgcctaggcg | 77 | 109 |
| 175302 | 5'UTR | SEQ ID NO: 97 | 730 | cctccatttcaaacccgga | 93 | 110 |
| 175303 | 5'UTR | SEQ ID NO: 97 | 260 | gaaggtcacagccgaggcga | 82 | 111 |
| 175304 | 5'UTR | SEQ ID NO: 97 | 265 | tcgctgaaggtcacagccga | 76 | 112 |
| 175305 | 5'UTR | SEQ ID NO: 97 | 410 | atccaggacacacacaaagc | 81 | 113 |
| 175306 | 5'UTR | SEQ ID NO: 97 | 557 | aagtccgggtcacaggcgag | 54 | 114 |
| 175307 | 5'UTR | SEQ ID NO: 97 | 931 | aagtctcaaaactcagtcttc | 86 | 115 |
| 175308 | 5'UTR | SEQ ID NO: 97 | 738 | gtcgtcggcctccattttca | 94 | 116 |
| 175309 | 5'UTR | SEQ ID NO: 97 | 526 | gcagaaacgcggagtcaaaa | 72 | 117 |

TABLE 1-continued

Summary of nucleic acid molecules

| ISIS # | REGION | TARGET SEQ ID NO | TARGET SITE | SEQUENCE/DESCRIPTION | % INHIB | SEQ ID NO |
|---|---|---|---|---|---|---|
| 175310 | 5'UTR | SEQ ID NO: 97 | 429 | gcggcgagctccttcccaaa | 76 | 118 |
| 175311 | 5'UTR | SEQ ID NO: 97 | 40 | taatgctggtaaacaagagc | 53 | 119 |
| 175312 | 5'UTR | SEQ ID NO: 97 | 723 | tttcaaacccggagaggcag | 31 | 120 |
| 175313 | 5'UTR | SEQ ID NO: 97 | 657 | taggcgaggaaaaacaagcc | 62 | 121 |
| 175314 | 5'UTR | SEQ ID NO: 97 | 266 | ctcgctgaaggtcacagccg | 87 | 122 |
| 175315 | 5'UTR | SEQ ID NO: 97 | 798 | gcagcggcccagggctcggc | 75 | 123 |
| 175316 | 5'UTR | SEQ ID NO: 97 | 267 | gctcgctgaaggtcacagcc | 82 | 124 |
| 175317 | 5'UTR | SEQ ID NO: 97 | 889 | cgaaggaaacaatactccga | 84 | 125 |
| 175318 | 5'UTR | SEQ ID NO: 97 | 523 | gaaacgcggagtcaaaatga | 68 | 126 |
| 175319 | 5'UTR | SEQ ID NO: 97 | 884 | gaaacaatactccgaagggc | 63 | 127 |
| 175320 | 5'UTR | SEQ ID NO: 97 | 414 | ccaaatccaggacacacaca | 64 | 128 |
| 175321 | 5'UTR | SEQ ID NO: 97 | 734 | tcggcctccattttcaaacc | 78 | 129 |
| 175322 | 5'UTR | SEQ ID NO: 97 | 554 | tccgggtcacaggcgaggcc | 67 | 130 |
| 175323 | 5'UTR | SEQ ID NO: 97 | 508 | aatgaatgagcggctccccc | 82 | 131 |
| 175324 | 5'UTR | SEQ ID NO: 97 | 261 | tgaaggtcacagccgaggcg | 57 | 132 |
| 175325 | 5'UTR | SEQ ID NO: 97 | 259 | aaggtcacagccgaggcgag | 55 | 133 |
| 175326 | 5'UTR | SEQ ID NO: 97 | 415 | cccaaatccaggacacacac | 74 | 134 |
| 175327 | 5'UTR | SEQ ID NO: 97 | 933 | acaagtctcaaactcagtct | 61 | 135 |
| 175328 | 5'UTR | SEQ ID NO: 97 | 33 | ggtaaacaagagccccagcc | 64 | 136 |
| 90444 | | | 930 | cgaagactgagtttgagact | | 137 |
| 90446 | | | 558 | tcgcctgtgacccggacttc | | 138 |
| 90447 | | | 29 | gcgaggctggggctcttgtt | | 139 |
| 90448 | | | 38 | gggctcttgtttaccagcat | | 140 |
| 90449 | | | 37 | ggggctcttgtttaccagca | | 141 |
| 90450 | | | 516 | cgctcattcatttgactcc | | 142 |
| 90451 | | | 665 | tttcctcgcctaggcagatt | | 143 |
| 90452 | | | 36 | tggggctcttgtttaccagc | | 144 |
| 90453 | | | 671 | cgcctaggcagatttgggct | | 145 |
| 90454 | | | 730 | tccgggtttgaaaatggagg | | 146 |
| 90455 | | | 260 | tcgcctcggctgtgaccttc | | 147 |
| 90456 | | | 265 | tcggctgtgaccttcagcga | | 148 |
| 90457 | | | 410 | gctttgtgtgtgtcctggat | | 149 |
| 90458 | | | 557 | ctcgcctgtgacccggactt | | 150 |
| 90459 | | | 931 | gaagactgagtttgagactt | | 151 |
| 90460 | | | 738 | tgaaaatggaggccgacgac | | 152 |
| 90461 | | | 526 | ttttgactccgcgtttctgc | | 153 |
| 90462 | | | 429 | tttgggaaggagctcgccgc | | 154 |

TABLE 1-continued

Summary of nucleic acid molecules

| ISIS # | REGION | TARGET SEQ ID NO | TARGET SITE | SEQUENCE/DESCRIPTION | % INHIB | SEQ ID NO |
|---|---|---|---|---|---|---|
| 90463 | | | 40 | gctcttgtttaccagcatta | | 155 |
| 90465 | | | 657 | ggcttgtttttcctcgccta | | 156 |
| 90466 | | | 266 | cggctgtgaccttcagcgag | | 157 |
| 90467 | | | 798 | gccgagccctgggccgctgc | | 158 |
| 90468 | | | 267 | ggctgtgaccttcagcgagc | | 159 |
| 90469 | | | 889 | tcggagtattgtttccttcg | | 160 |
| 90470 | | | 523 | tcattttgactccgcgtttc | | 161 |
| 90471 | | | 884 | gcccttcggagtattgtttc | | 162 |
| 90472 | | | 414 | tgtgtgtgtcctggatttgg | | 163 |
| 90473 | | | 734 | ggtttgaaaatggaggccga | | 164 |
| 90474 | | | 554 | ggcctcgcctgtgacccgga | | 165 |
| 90475 | | | 508 | gggggagccgctcattcatt | | 166 |
| 90476 | | | 261 | cgcctcggctgtgaccttca | | 167 |
| 90477 | | | 259 | ctcgcctcggctgtgacctt | | 168 |
| 90478 | | | 415 | gtgtgtgtcctggatttggg | | 169 |
| 90479 | | | 933 | agactgagtttgagacttgt | | 170 |
| 90480 | | | 33 | ggctggggctcttgtttacc | | 171 |

[1]ASO, antisense oligonucleotide
[2]All C's and U's are C5 propynated

BRIEF DESCRIPTION OF THE FIGURES

FIG. 2 is a representation of (A) the nucleotide sequence of the 5' untranslated region of the IGF-IR gene (SEQ ID NO: 76) showing the location of targets for ISIS 175314 (SEQ ID NO: 122), ISIS 175317 SEQ ID NO: 125) and ISIS 175323 (SEQ ID NO: 131).

Figure 1:
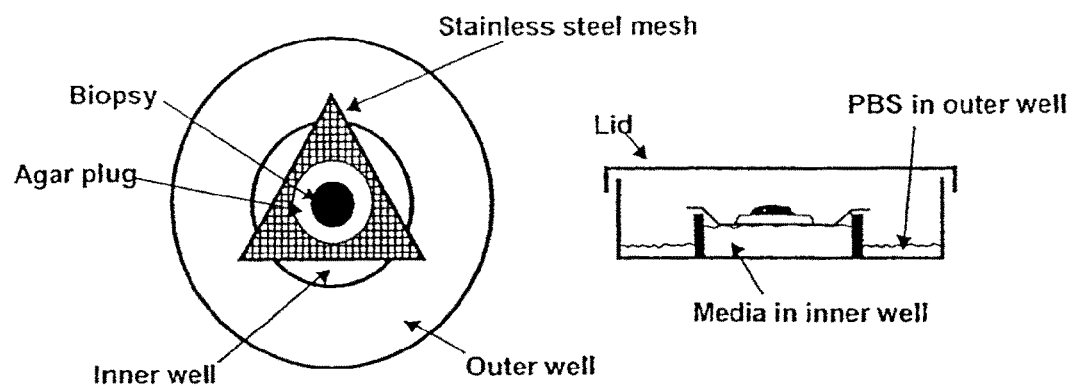
FIG. 1 is a diagrammatic representation of a skin biopsy maintained ex vivo.

| FEATURES | Location/Qualifiers |
|---|---|
| source | 1..4989 |
| | /organism="*Homo sapiens*" |
| | /db_xref="taxon:9606" |
| | /chromosome="15" |
| | /map="15q25-q26" |
| | /clone="(lambda)IGF-1-R.85, (lambda)IGF-1-R.76" |
| | /tissue_type="placenta" |
| | /clone_lib="(lamda)gt10" |
| gene | 1..4989 |
| | /gene="IGF1R" |
| | /note="synonym: JTK13" |
| | /db_xref="LocusID:3480" |
| | /db_xref="MIM:147370" |
| CDS | 46..4149 |
| | /gene="IGF1R" |
| | /EC_number="2.7.1.112" |
| | /codon_start=1 |
| | /product="insulin-like growth factor 1 receptor precursor" |
| | /protein_id="NP_000866.1" |
| | /db_xref="GI:4557665" |
| | /db_xref="LocusID:3480" |
| | /db_xref="MIM:147370" |

-continued

| FEATURES | Location/Qualifiers |
|---|---|
| sig_peptide | 46..135<br>/gene="IGF1R" |
| mat_peptide | 136..2265<br>/gene="IGF1R"<br>/product="insulin-like growth factor 1 receptor alpha chain" |
| misc_feature | 196..531<br>/gene="IGF1R"<br>/note="Recep_L_domain; Region: Receptor L domain. The L domains from these receptors make up the bilobal ligand binding site. Each L domain consists of a single-stranded right hand beta-helix. This Pfam entry is missing the first 50 amino acid residues of the domain"<br>/db_xref="CDD:pfam01030" |
| misc_feature | 568..1044<br>/gene="IGF1R"<br>/note="Furin-like; Region: Furin-like Cysteine rich region"<br>/db_xref="CDD:pfam00757" |
| misc_feature | 694..1041<br>/gene="IGF1R"<br>/note="VSP; Region: *Giardia* variant-specific surface protein"<br>/db_xref="CDD:pfam03302" |
| misc_feature | 724..855<br>/gene="IGF1R"<br>/note="FU; Region: Furin-like repeats"<br>/db_xref="CDD:smart00261" |
| misc_feature | 1168..1479<br>/gene="IGF1R"<br>/note="Recep_L_domain; Region: Receptor L domain. The L domains from these receptors make up the bilobal ligand binding site. Each L domain consists of a single-stranded right hand beta-helix. This Pfam entry is missing the first 50 amino acid residues of the domain"<br>/db_xref="CDD:pfam01030" |
| misc_feature | 1519..1800<br>/gene="IGF1R"<br>/note="FN3; Region: Fibronectin type 3 domain"<br>/db_xref="CDD:smart00060" |
| mat_peptide | 2266..4146<br>/gene="IGF1R"<br>/product="insulin-like growth factor 1 receptor beta chain" |
| misc_feature | 2542..2787<br>/gene="IGF1R"<br>/note="FN3; Region: Fibronectin type 3 domain"<br>/db_xref="CDD:smart00060" |
| misc_feature | 2548..2796<br>/gene="IGF1R"<br>/note="fn3; Region: Fibronectin type III domain"<br>/db_xref="CDD:pfam00041" |
| misc_feature | 2836..2910<br>/gene="IGF1R"<br>/note="transmembrane region (AA 906 - 929); transmembrane-region site" |
| misc_feature | 3040..3843<br>/gene="IGF1R"<br>/note="pkinase; Region: Protein kinase domain"<br>/db_xref="CDD:pfam00069" |
| misc_feature | 3040..3843<br>/gene="IGF1R"<br>/note="TyrKc; Region: Tyrosine kinase, catalytic domain"<br>/db_xref="CDD:smart00219" |
| misc_feature | 3052..3837<br>/gene="IGF1R"<br>/note="S_TKc; Region: erine/Threonine protein kinases, catalytic domain"<br>/db_xref="CDD:smart00220" |
| misc_feature | 122..2251<br>/gene="IGF1R"<br>/note="alpha-subunit (AA 1 - 710)" |
| misc_feature | 182..190<br>/gene="IGF1R"<br>/note="pot.N-linked glycosylation site (AA 21 - 23)" |
| misc_feature | 335..343<br>/gene="IGF1R"<br>/note="pot.N-linked glycostlation site (AA 72 - 74)" |

-continued

| FEATURES | Location/Qualifiers |
|---|---|
| misc_feature | 434..442<br>/gene="IGF1R"<br>/note="pot.N-linked glycostlation site (AA 105 - 107)" |
| misc_feature | 761..769<br>/gene="IGF1R"<br>/note="pot.N-linked glycostlation site (AA 214 - 216)" |
| variation | 948<br>/gene="IGF1R"<br>/allele="C"<br>/allele="A"<br>/db_xref="dbSNP:2229764" |
| misc_feature | 971..979<br>/gene="IGF1R"<br>/note="pot.N-linked glycostlation site (AA 284 - 286)" |
| misc_feature | 1280..1288<br>/gene="IGF1R"<br>/note="pot.N-linked glycostlation site (AA 387 - 389)" |
| misc_feature | 1343..1351<br>/gene="IGF1R"<br>/note="pot.N-linked glycosylation site (AA 408 - 410)" |
| misc_feature | 1631..1639<br>/gene="IGF1R"<br>/note="pot.N-linked glycostlation site (AA 504 - 506)" |
| variation | 1731<br>/gene="IGF1R"<br>/allele="G"<br>/allele="A"<br>/db_xref="dbSNP:2228531" |
| misc_feature | 1850..1858<br>/gene="IGF1R"<br>/note="pot.N-linked glycosylation site (AA 577 - 579)" |
| misc_feature | 1895..1903<br>/gene="IGF1R"<br>/note="pot.N-linked glycosylation site (AA 592 - 594)" |
| misc_feature | 1949..1957<br>/gene="IGF1R"<br>/note="pot.N-linked glycosylation site (AA 610 - 612)" |
| misc_feature | 2240..2251<br>/gene="IGF1R"<br>/note="putative proreceptor processing site (AA 707 - 710)" |
| misc_feature | 2252..4132<br>/gene="IGF1R"<br>/note="beta-subunit (AA 711 - 1337)" |
| misc_feature | 2270..2278<br>/gene="IGF1R"<br>/note="pot.N-linked glycosylation site (AA 717 - 719]" |
| misc_feature | 2297..2305<br>/gene="IGF1R"<br>/note="pot.N-linked glycosylation site (AA 726 - 728)" |
| misc_feature | 2321..2329<br>/gene="IGF1R"<br>/note="pot.N-linked glycosylation site (AA 734 - 736)" |
| variation | 2343<br>/gene="IGF1R"<br>/allele="T"<br>/allele="C"<br>/db_xref="dbSNP:3743262" |
| misc_feature | 2729..2737<br>/gene="IGF1R"<br>/note="pot.N-linked glycosylation site (AA 870 - 872)" |
| misc_feature | 2768..2776<br>/gene="IGF1R"<br>/note="pot.N-linked glycosylation site (AA 883 - 885)" |
| misc_feature | 2918..2926<br>/gene="IGF1R"<br>/note="pot.N-linked glycosylation site (AA 933 - 935)" |
| misc_feature | 3047..3049<br>/gene="IGF1R"<br>/note="pot.ATP binding site (AA 976)" |
| misc_feature | 3053..3055<br>/gene="IGF1R"<br>/note="pot.ATP binding site (AA 978)" |
| misc_feature | 3062..3064<br>/gene="IGF1R"<br>/note="pot.ATP binding site (AA 981)" |

| FEATURES | Location/Qualifiers |
|---|---|
| misc_feature | 3128..3130<br>/gene="IGF1R"<br>/note="pot.ATP binding site (AA 1003)" |
| variation | 3174<br>/gene="IGF1R"<br>/allele="G"<br>/allele="A"<br>/db_xref="dbSNP:2229765" |
| variation | complement(4205)<br>/allele="G"<br>/allele="C"<br>/db xref="dbSNP:3825954" |
| variation | 4267<br>/gene="IGF1R"<br>/allele="T"<br>/allele="A"<br>/db_xref="dbSNP:1065304" |
| variation | 4268<br>/gene="IGF1R"<br>/allele="T"<br>/allele="A"<br>/db_xref="dbSNP:1065305" |
| variation | complement(4567)<br>/allele="AG"<br>/allele="-"<br>/db_xref="dbSNP:3833015" |
| BASE COUNT<br>ORIGIN | 1216 a 1371 c 1320 g 1082 t |

(B) Nucleotide sequence of IGR-IR and corresponding amino acid sequence with 3' and 5' untranslated regions (NM000).

Figure 3A:
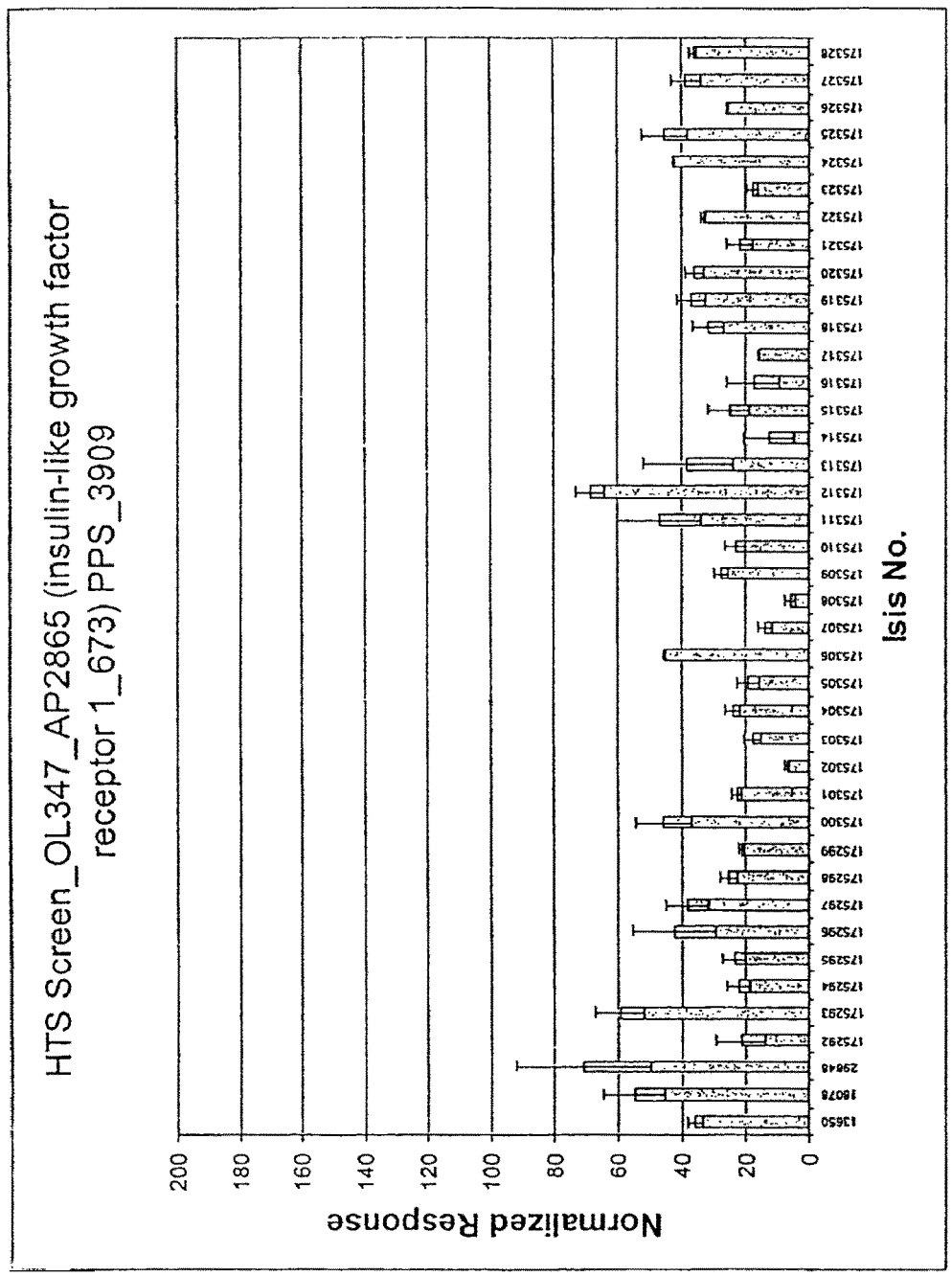
Figure 3B:
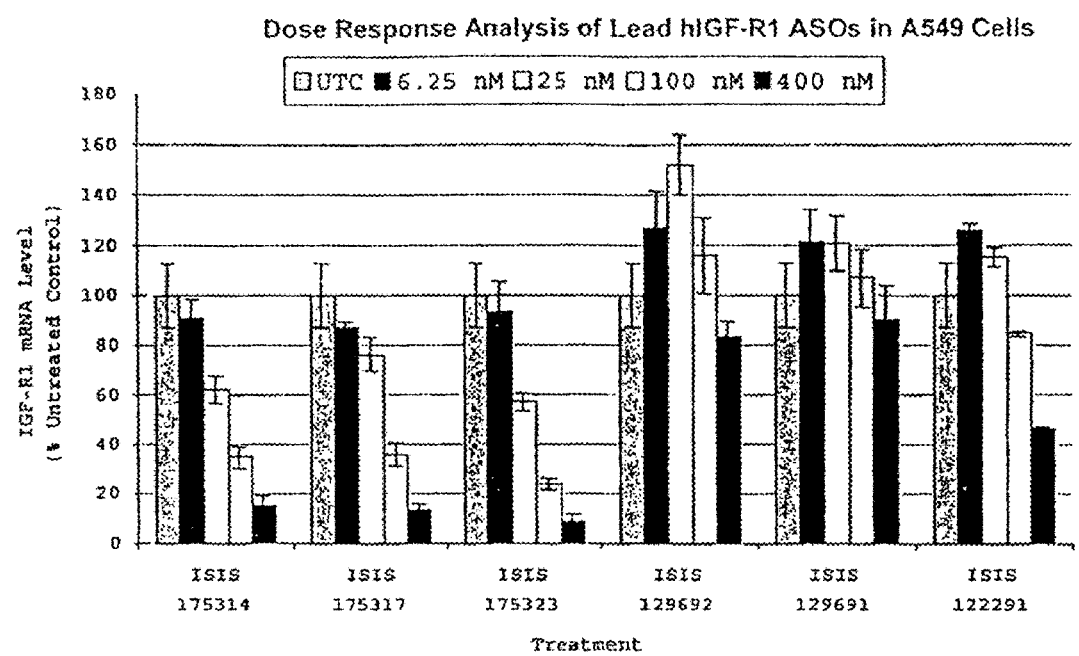

FIG. 3 is a graphical representation showing (A) the effect of lead IGF-IR ASOs ISIS 175292 through 175328 on IGF-IR mRNA in A549 cells relative to negative controls ISIS 13650, ISIS 18078 and ISIS 29848. (B) the effect of lead IGF-IR ASOs ISIS 175314, ISIS 175317 and ISIS 175323 on IGF-IR mRNA on A459 cells For (A) & (B), A459 cells were transfected with Lipofectin complexed with antisense and control oligonucleotides at a ratio of 2 lipid:1 oligonucleotide. Total cellular RNA was isolated 16-20 h later in an automated process (e.g. Qiagen Inc., Valencia, Calif., USA). The histogram represents triplicate measurements from a single experiment, showing mean IGF-IR mRNA levels as a % of the levels in untreated control±SD, (C) nucleotide sequences of ASO compounds, control oligonucleotides and primer/probe oligonucleotides.

FIG. 4 is a graphical representation showing the effect of DT1064 (SEQ ID NO:43) and lead IGF-IR ASOs (ISIS 175314 (SEQ ID NO:27), ISIS 175317 (SEQ ID NO:30) and ISIS 175323 (SEQ ID NO:36)) on IGF-IR mRNA levels in HaCaT keratinocytes. 85-90% confluent HaCaT cells were treated with GSV (2 μg/ml), with or without antisense and control oligonucleotides (6.25, 25, 100 or 400 nM). Cells were transfected once (18 h before harvest; A) or twice (at 24 and 48 h before harvest; B). Total RNA was recovered and reverse transcribed before being assayed in duplicate by real-time PCR. IGF-IR mRNA was normalized against 18S and expressed as a % of levels in the GSV-treated control cells. Results represent mean±SEM from duplicate wells of two separate experiments. UT=untreated cells, GSV=cells treated with GSV only.

FIG. 5 is a photographic and graphical representation showing the effect of DT1064 (SEQ ID NO:43) and lead IGF-IR ASOs (ISIS 175314 (SEQ ID NO:27), ISIS 175317 (SEQ ID NO:30) and ISIS 175323 (SEQ ID NO:36)) on IGF-IR protein in HaCaT keratinocytes. 85-90% confluent HaCaT cells were transfected every 24 h for 3 days. Cell lysates were harvested and equal amounts of protein (either 25 or 30 μg) from each sample were resolved by 7% w/v SDS-PAGE. Protein was transblotted to PVDF membrane and probed with anti-rabbit IgG recognizing the IGF-IR β subunit. (A) A representative immunoblot (Western 3) showing the intensity of the IGF-IR signal. Samples were run on 4 gels; the GSV-treated and untreated from each gel is shown alongside the samples run on the same gel. (B) Quantitation of IGF-IR protein band intensity expressed as a % of levels in the GSV-treated control. The histogram shows the mean±SEM for data from three separate experiments in which treatments were assessed in duplicate. A one-way ANOVA was performed followed by pair-wise comparisons by Dunnett's test: *P<0.05, ΔP<0.001 versus GSV-treated cells. UT=untreated cells, GSV=cells treated with GSV only.

Figure 6:
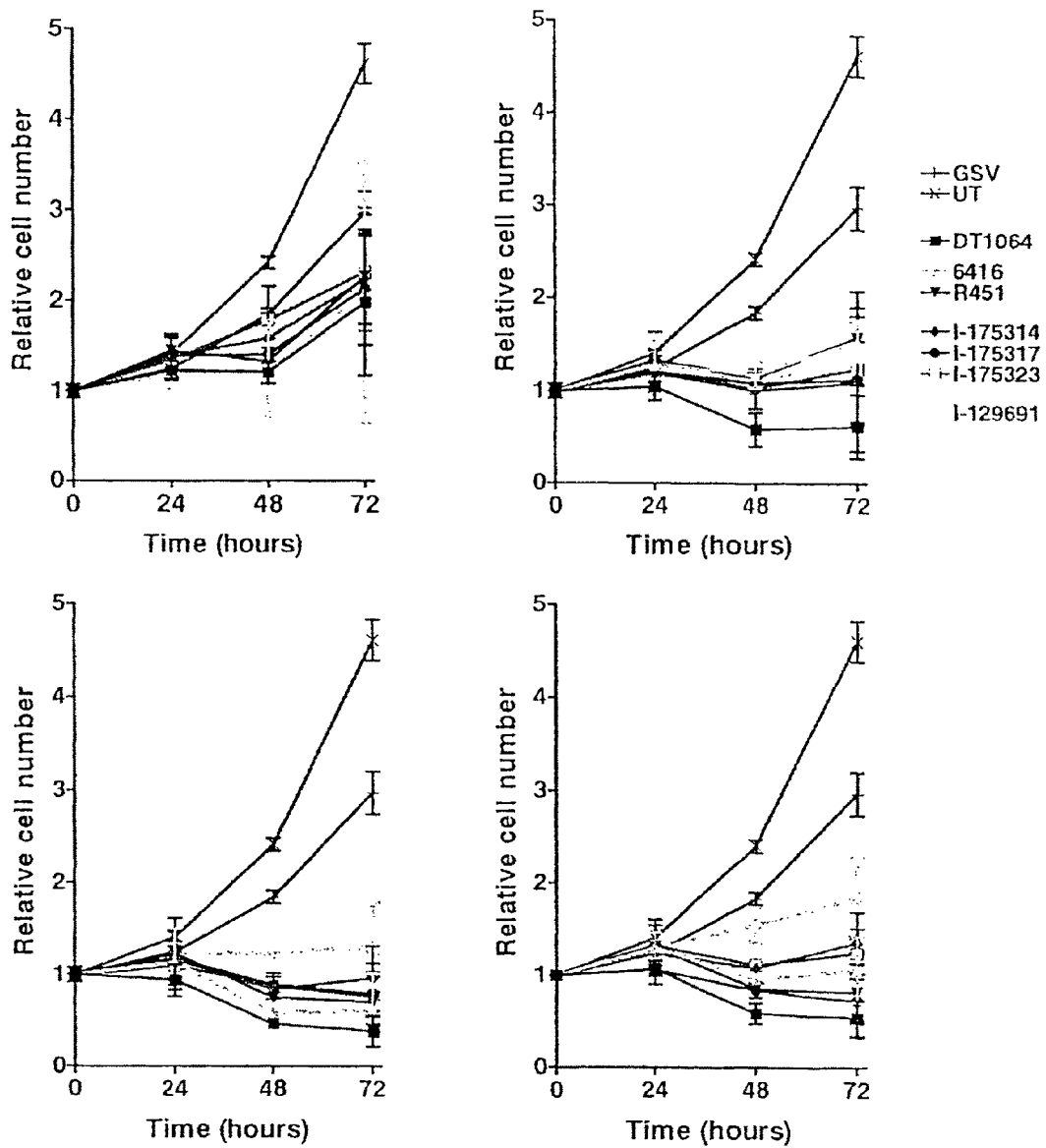

FIG. 6 is a graphical representation showing the effect of DT1064 and lead IGF-IR ASOs on cell proliferation rates in HaCaT keratinocytes. Subconfluent HaCaT cells were transfected with GSV alone (2 μg/ml) or GSV (2 μg/ml) complexed with antisense or control oligonucleotides (6.25, 25, 100 or 400 nM) every 24 h for up to 3 days. Cell number was estimated using amido black assay at the time of the first transfection, and at subsequent 24 h intervals. The data are represented as mean±SEM of two separate experiments in which cell number was determined in duplicate. UT=untreated cells, GSV=cells treated with GSV only.

FIG. 7 is a representation of the deoxyribonucleotide sequence of the region of the IGF-IR gene (M69229; SEQ ID NO:77) showing the location of targets for ISIS 175314, ISIS 175317 and ISIS 175323.

Figure 8:
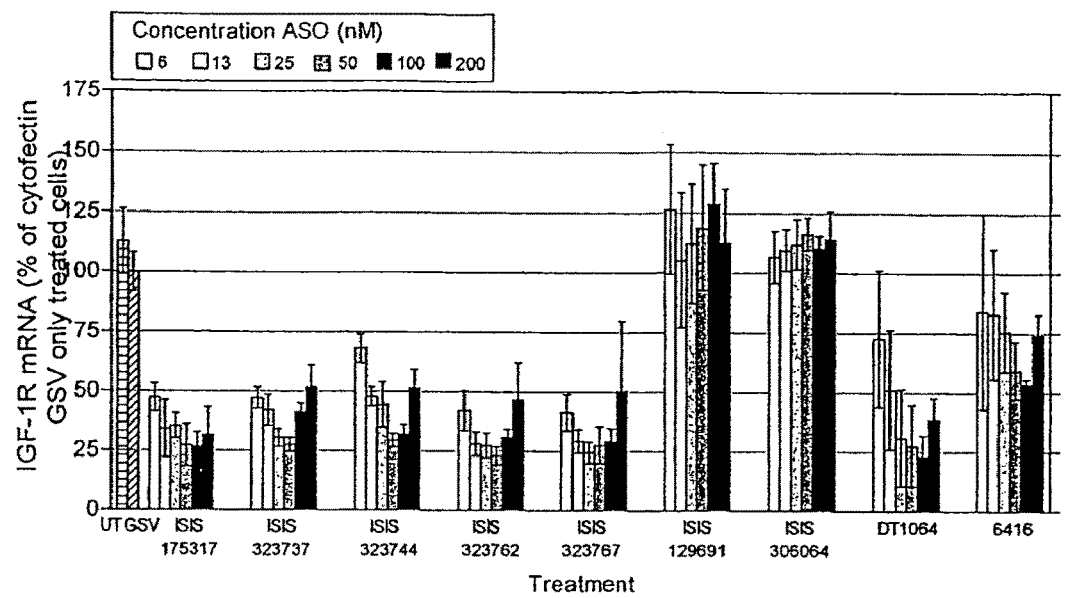

FIG. 8 is a graphical representation showing the effect of ISIS 175317, IGF-IR lead ASOs, and DT1064 on IGF-I receptor mRNA levels in HaCaT keratinocytes.

85% confluent HaCaT cells (passage 62-63) were treated for 20 h with GSV (2 μg/ml), with or without antisense or control oligonucleotides (6, 13, 25, 50, 100 or 200 nM). Total RNA was extracted and reverse transcribed before being assayed in duplicate by real-time PCR. IGF-I receptor mRNA was normalised against 18S and expressed as a percentage of IGF-IR mRNA levels in GSV-treated cells. Results represent mean±SD (n=4) from duplicate wells of two separate experiments. UT=untreated cells, GSV=cells treated with GSV only.

Figure 9:
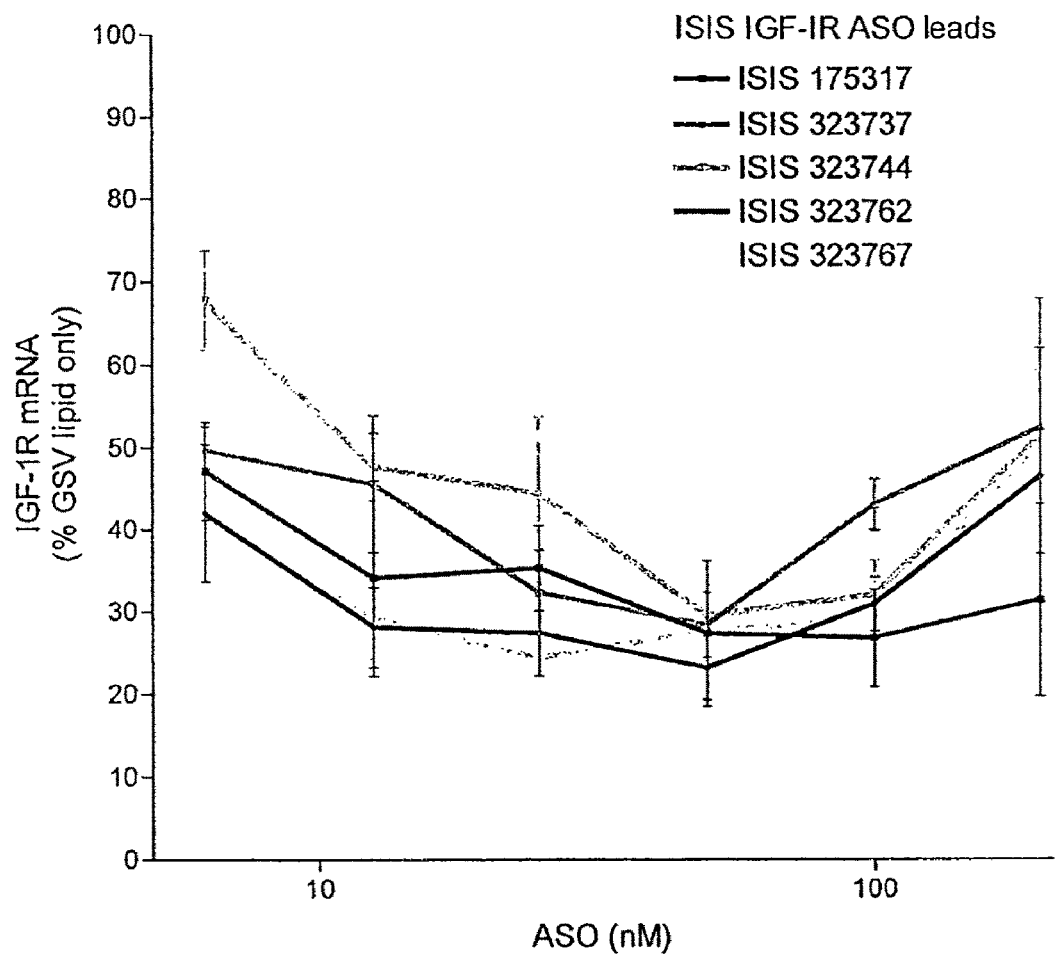

FIG. 9 is a graphical representation showing the effect of ISIS 175317, other IGF-IR lead ASOs, and DT1064 on IGF-I receptor mRNA levels in HaCaT keratinocytes. 85% confluent HaCaT cells (passage 62-63) were treated for 20 h with GSV (2 µg/ml), with or without antisense or control oligonucleotides (6, 13, 25, 50, 100, or 200 nM). Total RNA was extracted and reverse transcribed before being assayed in duplicate by real-time PCR. IGF-I receptor mRNA was normalised against 18S and expressed as a percentage of IGF-IR mRNA levels in GSV-treated cells. Results represent mean±SD (n=4) from duplicate wells of two separate experiments. UT=untreated cells, GSV=cells treated with GSV only.

In this experiment Lead IGF-IR ASO: ISIS 175317, Lead IGF-IR ASOs: ISIS 323737, ISIS 323744, ISIS 323762, ISIS 323767.

Figure 10:
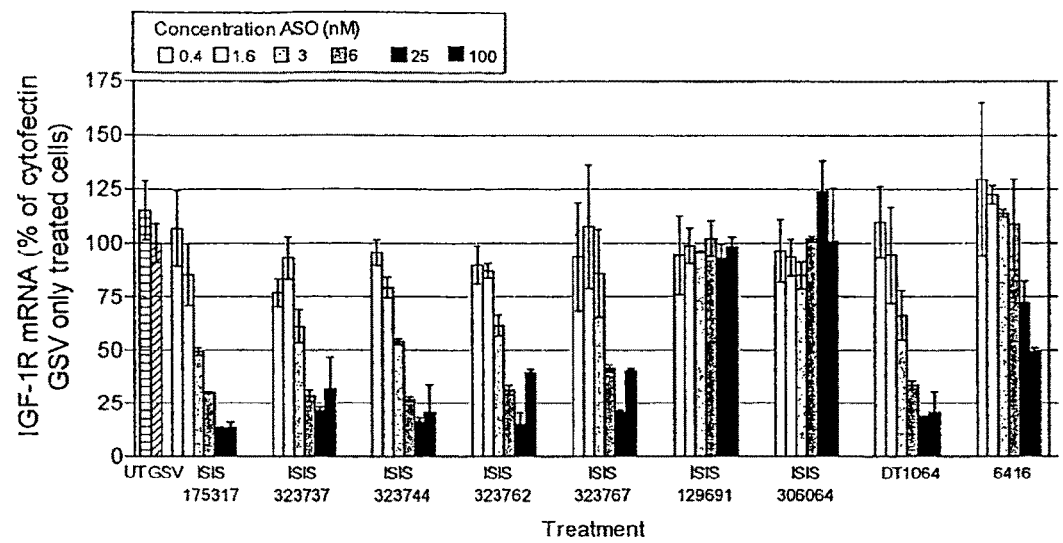

FIG. 10 is a graphical representation show the effect of ISIS 175317, four recently-identified IGF-IR lead ASOs, and DT1064 on IGF-I receptor mRNA levels in HaCaT keratinocytes. 85% confluent HaCaT cells (passage 45) were treated for 20 h with GSV (2 µg/ml), with or without antisense or control oligonucleotides (0.3, 1.6, 3, 6, 25, or 100 nM). Total RNA was extracted and reverse transcribed before being assayed in duplicate by real-time PCR. IGF-I receptor mRNA was normalised against 18S and expressed as a percentage of the IGF-IR mRNA levels in GSV-treated cells. Results represent mean±SD (n=2) from duplicate wells of a single experiment. UT=untreated cells, GSV=cells treated with GSV only.

In this experiment: Lead IGF-IR ASO: ISIS 175317. Lead IGF-IR ASOs: ISIS 323737, ISIS 323744, ISIS 323762, ISIS 323767. Control 2'MOE gapmers: ISIS 129691 (random), ISIS 306064 (8 mismatch). C-5 propyne IGF-IR ASO: DT1064. Control C-5 propyne: 6416 (15 mismatch).

Figure 11:
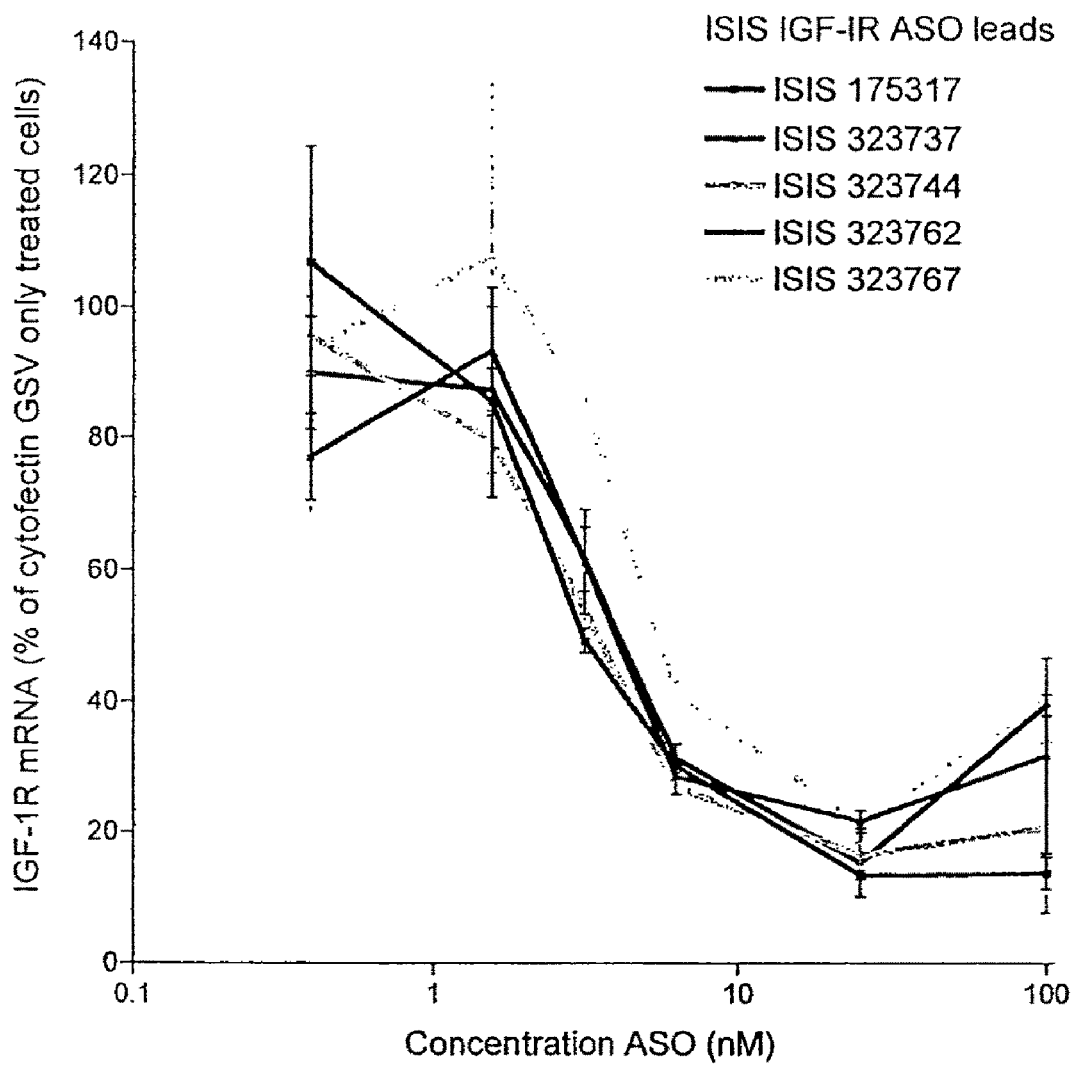

FIG. 11 is a graphical representation showing the concentration-response curves for the effects of the four recently identified ASOs and ISIS 175317 on relative IGF-IR mRNA levels in HaCaT keratinocytes. 85% confluent HaCaT cells (passage 45) were treated for 20 h with GSV (2 µg/ml), with or without antisense or control oligonucleotides (0.4, 1.6, 3, 6, 25, or 100 nM). Total RNA was extracted and reverse transcribed before being assayed in duplicate by real-time PCR. IGF-I receptor mRNA was normalised against 18S and expressed as a percentage of GSV-treated cells. Results represent mean±SD (n=2) from duplicate wells of a single experiment. UT=untreated cells, GSV=cells treated with GSV only.

In this experiment: Lead IGF-IR ASO: ISIS 175317. Lead IGF-IR ASOs: ISIS 323737, ISIS 323744, ISIS 323762, ISIS 323767.

Figure 12:
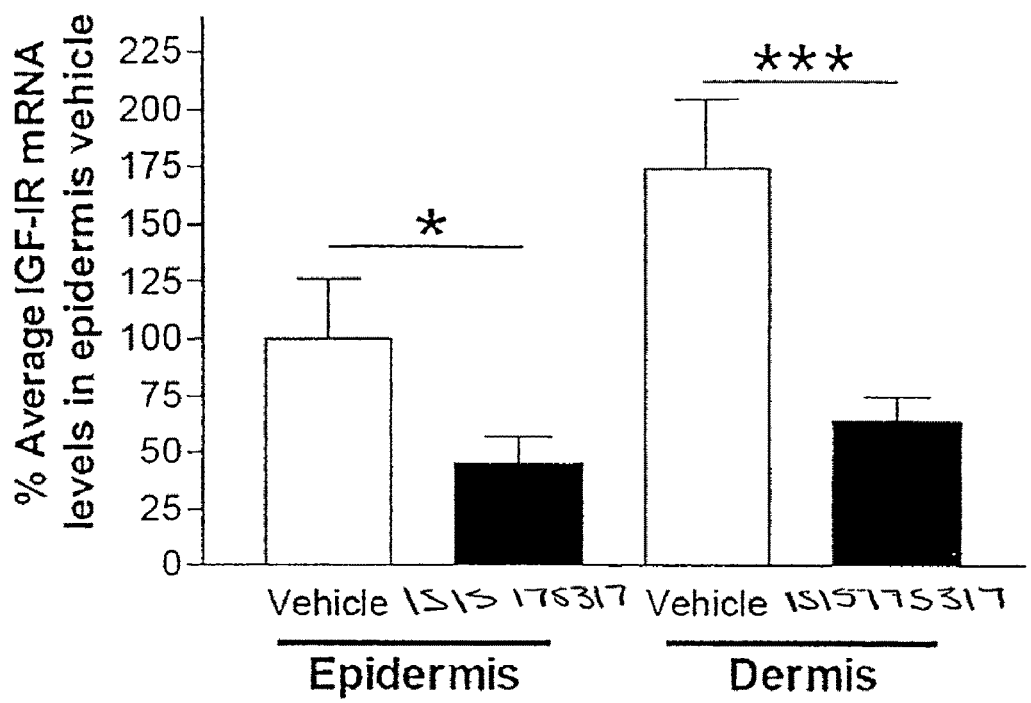

FIG. 12 is a graphical representation showing mean IGF-IR mRNA levels in psoriatic skin biopsies after topical application of ISIS 175317 (SEQ ID NO:125). Bars represent the average IGF-IR mRNA level in the epidermis and dermis of vehicle-treated and ISIS 175317 (SEQ ID NO: 125)-treated biopsies. Data are expressed relative to the average IGF-IR mRNA level in the epidermis of the vehicle treated samples, error bars are one standard deviation. Topically applied ISIS 175317 (SEQ ID NO:125) (10% in ISIS cream) significantly reduced IGF-IR mRNA levels in the epidermis and dermis 24 h after topical application to explants. In all cases n=11. (*=p<0.05, ***=p<0.001).

Figure 13:
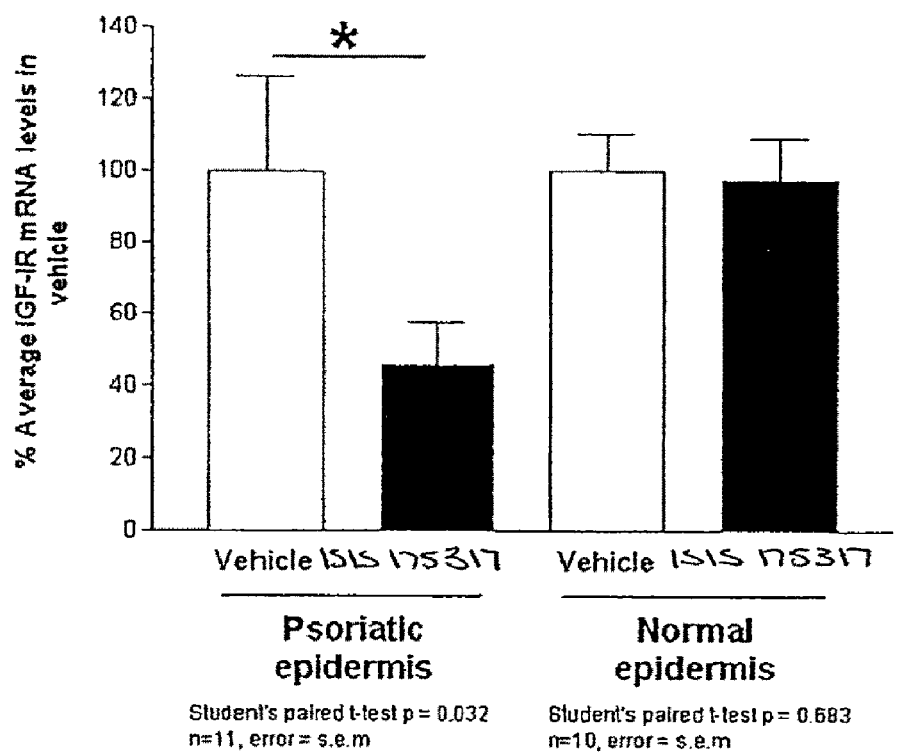

FIG. 13 is a graphical representation showing mean IGF-IR mRNA levels in psoriatic skin biopsies after topical application of ISIS 175317 (SEQ ID NO:125). Bars represent the average IGF-IR mRNA level in the psoriatic epidermis and normal epidermis of vehicle-treated and ISIS 175317 (SEQ ID NO:125)-treated biopsies. Data are expressed relative to the average IGF-IR mRNA level in the epidermis of the vehicle treated samples, error bars are one standard deviation. Topically applied ISIS 175317 (SEQ ID NO:125) (10% in ISIS cream) significantly reduced IGF-IR mRNA levels in the epidermis and dermis 24 h after topical application to explants. In all cases n=11. (*=p<0.05, ***=p<0.001).

Figure 14:
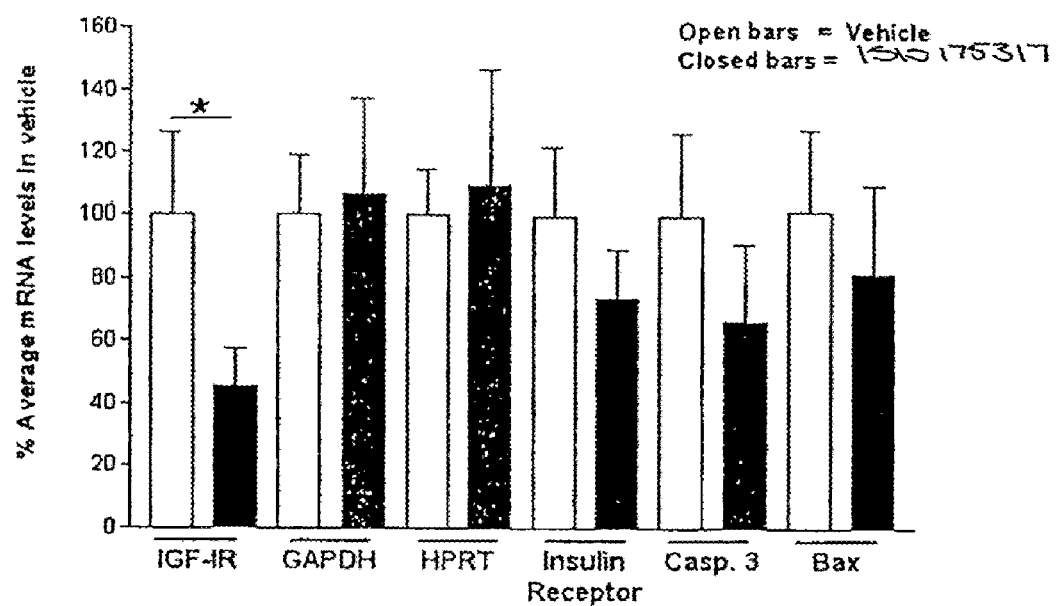

FIG. 14 is a graphical representation showing mean IGF-IR mRNA levels in psoriatic skin biopsies after topical application of ISIS 175317 to epidermis tissue showing specificity of ISIS 175317 to IGF-IR and not to GAPDH, HPRT, insulin receptor, Casp. 3 and Bax. Bars represent the average IGF-IR mRNA level in the epidermis and dermis of vehicle-treated and ISIS 175317-treated biopsies. Data are expressed relative to the average IGF-IR mRNA level in the epidermis of the vehicle treated samples, error bars are one standard deviation. Topically applied ISIS 175317 (10% in ISIS cream) significantly reduced IGF-IR mRNA levels in the epidermis and dermis 24 h after topical application to explants. In all cases n=11. (*=p<0.05, ***=p<0.001).

DETAILED DESCRIPTION OF THE PREFERRED EMBODIMENT

A. Overview of the Invention

The present invention employs compounds, preferably oligonucleotides and similar species for use in modulating the function or effect of nucleic acid molecules encoding the Insulin Like Growth Factor I receptor and, in a particular embodiment, the human Insulin Like Growth Factor-I receptor (IGF-IR). This is accomplished by providing oligonucleotides which specifically hybridize with one or more nucleic acid molecules encoding IGF-IR. As used herein, the terms "target nucleic acid" and "nucleic acid molecule encoding IGF-IR" have been used for convenience to encompass DNA encoding IGF-IR, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of IGF-1R. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.* 215: 403-410, 1990; Zhang and Madden, *Genome Res.* 7: 649-656, 1997).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell* 81: 611-620, 1995). Montgomery et al. have shown that the primary interference effects of dsRNA are posttranscriptional (Montgomery et al., *Proc. Natl. Acad. Sci. USA.* 95: 15502-15507, 1998). The post-transcriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature* 391: 806-811, 1998). Recently, it has been shown that it is, in fact, the single-stranded RNA oligomers of antisense polarity of the dsRNAs which are the potent inducers of RNAi (Tijsterman et al., *Science*, 295; 694-697, 2002).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

The candidate compounds of the present invention are referred to herein by ISIS number or SEQ ID NO. Preferred compounds are shown in Table 1.

Candidate compounds are also referred to herein as "lead" compounds.

One group of particularly preferred ASOs include ISIS 175308 (SEQ ID NO: 116), ISIS 175302 (SEQ ID NO: 110), ISIS 175314 (SEQ ID NO: 122), ISIS 175307 (SEQ ID NO: 115), ISIS 175317 (SEQ ID NO: 125) and ISIS 175323 (SEQ ID NO: 131).

Another group of particularly preferred ASOs include ISIS 323744 (SEQ ID NO:50), ISIS 323747 (SEQ ID NO:53), ISIS 323767 (SEQ ID NO:73), ISIS 323762 (SEQ ID NO:68) and ISIS 323737 (SEQ ID NO:43).

An even more particularly preferred ASO is ISIS 175317 (SEQ ID NO: 125).

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes IGF-IR.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding IGF-IR, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of the IGF-IR gene. "Modulators" are those compounds that decrease or increase the expression of a nucleic acid molecule encoding IGF-IR and which comprise at least a 8-nucleobase portion which is complementary to a preferred target segment. The screening method comprises the steps of contacting a preferred target segment of a nucleic acid molecule encoding IGF-IR with one or more candidate modulators, and selecting for one or more candidate modulators which decrease or increase the expression of a nucleic acid molecule encoding IGF-IR. Once it is shown that the candidate modulator or modulators are capable of modulating (e.g. either decreasing or increasing) the expression of a nucleic acid molecule encoding IGF-IR, the modulator may then be employed in further investigative studies of the function of IGF-1R, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature* 391: 806-811, 1998; Timmons and Fire, *Nature* 395: 854, 1998; Timmons et al., *Gene* 263: 103-112, 2001; Tabara et al., *Science* 282: 430-431, 1998; Montgomery et al., 1998, supra; Tuschl et al., *Genes Dev.* 13: 3191-3197, 1999; Elbashir et al., *Nature*, 411: 494-498, 2001; Elbashir et al., *Genes Dev.* 15: 188-200, 2001). For example, such double-stranded moieties have been shown to inhibit the target by the classical hybridization of antisense strand of the duplex to the target, thereby triggering enzymatic degradation of the target (Tijsterman et al., 2002, supra).

The compounds of the present invention can also be applied in the areas of drug discovery and target validation. The present invention comprehends the use of the compounds and preferred target segments identified herein in drug discovery efforts to elucidate relationships that exist between IGF-I, IGF-IR or IGF-I/IGF-IR interaction and a disease state, phenotype, or condition. These methods include detecting or modulating IGF-IR comprising contacting a sample, tissue, cell, or organism with the compounds of the present invention, measuring the nucleic acid or protein level of IGF-IR and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one non-limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.* 480: 17-24, 2000; Celis et al., *FEBS Lett.* 480: 2-16, 2000), SAGE (serial analysis of gene expression) (Madden et al., *Drug Discov. Today* 5: 415-425, 2000), READS (restriction enzyme amplification of digested cDNAs) (Prashar and Weissman, *Methods Enzymol.* 303: 258-272, 1999), TOGA (total gene expression analysis) (Sutcliffe et al., *Proc. Natl. Acad. Sci. USA* 97: 1976-1981, 2000), protein arrays and proteomics (Celis et al. 2000, supra; Jungblut et al., *Electrophoresis* 20: 2100-2110, 1999), expressed sequence tag (EST) sequencing (Celis et al., 2000, supra; Larsson et al., *J. Biotechnol.* 80: 143-157, 2000), subtractive RNA fingerprinting (SuRF) (Fuchs et al., *Anal. Biochem.* 286: 91-98, 2000; Larson et al., *Cytometry* 41: 203-208, 2000), subtractive cloning, differential display (DD) (Jurecic and Belmont, *Curr. Opin. Microbiol.* 3: 316-321, 2000), comparative genomic hybridization (Carulli et al., *J. Cell Biochem. Suppl.* 31: 286-296, 1998), FISH (fluorescent in situ hybridization) techniques (Going and Gusterson, *Eur. J. Cancer*, 35: 1895-1904, 1999) and mass spectrometry methods (To, *Comb. Chem. High Throughput Screen*, 3: 235-241, 2000).

The compounds of the invention are useful for research and diagnostics, because these compounds hybridize to nucleic acids encoding IGF-IR. For example, oligonucleotides that are shown to hybridize with such efficiency and under such conditions as disclosed herein as to be effective IGF-IR inhibitors of IGF-IR gene expression inhibitors will also be effective primers or probes under conditions favoring gene amplification or detection, respectively. These primers and probes are useful in methods requiring the specific detection of nucleic acid molecules encoding IGF-IR and in the amplification of said nucleic acid molecules for detection or for use in further studies of IGF-IR or its gene. Hybridization of the antisense oligonucleotides, particularly the primers and probes, of the invention with a nucleic acid encoding IGF-IR can be detected by means known in the art. Such means may include conjugation of an enzyme to the oligonucleotide, radiolabelling of the oligonucleotide or any other suitable detection means. Kits using such detection means for detecting the level of IGF-IR in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of the IGF-IR gene is treated by administering antisense compounds in accordance with this invention. For example, in one non-limiting embodiment, the methods comprise the step of administering to the animal in need of treatment, a therapeutically effective amount of an IGF-IR gene expression inhibitor. The IGF-IR gene expression inhibitors of the present invention effectively inhibit the activity of the IGF-IR protein or inhibit the expression of the IGF-IR gene. In one embodiment, the activity or expression of IGF-IR or its gene in an animal is inhibited by about 10%. Preferably, the activity or expression of IGF-IR or its gene in an animal is inhibited by about 30%. More preferably, the activity or expression of IGF-IR or its gene in an animal is inhibited by 50% or more.

For example, the reduction of the expression of the IGF-IR gene may be measured in serum, adipose tissue, skin cells, liver or any other body fluid, tissue or organ of the animal. Preferably, the cells contained within said fluids, tissues or organs being analyzed contain a nucleic acid molecule encoding an IGF-IR protein.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254: 1497-1500, 1991.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta,* 78: 486-504, 1995) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H -pyrimido[5,4-b][1,4]benzoxazin-2(3H)-one), phenothiazine cytidine (1H -pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 30: 613, 1991, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety. Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)

phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Antiinflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O -Dimethoxytrityl-thymidine intermediate for 5-methyl dC amidite, 5'-O-Dimethoxytrityl-2'-deoxy-5-methylcytidine intermediate for 5-methyl-dC amidite, 5'-O -Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5- methyl-cytidine penultimate intermediate, [5'-O-(4,4'-Dimethoxytriphenylmethyl)-2'-O-(2-methoxyethyl)-N⁴-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N⁶-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N⁴-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O²-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligo-nucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, Ph.D. Thesis, University of Colorado, 1996; Scaringe et al., *J. Am. Chem. Soc.* 120: 11820-11821; 1998; Matteucci and Caruthers, *J. Am. Chem. Soc.* 103: 3185-3191, 1981; Beaucage and Caruthers, *Tetrahedron Lett.* 22: 1859-1862, 1981; Dahl et al., *Acta Chem. Scand.* 44: 639-641; 1990, Reddy et al., *Tetrahedrom Lett.* 25: 4311-4314, 1994; Wincott et al., *Nucleic Acids Res.* 23: 2677-2684, 1995; Griffin et al., *Tetrahedron* 23: 2301-2313, 1967a; Griffin et al., *Tetrahedron* 23: 2315-2331, 1967b).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric
Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy
Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-0-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting IGF-1R mRNA

In accordance with the present invention, a series of nucleic acid duplexes comprising the antisense compounds of the present invention and their complements can be designed to target IGF-IR mRNA. The nucleobase sequence of the antisense strand of the duplex comprises at least a portion of an oligonucleotide selected from SEQ ID NOs: 1 through 76 and SEQ ID NO: 100 through 136 shown in Table 1 including preferred ASO's ISIS 175308, 175302, 175314, 175307, 175317, 175323, 232744, 323747, 323767, 323762 and 323737. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine(dT) would have the following structure:

```
cgagaggcggacgggaccgTT    Antisense Strand    [SEQ ID NO: 92]
||||||||||||||||||||
TTgctctccgcctgccctggc    Complement          [SEQ ID NO: 93]
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate IGF-IR gene expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 266: 18162-18171, 1991. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE (trademark) MDQ) or, for individually prepared samples, on a commercial CE apparatus (e.g., Beckman P/ACE (trademark) 5000, ABI 270). Base and backbone composition was confirmed by mass analysis of the compounds utilizing electrospray-mass spectroscopy.

All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% w/v fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis. For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds

When cells reached 65-75% confluency, they were treated with oligonucleotide. For cells grown in 96-well plates, wells were washed once with 100 μL OPTI-MEM (trademark)-1 reduced-serum medium (Invitrogen Corporation, Carlsbad, Calif.) and then treated with 130 μL of OPTI-MEM (trademark)-1 containing 3.75 μg/mL LIPOFECTIN (trademark) (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO:79) which is targeted to human H-ras, or ISIS 18078, (GTGCGCGCGAGCCCGAAATC, SEQ ID NO:80) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO:81, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of IGF-1R Gene Expression

Antisense modulation of IGF-1R gene expression can be assayed in a variety of ways known in the art. For example, IGF-IR mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM (trademark) 7600, 7700, or 7900 Sequence Detection System, available from PE-Applied Biosystems, Foster City, Calif. and used according to manufacturer's instructions.

Protein levels of IGF-IR can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to IGF-IR can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of IGF-1R Gene Expression Inhibitors Phenotypic Assays Once IGF-IR gene expression inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of IGF-IR in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with IGF-IR gene expression inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the IGF-IR gene expression inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or IGF-IR gene expression inhibitor. Furthermore, to prevent the doctors from being biased in treatments, they are not informed as to whether the medication they are administering is a IGF-IR gene expression inhibitor or a placebo. Using this randomization approach, each volunteer has the same chance of being given either the new treatment or the placebo.

Volunteers receive either the IGF-IR gene expression inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding IGF-IR or IGF-IR protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and IGF-IR gene expression inhibitor treatment. In general, the volunteers treated with placebo have little or no response to treatment, whereas the volunteers treated with the IGF-IR gene expression inhibitor show positive trends in their disease state or condition index at the conclusion of the study.

Example 12

RNA Isolation

Poly(A)+ mRNA Isolation

Poly(A)+ mRNA was isolated according to Miura et al. (Clin. Chem. 42: 1758-1764, 1996). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96 (trademark) kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96 (trademark) well plate attached to a QIAVAC (trademark) manifold fitted with a waste collection tray and attached to a vacuum source. Vacuum was applied for 1 minute. 500 μL of Buffer RW1 was added to each well of the RNEASY 96 (trademark) plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96 (trademark) plate and the vacuum applied for a period of 90 seconds. The Buffer RPE wash was then repeated and the vacuum was applied for an additional 3 minutes. The plate was then removed from the QIAVAC (trademark) manifold and blotted dry on paper towels. The plate was then re-attached to the QIAVAC (trademark) manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of IGF-1R mRNA Levels

Quantitation of IGF-1R mRNA levels was accomplished by real-time quantitative PCR using the ABI PRISM (trademark) 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM (trademark) Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM (registered trademark) Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM (registered trademark) Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen (trademark) (Molecular Probes, Inc. Eugene, Oreg.). GAPDH expression is quantified by real time RT-PCR, by being run simultaneously with the target, multiplexing, or separately. Total RNA is quantified using RiboGreen (trademark) RNA quantification reagent (Molecular Probes, Inc. Eugene, Oreg.). Methods of RNA quantification by RiboGreen (trademark) are taught in Jones et al. (*Analytical Biochemistry* 265: 368-374, 1998).

In this assay, 170 μL of RiboGreen (trademark) working reagent (RiboGreen (trademark) reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Figure 2B:
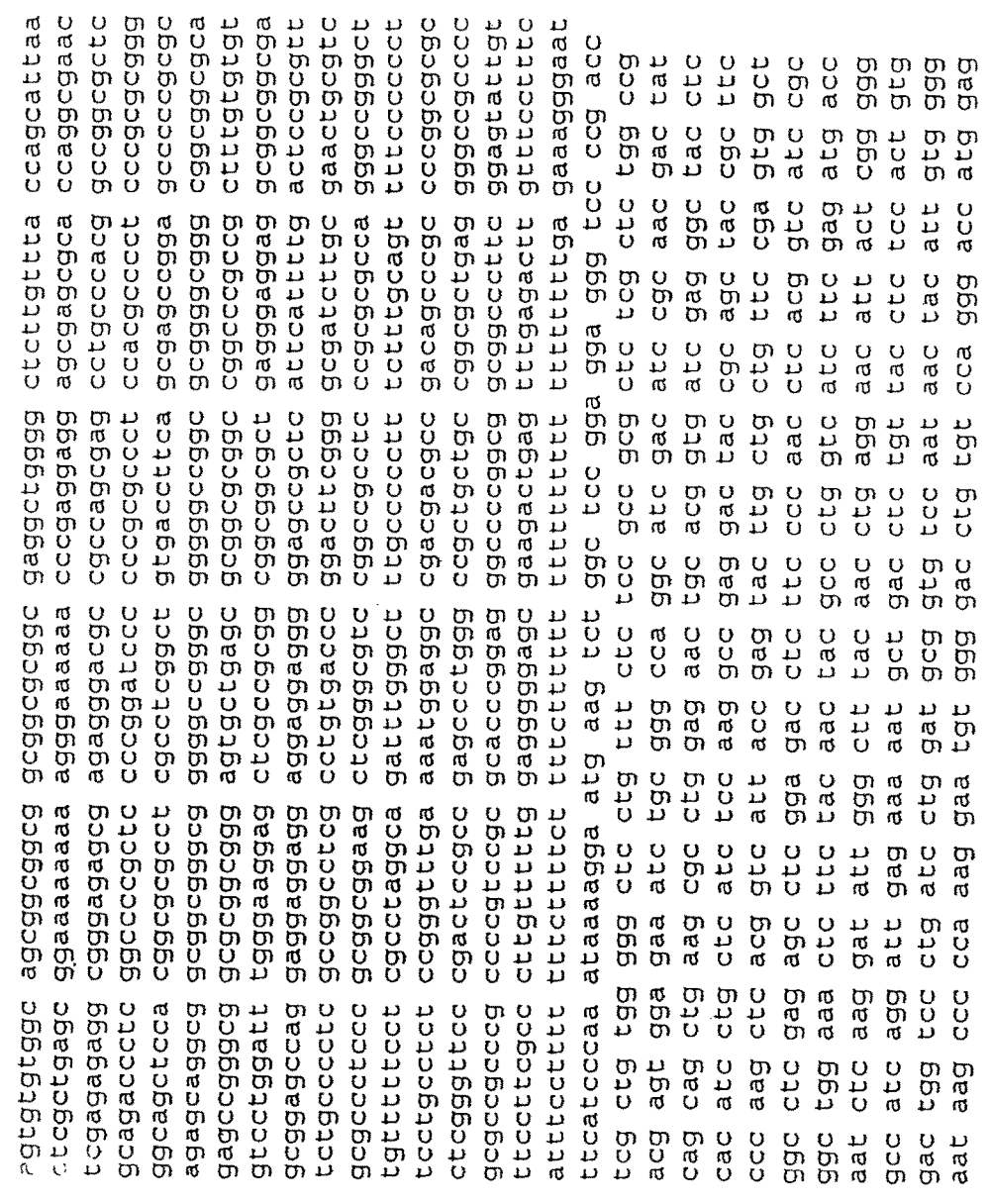

Probes and primers to human IGF-IR were designed to hybridize to the IGF-IR nucleotide sequence, using published sequence information (GenBank accession number NM000875 (FIGS. 2A and 2B), incorporated herein as SEQ ID NO:76 or M69229 (SEQ ID NO:77) which is the 5' untranslated of the IGF-IR gene sequence). For human IGF-IR the PCR primers were:

```
forward primer:
CCCTTTCTTTGCAGTTTTCCC;          (SEQ ID NO: 82 -
                                 ISIS 161212)
```

-continued

```
reverse primer:
CGTCGTCGGCCTCCATT;           (SEQ ID NO: 83 -
                                  161214)
and the PCR probe was:
FAM- CCTTCCTGCCTCTCCGGGTTTGA-TAMRA (SEQ ID NO: 84 -
                                    ISIS 161215)
``` where FAM is the fluorescent dye and TAMRA is the quencher dye. For human GAPDH the PCR primers were:

```
forward primer:
GAAGGTGAAGGTCGGAGTC          (SEQ ID NO: 94)

reverse primer:
GAAGATGGTGATGGGATTTC         (SEQ ID NO: 95)
and the PCR probe was:
5' JOE-CAAGCTTCCCGTTCTCAGCC- (SEQ ID NO: 95)
TAMRA 3'
``` where JOE is the fluorescent reporter dye and TAMRA is the quencher dye.

Example 14

Northern Blot Analysis of IGF-1R mRNA Levels

Eighteen hours after antisense treatment, cell monolayers were washed twice with cold PBS and lysed in 1 mL RNA-ZOL (trademark)(TEL-TEST "B" Inc., Friendswood, Tex.). Total RNA was prepared following manufacturer's recommended protocols. Twenty micrograms of total RNA was fractionated by electrophoresis through 1.2% w/v agarose gels containing 1.1% v/v formaldehyde using a MOPS buffer system (AMRESCO, Inc. Solon, Ohio). RNA was transferred from the gel to HYBOND (trademark)-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER (trademark) UV Crosslinker 2400 (Stratagene, Inc, La Jolla, Calif.) and then probed using QUICK-HYB (trademark) hybridization solution (Stratagene, La Jolla, Calif.) using manufacturer's recommendations for stringent conditions.

To detect human IGF-IR an IGF-IR specific probe was prepared by PCR using the forward primer for human IGF-IR CCCTTTCTTTGCAGTTTTCCC (SEQ ID NO:82-ISIS 161212) and the reverse primer for human IGF-IR reverse primer sequence CGTCGTCGGCCTCCATT (SEQ ID NO:83-ISIS 161214). To normalize for variations in loading and transfer efficiency membranes were stripped and probed for human glyceraldehyde-3-phosphate dehydrogenase (GAPDH) RNA (Clontech, Palo Alto, Calif.). Hybridized membranes were visualized and quantitated using a PHOSPHORIMAGER (trademark) and IMAGEQUANT (tradeamrk) Software V3.3 (Molecular Dynamics, Sunnyvale, Calif.). Data was normalized to GAPDH levels in untreated controls.

Example 15

Antisense Inhibition of Human IGF-1R Expression

In accordance with the present invention, a series of antisense compounds were designed to target different regions of the human IGF-IR mRNA or the 5' untranslated region, using published sequences set forth in accession No. NM000875 (SEQ ID NO:76) and M69229 (SEQ ID NO:77). The compounds are shown in Table 1. "Target site" indicates the first (5'-most) nucleotide number on the particular target sequence to which the compound binds. All compounds in Table 1 are ASOs of either the 5' untranslated region or the coding region of the IGF-IR. The compounds were analyzed for their effect on human IGF-IR mRNA levels by quantitative real-time PCR as described in other examples herein (see FIG. 3 and Table 1). Data are averages from three experiments. The positive control for each datapoint is identified in the Table 1 by sequence ID number. If present, "N.D." indicates "no data".

As shown in Table 1, some lead compounds demonstrated at least some inhibition of IGF-IR expression in this assay and are therefore preferred. Examples of preferred ASO's include ASO's ISIS 175308, 175302, 175314, 175307, 175317, 175323, 323744, 323747, 323767, 323762 and 323737. The target regions to which these preferred sequences are complementary are herein referred to as "preferred target segments" and are therefore preferred for targeting by compounds of the present invention. SEQ ID Nos 137 through 171 represent preferred target segments identified in IGF-1R. The "Target site" in Table 1 indicates the first (5'-most) nucleotide number on the particular target nucleic acid to which the oligonucleotide binds.

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of IGF-IR.

According to the present invention, antisense compounds include antisense oligomeric compounds, ASOs, ribozymes, external guide sequence (EGS) oligonucleotides, alternate splicers, primers, probes, and other short oligomeric compounds which hybridize to at least a portion of the target nucleic acid.

The purpose of this Example is to investigate the epidermal localization of ASOs with full phosphorothioate 2'-O-(2-methoxy)ethyl gapmer (2' MOE gapmer) or C5-propynyl-dU,dC-phosphorothioate (C5-propyne) chemistry following topical application to psoriatic skin. Studies were performed on ex vivo psoriatic skin explants as shown in FIG. 1, with confocal microscopy, direct fluorescence and immunohistochemistry used to detect ASO localization. In previous studies, an FITC conjugated C5-propyne ASO has been shown to reach the basal layer of the epidermis after topical application to psoriatic skin (White et al., Journal of Investigative Dermatology 118: 1003-1007, 2002). In this Example, both 2' MOE gapmer and C5-propyne ASOs were found to penetrate into the epidermis of psoriatic skin biopsies when formulated in either 5% w/v methylcellulose or cream. ASOs of both chemistries seemed to accumulate in the basal layers of the epidermis as assessed by both direct fluorescence microscopy and immunohistochemical detection of ASOs. The localization of FITC-ASOs was not obviously different from that of non-FITC ASOs.

Topical Application of ASOs

C5-propyne ASOs have been shown to accumulate in basal keratinocytes of human psoriatic (but not normal) skin following topical application (White et al., 2002, supra), presumably due to the compromised barrier function of the stratum corneum in psoriasis. In addition, a phosphorothioate ASO was shown to accumulate in the basal keratinocytes of normal human skin when formulated in a cream (Mehta et al., *J. Invest. Dermatol.* 115: 805-812, 2000). A phosphorothioate-phosphodiester hybrid ASO in distilled water failed to accumulate in basal keratinocytes following topical application to human skin despite appearing to cross the stratum corneum and accumulating in the cytoplasm of keratinocytes in the upper layers of the epidermis (Wingens et al., *Lab Invest.* 79: 1415-1424, 1999).

The present Example investigated the localization of 2' MOE gapmer ASOs in human psoriatic skin following topical application.

Oligonucleotides

The oligonucleotides employed are listed in Table 4.

TABLE 4

List of the four oligonucleotides used in topical application studies. Underlined sections bear 2' MOE chemistry.

| Chemistry | Identification | Sequence | Detected by 2E1 Ab |
|---|---|---|---|
| C5 propyne | R451 | UAACACGACGCGAAU-FITC [SEQ ID NO: 53] | Unknown |
| 2' MOE | ASO 251741 | FITC-<u>TCC</u>GTCATCGCT<u>CCT</u>CAGGG [SEQ ID NO: 54] | Yes |
| 2' MOE | ASO 13920 | <u>TCC</u>GTCATCGCT<u>CCT</u>CAGGG [SEQ ID NO: 55] | Yes |
| 2' MOE | ASO 147979 | FITC-<u>TCCCGC</u>CTGTGACA<u>TGCATT</u> [SEQ ID NO: 56] | No |

Collection of Psoriatic Skin Biopsies

Psoriatic skin biopsies were collected from volunteers. Up to three 8 mm, full thickness, punch biopsies were collected from each volunteer by a dermatologist. The area from which biopsy is taken was not cleaned or disinfected prior to biopsy collection. Biopsies were immediately placed on gauze (wetted with PBS) and stored on ice until used (~2 hrs).

At the time of collection, the severity of psoriasis in the biopsies was scored using the PRS (parameter rating scale) component of the PASI (psoriasis area severity index) score (Fredriksson et al., Dermatologica 157: 238-244, 1978). In brief, erythema (redness), induration (swelling) and desquamation (flaking) were each scored from 0 (absent) to 4 (severe) to give a PRS score of 0 to 12.

Live Confocal Microscopy 24 hrs after application of FITC-ASOs, biopsies were removed from culture dishes and placed on coverslips, stratum corneum down, and a drop of PBS was placed on the exposed dermis to keep it moist. Live confocal microscopy was then performed as described previously (White et al., *J. Invest. Dermatol.* 112: 887-892, 1999; White et al., 2002, supra). In summary, topical application of FITC-ASO was assessed with excitation at 488 nm (argon ion laser) and detection at 515 nm. The instrument used was an IX70 Olympus inverted microscope (Olympus Australia, Melbourne, Australia) attached to an Optiscan f900e confocal system (Optiscan Pty, Melbourne, Australia).

Confocal microscopy results in sections en face to the surface of the skin and for each biopsy a series of images was taken at increasing depth into the epidermis. Previous work indicates that fluorescence can be detected up to 100 μm under the surface using this method.

In order to determine the epidermal location of FITC-ASO containing keratinocytes, the criteria of White et al., (1999, supra) were used as a guide. These criteria were:
cellular morphology
presence and size of nuclei:
corneocytes anuclear
nuclei in keratinocytes of the stratum granulosum >15 μm
basal keratinocyte nuclei <10 μm
depth of cells (basal keratinocytes at least 50 μm below the surface).

Processing of Tissue Samples

Following confocal microscopy, entire biopsies were fixed for 24 hrs in 4% paraformaldehyde (4° C.) followed by 48 hrs in 0.5 M sucrose (4° C.). Biopsies were then submerged in graded ethanol (70%, 80%, 90% and 2×100% each for 90 min) followed by 2×90 min in limonene and 2×90 min in paraffin wax (65° C.) using a tissue processor (Shandon Citadel 1000, Shandon Inc, Pittsburgh, USA). Following processing, biopsies were embedded in paraffin (Shandon Histocentre 2, Shandon Inc) and stored at room temperature until required.

5 μm thick sections transverse to the epidermis were cut (Leica RM2035 microtome, Leica Instruments, Wetzlar, Germany), transferred to silane-coated glass slides and dried at 37° C. overnight. Sections were stored in a sealed container at room temperature until processed for histological assessment of psoriasis, direct fluorescence or immunohistochemistry.

Histological Assessment of Psoriasis

Sections (5 μm) from each psoriatic skin biopsy were de-waxed by immersion in limonene for 2×5 min followed by consecutive 5 min washes in graded ethanol (100%, 90%, 80%, 70% and 50%) and 5 min in water. Sections were than stained with Harris' haematoxylin (stains cell nuclei blue) and eosin (stains cytoplasm and other tissue structures pink) before being washed in ethanol (2×15 sec) and limonene (2×15 sec). Sections were then cover-slipped with DPX mounting media (BDH Laboratory Supplies, Poole, England).

Detection of ASOs by Direct Fluorescence

Sections were de-waxed and washed as described above before being cover-slipped with MOWIOL mounting media (Biosciences inc, La Jolla, USA) containing 2.5% DABCO anti-fade (Sigma, St Louis, USA). Image brightness was adjusted to correct for auto-fluorescence. Auto-fluorescence was defined as the fluorescence produced from vehicle (5% w/v methylcellulose or cream) treated sample.

Detection of ASOs by Immunohistochemistry (2E1 Ab)

Sections were de-waxed as described above and ASOs detected using the affinity purified 2E1-B5 antibody (Berkeley Antibody Company, Berkeley, USA) supplied to us by Isis Pharmaceuticals. The 2E1-B5 antibody is a mouse IgG1 that recognizes TGC and GC motifs in phosphorothioate oligonucleotides (Mehta et al., 2000, supra).

Sections were incubated in 1% v/v $H_2O_2$ in methanol for 30 min to quench endogenous peroxidase activity, washed with PBS and incubated for 10 min in DAKO (registered trademark) ready-to-use proteinase K (DAKO corporation, Carpenteria, USA). Sections were blocked with 1% w/v BSA/20 ug/ml sheep IgG in PBS for 20 min before a 45 min incubation with the 2E1 primary antibody (1/4000 dilution). Sections were again washed with PBS and the primary antibody detected using the Vectastain (registered trademark) Elite mouse ABC kit (Vector Laboratories, Burlingame, USA). The Vectastain (registered trademark) Elite mouse ABC kit uses a secondary biotinylated anti-mouse IgG that is then detected with an avidin and biotinylated horseradish peroxidase complex. DAB was used as the substrate such that antibody localization was indicated by a brown coloration.

Image Capture

With the exception of confocal images (see 'Live confocal microscopy' in this section), all images were captured using a Sony DXC-950P colour digital camera (Sony, Tokyo, Japan) attached to a Nikon E600 microscope (Nikon Corporation, Tokyo, Japan) and controlled by a MCID M4 imaging system (Imaging Research Inc, St Catharines, Canada). Fluorescence excitation was provided by a Nikon HB-10103AF high-pressure mercury lamp power supply (Nikon Corporation) and viewed through an appropriate barrier filter.

Assessment of Psoriatic Skin Biopsies

Psoriatic skin was collected from the abdomen, thigh, back, buttocks, shin, elbow or hips of volunteers. Up to three biopsies were taken from each individual and biopsies from each individual were allocated to separate experimental groups.

The severity of psoriasis, as determined using the PRS, was 6.8±1.7 (mean±SD, n=42) with a range from 3 to 9. The PRS was not significantly different across experimental groups (p=0.9609, Kruskal-Wallis non-parametric ANOVA).

Under histological examination, all biopsies appeared psoriatic although there was considerable variation in morphology between biopsies. In addition to variations in the severity of psoriasis, the observed variation may be due to the different body locations from which the biopsies were taken. A thickened basal keratinocyte layer was visible in all biopsies, and in many (but not all) biopsies, elongated rete ridges and cell nuclei in the stratum corneum (parakeratosis) were apparent. Cells resembling invading leukocytes were seen in the dermis of most biopsies.

Example 16

Topical Application of ASOs

To confirm the results of White et al., (2002, supra), which demonstrated localization of C5-propyne ASOs in basal keratinocytes of psoriatic skin biopsies, and to investigate the distribution of 2' MOE ASOs following topical application in 5% w/v methylcellulose or cream, the following FITC conjugated ASOs were applied to separate psoriatic skin biopsies:
  0.1% w/w R451 (C5-propyne) in 5% w/v methylcellulose;
  0.1% w/w ISIS 251741 (2' MOE) in 5% w/v methylcellulose;
  0.1% w/w ISIS 251741 (2' MOE) in cream.

Direct fluorescence microscopy showed both the 2' MOE gapmer ASO and the C5-propyne ASO in the epidermis of psoriatic skin lesions, with fluorescence clearly present in nuclei of basal keratinocytes. Fluorescence can also be seen in nuclei of cells that appear to be invading leukocytes located in the dermis. There was no apparent difference in the pattern of fluorescence produced by the 2' MOE gapmer and C5-propyne ASOs following topical application.

Furthermore, 2' MOE gapmer ASOs in cream showed an epidermal distribution comparable to that see for 2' MOE gapmer ASOs formulated in 5% w/v methylcellulose, with no apparent difference in epidermal localization of fluorescence.

These results were confirmed by live confocal microscopy which also demonstrated nuclear localization of FITC-AONs in cells fitting the criteria for basal keratinocytes; cell nuclei <10 μm and least 50 μm below the surface). Interestingly, ASO appear to be in the nuclei of parakeratotic corneocytes. The cells appear intermediate between keratinocytes of the stratum granulosum and corneocytes, although they present at the surface of the epidermis. In some cases these keratinocytes appear to exclude ASO from their nuclei. Features consistent with psoriasis were clearly observed which show either keratinocytes of the stratum granulosum with nuclei much smaller than would be expected in normal skin, and/or basal keratinocytes much closer to the surface than would be expected in normal skin.

Example 17

Detection of a 5% ASO, Containing a 0.1% FITC-ASO Spike, Formulated in Cream

Higher ASO concentrations may be employed. Therefore, it is useful to determine if an FITC-ASO contained as a 0.1% spike in a 5% total ASO formulation could be detected by direct fluorescence microscopy and/or confocal microscopy. 2' MOE FITC-ASO ISIS 251741 (0.1% w/w) mixed with the non-FITC 2' MOE ISIS 13920 (4.9% w/w) in cream was applied to psoriatic skin biopsies for this purpose.

Direct fluorescence and confocal microscopy images from samples treated with a 5% 2' MOE containing a 0.1% FITC-ASO spike showed fluorescence in basal keratinocytes. The increased concentration of ASO did not appear to alter the epidermal localization of fluorescence produced by the FITC-ASO, with localization similar to that observed following the application of 0.1% FITC-ASO alone.

Example 18

Benchmarking Antisense Oligonucleotides (ASOs)

Antisense oligonucleotides (ASOs) that target IGF-IR mRNA are proposed to be effective new therapeutic agents to reduce inflammatory and/or proliferative disorders. The purpose of this Example is to benchmark three preferred IGF-IR ASOs with full phosphorothioate "5-10-5," 2' MOE gapmer chemistry against DT1064 (SEQ ID NO:78), a 15 mer C5-propynyl-dU,dC-phosphorothioate ASO. All C's and U's in DT1064 are subjected to C5 propynylation. Studies were performed in a human keratinocyte transfection system, with IGF-IR mRNA and protein levels and cell proliferation as end-points. In previous studies, DT1064 has successfully inhibited IGF-IR expression in this system (Wraight et al., 2000, supra; Fogarty et al., Antisense Nucleic Acid Drug Development 12: 369-377, 2002).

The results show that the three IGF-IR ASOs reduced IGF-iR mRNA with the same potency as DT1064. IGF-IR protein levels and cell proliferation rates were also reduced by the ASOs.

These findings support the use of the 2' MOE gapmer chemistry for knockdown of IGF-IR mRNA. Based on its performance in the studies presented in this Example, ASO 175317 is one 2' MOE gapmer ASO particularly useful for therapeutic trials.

2' MOE Gapmers

The three "5-10-5," 2' MOE gapmers, phosphorothioate leads showed concentration-dependent inhibition of IGF-IR mRNA in A549 cells (human lung epithelial cells) as assessed by real-time PCR FIG. 3. The three leads were assessed for activity in a human keratinocyte skin cell transfection system.

In Vitro Benchmarking of 2' MOE Gapmers

The three lead ASOs have been "benchmarked" in vitro against DT1064 with the following endpoints:—
1. Total IGF-IR mRNA assessed by real-time PCR;
2. Total cellular IGF-IR protein determined by immunoblot;

3. HaCaT keratinocyte cell growth rate assayed by amido black dye-binding;

Oligonucleotides

Oligonucleotides used in this study are shown in Table 2.

TABLE 2

List of the seven oligonucleotides used for in vitro testing.

| | Chemistry | Identification | Antisense/Control |
|---|---|---|---|
| 1 | C5-propynyl-dU,dC-phosphorothioate | DT1064 | A |
| 2 | (Abbreviation: C5-propyne) | DT6416 | C (mismatch) |
| 3 | | R451 | C (random) |
| 4 | 2'-O-(2-methoxy)ethyl | ISIS 175314 | A |
| 5 | 5,10,5-gapmer, | ISIS 175317 | A |
| 6 | phosphorothioate throughout | ISIS 175323 | A |
| 7 | (Abbreviation: 2' MOE gapmer) | ISIS 129691 | C (random) |

The nucleotide sequences of the ASOs are present in FIG. 3.

Cell Culture

Spontaneously immortalized human keratinocyte cell line, HaCaT (Boukamp et al., 1988, supra) were used in this study. Cells were maintained as monolayer cultures in Dulbecco's modified Eagle's medium (DMEM) supplemented with 10% w/v foetal calf serum (FCS) at 37° C. in an atmosphere of 5% V/V $CO_2$.

Transfection of Keratinocytes with Antisense Oligonucleotides

HaCaT keratinocytes (passage number 44 to 47) were seeded into the wells of 96-well (real-time PCR), 24-well (cell proliferation) or 12-well (immunoblot or apoptosis) plates. 85-95% confluent cells were treated with the liposome preparation, Cytofectin GSV (GSV; Glen Research, Sterling Va., USA) alone, or complexed with antisense or control oligonucleotides. Untreated cells were also studied (untreated control). Each antisense or control oligonucleotide was diluted in serum-free DMEM to 20× the desired final concentration and mixed with an equal volume of GSV (40 µg/ml). Lipid/oligonucleotide mixtures were allowed to complex at room temperature for 10 mins then diluted tenfold with DMEM containing 10% w/v FCS. Cells were transfected with final concentrations of 6.25, 25, 100 or 400 nM oligonucleotide and 2 µg/ml GSV. Transfections were performed in duplicate wells, while untreated and GSV-treated cells were run in four replicate wells.

IGF-IR mRNA levels

Total RNA was extracted using a RNEASY (registered trademark) Mini kit (Qiagen Inc., Valencia, Calif., USA) and 0.5 to 1 µg reverse transcribed using the GeneAmp (registered trademark) RNA PCR kit (Applied Biosystems, Foster City, Calif., USA), according to the manufacture's instructions. Semi-quantitative real-time PCR was used to determine the amount of IGF-I receptor mRNA in the sample relative to cells treated with GSV alone. Pre-developed reagents for the human IGF-I receptor (Applied Biosystems, Product No. 4319442F) and 18S (Product no. 4319413E) containing primers and TaqMan (registered trademark) fluorescent probes were used in a multiplex PCR reaction to simultaneously amplify both products in each sample. An ABI Prism (trademark) 7700 sequence detector (Applied Biosystems) was used for the analysis. IGF-1R mRNA levels were then normalized to 18S. Two transfection protocols were used—cells were transfected (1) once, 18 h before RNA extraction, or (2) a total of twice, at 24 and 48 h before RNA extraction.

IGF-1R Protein Levels

Following transfections with oligonucleotides every 24 h for three days, cell monolayers were washed with PBS, then lysed in a buffer containing 50 mM HEPES pH 7.4, 150 mM NaCl, 1.5 mM $MgCl_2$, 10% v/v glycerol, 1% v/v Triton X-100, 100 ug/ml aprotinin. The total protein concentration of the lysates was assayed with the BCA Protein Assay kit (Pierce; Rockford, Ill., USA) which uses BSA as the protein standard. 25 or 30 µg of each lysate was resolved by SDS-PAGE (7% w/v acylamide) then transblotted to Immobilon-P membrane (Millipore, Bedford, Massachusettes). Non-specific binding sites were blocked with 5% w/v skim milk powder then the filter probed with rabbit polyclonal IgG recognizing the β-subunit of IGF-1R protein (C-20; Santa Cruz Biotechnology Inc., Santa Cruz, Calif., USA). The IGF-1R-specific signal was developed using the ECF western blotting kit (Amersham, Buckinghamshire, England, UK) and detected by chemifluorescence and phosphoimager scanning followed by quantification with ImageQuant software (Molecular Dynamics, Sunnyvale, Calif., USA). Inter-filter variation was controlled for by standardising signal intensities against the mean signal for cells treated with GSV alone.

Cell Proliferation Assay

Cells were grown to 40% confluence in 24-well plates and transfected every 24 h for up to 3 days. Cell number was determined at 0, 24, 48 and 72 h using an amido black binding protocol in which binding of amido black to cellular protein (quantitated spectrophotometrically) correlates with cell number (Schultz et al., *J. Immunol. Methods* 167: 1-13, 1994). Briefly, cell monolayers were fixed with 1% v/v glutaraldehyde in PBS then stained with 0.1% w/v amido black in Na acetate at pH 3.5 for 30 min. After a single wash in acidic $H_2O$, the protein-bound dye was eluted with NaOH (50 mM) and the absorbance of the eluate monitored at 620 nm. Data are expressed relative to the signal determined for GSV-treated cells at 0 h.

IGF-1R mRNA

Figure 4A:
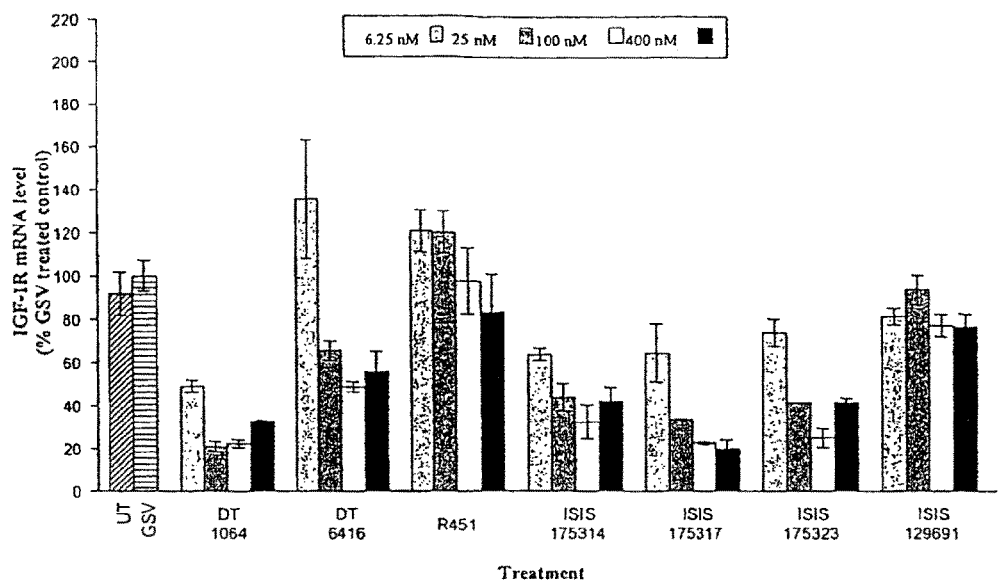
Figure 4B:
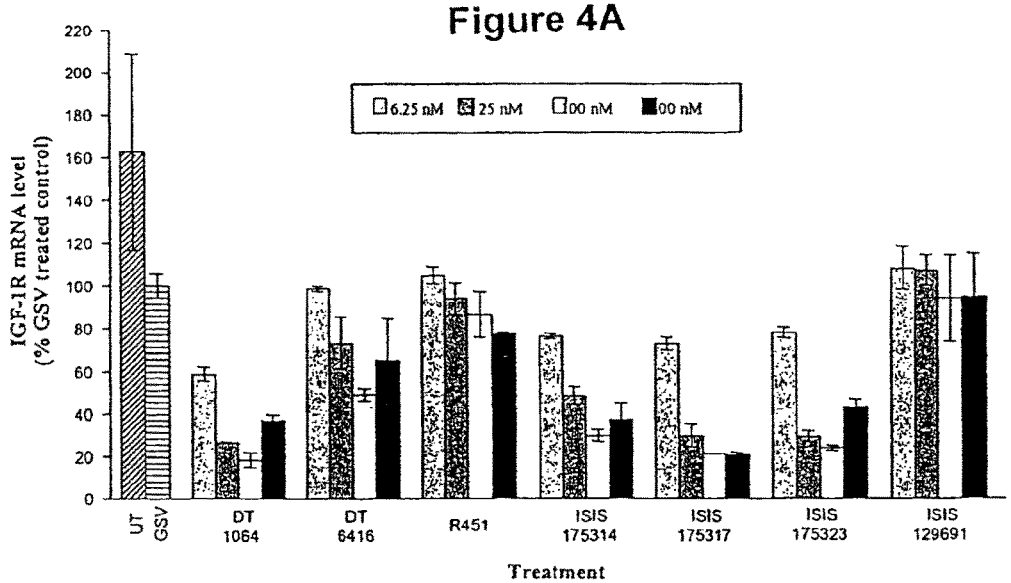

FIG. 4 shows the IGF-1R real-time PCR data for HaCaT keratinocytes treated with C5-propynes or 2' MOE gapmers. The results were similar whether cells were transfected once (FIG. 4A), or twice (FIG. 4B). IGF-1R mRNA levels were lower in cells transfected with DT1064, in keeping with levels reported previously using RNase protection assays [Fogarty et al, 2002, supra]. All three lead ASOs also caused knockdown of IGF-1R mRNA. Furthermore, knockdown of the IGF-1R mRNA was similar for the three ASO leads and DT1064. For example, in FIG. 4A, at 100 nM ASO, the average reduction in mRNA was 68%, 77%, 75% and 78% for ASO 175314, ASO 175317, ASO 175323 and DT1064, respectively.

IGF-1R Protein

Figure 5A:
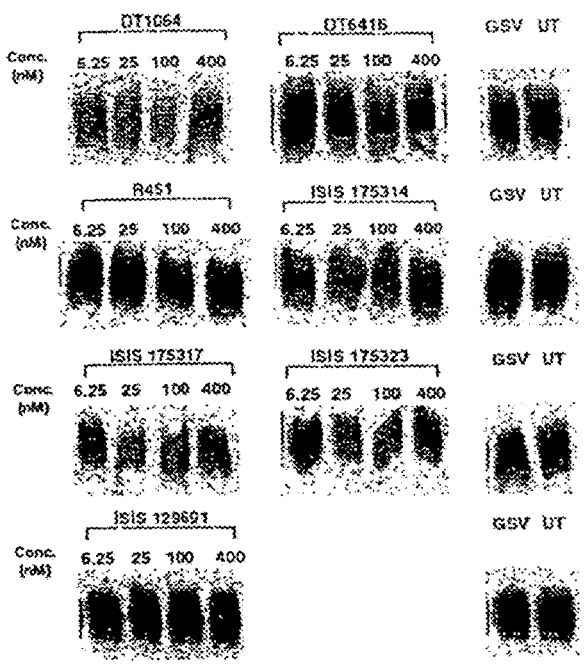

FIG. 5A shows a representative IGF-I receptor western immunoblot of HaCaT cells transfected with C5 propynes or 2' MOE gapmers. The IGF-IR protein (β chain) appears as a single band of molecular weight 110 kD.

Figure 5B:
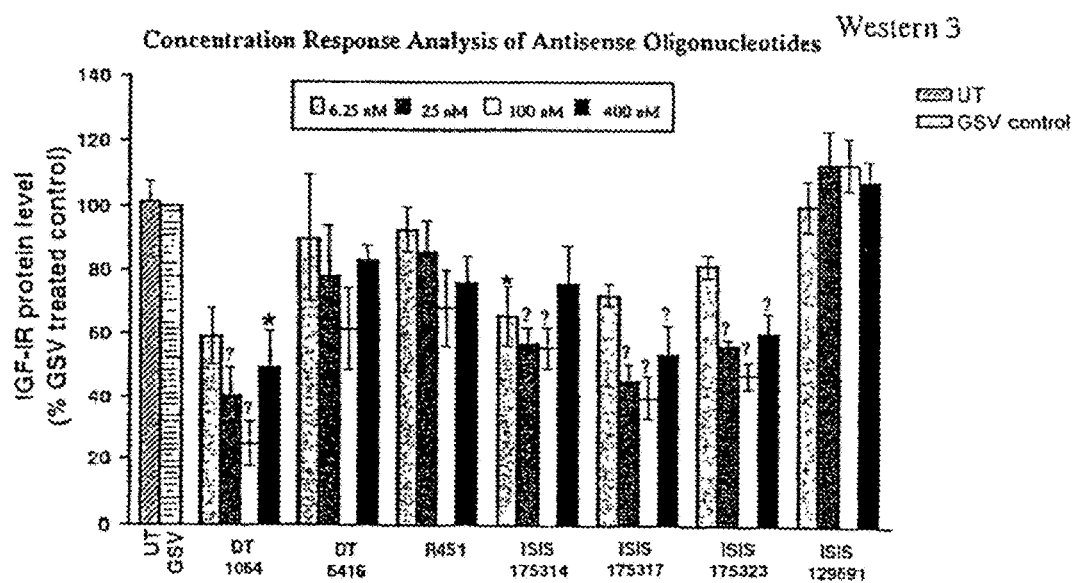

The band intensities (expressed relative to cells treated with GSV alone) from three separate experiments are combined and presented in FIG. 5B. The data show that DT1064 potently suppressed levels of IGF-IR protein as shown previously (Fogarty et al., 2002, supra). Relative to cells treated with GSV alone, all three lead ASOs significantly reduced IGF-IR protein at 25 nM and 100 nM (P<0.01). ISIS 175317 and ISIS 175323, but not ISIS 175314, knocked down IGF-IR protein at the 400 nM concentration (P<0.01). There was no significant knockdown of IGF-IR protein with ISIS 175317 or ISIS 175323 at the lowest concentration, 6.25 nM.

Relative to the GSV control, transfection of HaCaT cells with DT1064 provided apparent maximal reduction of 75% when cells were treated at a concentration of 100 nM, while IGF-IR protein levels with ISIS 175317 was approximately 60%. The knockdown of IGF-IR protein associated with each of the ASOs is expressed as a percentage of its appropriate control. This show that the ability of the ASOs to knockdown target protein is comparable to that of DT1064 (see Table 3).

TABLE 3

IGF-IR protein knockdown with ASOs expressed as a percentage of control olignonucleotides of the same chemistry at the same concentration.

|  | 6.25 nM | 25 nM | 100 nM | 400 nM |
|---|---|---|---|---|
| DT1064 (relative to 6416) | 34 | 48 | 59 | 41 |
| DT1064 (relative to R451) | 36 | 53 | 64 | 35 |
| ISIS 175314 | 35 | 57** | 51** | 30 |
| ISIS 175317 | 28 | 60*** | 65*** | 50** |
| ISIS 175323 | 19 | 50*** | 58*** | 44** |

*$P < 0.5$,
**$P < 0.01$,
***$P < 0.001$ versus IGF-1R protein in HaCaT cells transfected with oligonucleotide of the same chemistry and dose; Tukey's test.

Cell Proliferation

The effect of IGF-1R-specific ASOs and control oligonucleotides on HaCaT proliferation is shown in FIG. 6. In untreated cells, keratinocyte cell numbers increased more than four-fold over three days. GSV-treated cells also increased in number though not to the same extent as untreated cells (64% of untreated at 72 h) suggesting some effect of the lipid on proliferation rates. Relative to untreated and GSV-treated cells, all cells treated with oligonucleotides showed lower rates of cell proliferation over the 3 days, with DT1064-treated cells having the lowest rates of cell proliferation at all time-points and at all concentrations of oligonucleotide. Of the ASOs tested, there was a trend for ISIS 175317 to be associated with the lowest rates of cell proliferation most notably at the 400 nM concentration.

Three IGF-OR lead ASOs have been tested in the HaCaT keratinocyte transfection system at MCRI. The major findings are:

All three ASO leads reduced IGF-IR mRNA levels compared with the GSV control and the 2' MOE gapmer random oligonucleotide. Relative to DT1064, the ASO leads gave a similar reduction in IGF-IR mRNA.

All three ASO leads significantly reduced IGF-IR protein relative to the GSV control and the 2' MOE random oligonucleotide. The ASO leads reduced IGF-IR protein levels. However, when expressed as a percentage of knock-down relative to control oligonucleotides of the same chemistry, the effect of the ASO leads was similar to that of DT1064.

All three ASO leads reduced cell proliferation rates relative to the GSV control.

Ex Vivo Maintenance of Psoriatic Skin Biopsies

Biopsies were maintained for 24 hrs as described previously (Russo et al., *Endocrinology* 135: 1437-1446, 1994; White et al., 2002, supra). Briefly, subcutaneous fat was removed from the biopsies before they were placed, dermis down, on a BACTO (trademark) agar plug (Becton Dickinson, Franklin Lakes, USA) formed in the middle of a triangular stainless steel mesh. The steel mesh was designed to fit the centre well of a 60 mm FALCON (registered trademark) centre-well organ culture dish (Becton Dickinson) so that the agar plug was suspended over the centre well. The centre well was filled with Dulbecco's modified Eagle's medium (containing 10% w/v foetal calf serum, 50 IU/ml penicillin, 50 ug/ml streptomycin) to the level of the agar plug and the outer well filled with PBS to maintain humidity. Biopsies were incubated at 37° C. in an atmosphere of 5% v/v $CO_2$. FIG. 1 shows the tissue apparatus arrangement.

Example 19

Comparison of Direct Fluorescence Microscopy and Immunohistochemistry for Detection of ASOs The 2' MOE FITC-ASO ISIS 251741 was formulated at 0.1% w/w in 5% w/v methylcellulose and applied topically to psoriatic skin biopsies. Both direct fluorescence and immunohistochemistry with the 2E1 antibody can detect ISIS 251741. This characteristic allowed the use of adjacent sections to directly compare ASO localization as determined by the two detection technologies.

Both detection methods show a remarkably similar distribution of ASO. Both methods show accumulation of ASO in basal keratinocytes, exclusion of ASO from the nuclei of most keratinocytes of the stratum granulosum, and ASO in the nuclei of cells that appear to be invading leukocytes located in the dermis. Accumulation of ASO in the stratum corneum is apparent using both detection methods.

These results indicate that both direct fluorescence and immunohistochemistry are viable methods for the detection of ASO in skin, however, both methodologies have their strengths and weaknesses. Digestion of skin sections with proteinase K (required before immunohistochemistry) often resulted in degradation of tissue morphology. Immunohistochemical detection of ASOs is also limited to ASOs of specific chemistry (phosphorothioate) and nucleotide sequence (TGC or GC motifs) whereas any ASO can be conjugated to FITC. Furthermore, immunohistochemical detection of ASO appeared to be more variable that detection of ASO by direct fluorescence. However, immunohistochemicaly stained sections can be stored and referred too for a longer period of time than fluorescent sections, which fade over time. In addition, there is lack of data concerning the effects of FITC conjugation on the physicochemical properties of ASOs.

Example 20

Effect of FITC Conjugation on Epidermal Localization of ASOs Following Topical Application In order to determine whether an FITC tag attached to an ASO alters epidermal localization of the ASO following topical application, biopsies were treated with an ASO mixture containing the non-FITC-ASO ISIS 13920 (detectable by immunohistochemistry but not direct fluorescence) and the FITC-ASO ISIS 147979 (detectable by direct fluorescence but not immunohistochemistry). Comparison of serial sections from tissues treated with this mixture showed no apparent difference between the localization of the two ASOs. This data indicates that in psoriatic skin biopsies, an FITC tag on an ASO does not alter epidermal localization.

In order to control for the possibility that the FITC-ASO may effect the epidermal localization of ISIS 13920, biopsies were treated with 0.1% w/v ISIS 13920 alone. As can be seen, immunohistochemical detection of ISIS 13920 demonstrates a pattern of ASO distribution not apparently different to that seen for ASO 13920 mixed with ISIS 147979.

The localization of topically applied 2' MOE ASOs in the epidermis of psoriatic skin lesions was investigated and compared with C5-propyne ASOs. The major findings are:

Topically applied 2' MOE gapmer ASOs in either 5% w/v methylcellulose or cream were able to cross the stratum corneum of psoriatic skin lesions. ASOs localized to the nuclei of basal keratinocytes in the epidermis and invading leukocytes in the dermis.

Epidermal localization following topical application does not appear to differ between 2' MOE gapmer and C5-propyne ASOs.

Following topical application, 2' MOE gapmer ASOs can be detected in the nuclei of basal keratinocytes by both direct fluorescence microscopy (FITC conjugated ASOs only) and by immunohistochemistry with the 2E1 Ab.

FITC conjugation of ASOs does not appear to alter their ability to reach basal keratinocytes or their epidermal localisation following topical application.

Example 21

Drug Formulation

Lyophilized ASOs were resuspended in sterile, distilled water and the concentration of ASO determined by its optical density at 260 nm before formulation in either a 5% w/v methylcellulose gel or in a cream (Isis Pharmaceuticals). The cream contained:
isopropyl myristate (10% w/w)
glyceryl monostearate (10% w/w)
polyoxyl 40 stearate (15% w/w)
hydroxypropyl methylcellulose (0.5% w/w)
monobasic sodium phosphate monohydrate (0.3% w/w)
dibasic sodium phosphate heptahydrate (0.9% w/w)
phenoxyethanol (2.5% w/w)
methylparaben (0.5% w/w)
propylparaben (0.5% w/w)
purified water (59.8% w/w)

For formulation in 5% w/v methylcellulose, 10% w/v methylcellulose (in PBS) was diluted two-fold with PBS containing ASOs at twice the desired final concentration.

For formulation in cream, ASOs were dried (DNA Mini vacuum drier, Medos company, Melbourne, Australia) and then dissolved in an appropriate amount of cream to give the desired final concentration.

Example 22

Drug application

Approximately 30 min after biopsies were transferred to 37° C., ASOs or vehicle were weighed out (30 mg) and applied directly to an approximately 4 mm diameter central region of biopsies with a small spatula. A thin ring around the edge of the biopsy was kept free of ASO or vehicle in order to avoid application of ASO to the exposed edge of the sample. Despite these precautions, in approximately 20% of biopsies ASOs appeared to have been in contact with the edges of the biopsy as assessed by direct fluorescence microscopy.

Example 23

Experimental Groups

Pursuant of the aims of this Example, ASO formulations were applied to at least four biopsies from different individuals. The ASO formulations and controls used were:
0.1% w/w R451 in 5% methylcellulose
0.1% w/w ISIS 251741 in 5% w/v methylcellulose
0.1% w/w ISIS 251741 in cream
0.1% w/w ISIS 251741 mixed with 4.9% w/2 ASO 13920 in cream
0.1% w/w ISIS 13920 in 5% w/v methylcellulose
0.1% w/w ISIS 147979 mixed with 0.1% w/w ASO 13920 in 5% v/v methylcellulose
0.1% w/w ISIS 147979 in 5% w/v methylcellulose
5% w/v methylcellulose alone.
Cream alone.

Example 24

Benchmarking for ISIS 175317 and DT1064

This Example shows the benchmarking of human IGF-IR identified in a primary screen against IGF-IR ASO (ISIS 175317) and DT1064 in HaCaT Keratinocytes.

IGF-IR mRNA levels were measured by real-time PCR after overnight transfection of HaCaT keratinocytes with IGF-IR ASOs and control oligonucleotides. The results show that the four new leads, as well as ISIS 175317 and DT1064, potently inhibited IGF-IR mRNA levels in a concentration-dependent and sequence-specific manner. Relative to HaCaT cells treated with the transfection reagent alone, none of the four recently-identified IGF-IR ASOs suppressed IGF-IR mRNA levels with any greater potency or efficacy than ISIS 175317.

Oligonucleotides

TABLE 5

List of the oligonucleotides used for in vitro testing

|   | Chemistry | Identification | Antisense/Control |
|---|---|---|---|
| 1 | 2'-O-(2-methoxy)ethyl | ISIS 175317 | A |
| 2 | 5,10,5-gapmer, | ISIS 323737 | A |
| 3 | phosphorothioate throughout | ISIS 323744 | A |
| 4 | All cytosine bases methylated | ISIS 323762 | A |
| 5 | (Abbreviation: 2' MOE gapmer) | ISIS 323767 | A |
| 6 |  | ISIS 306064 | C (8 nucleotide mismatch for ISIS 175317) |
| 7 |  | ISIS 129691 | C (random) |
| 8 | C5-propynyl-dU,dC-phosphorothioate | DT1064 | A |
| 9 | (Abbreviation: C5-propyne) | DT6416 | C (15 nucleotide mismatch for DT1064) |

The concentration of each oligonucleotide was confirmed by its UV absorbance at 260 nm prior to use.

Transfection of Keratinocytes with Antisense Oligonucleotides

HaCaT keratinocytes were maintained as monolayer cultures in Dulbecco's modified Eagle's medium (DMEM) supplemented with 10% v/v foetal calf serum (FCS) at 37° C. in an atmosphere of 5% V/V $CO_2$/95% V/V $O_2$.

HaCaT keratinocytes [passage number 62 and 63 (FIG. 8) and 45 (FIG. 10)] were seeded into the wells of 96-well plates. 85-95% confluent cells were treated with the liposome preparation, Cytofectin GSV alone, or complexed with antisense or control oligonucleotides for 20 h. Untreated cells were also studied (untreated control). Each antisense or control oligonucleotide (20× final concentration) in serum-free DMEM was mixed with an equal volume of GSV (20× final concentration; 40 μg/ml). Lipid/oligonucleotide mixtures were allowed to complex at room temperature for 10-15 min then diluted ten-fold with DMEM containing 10% v/v FCS. Cells were transfected with oligonucleotide (final concentration range, 0.4 to 200 nM) and 2 μg/ml GSV. Transfections were performed in duplicate wells, while untreated and GSV-treated cells were run in four and six replicate wells, respectively.

IGF-I Receptor mRNA Levels

Total RNA was extracted using a RNeasy® Mini kit (Qiagen Inc., Valencia, Calif., USA) and approximately 0.1 to 0.2 μg were reverse transcribed using the GeneAmp® RNA PCR kit (Applied Biosystems, Foster City, Calif., USA), according to the manufacturer's instructions. Semi-quantitative real-time PCR was used to determine the amount of IGF-I receptor mRNA in the sample relative to cells treated with Cytofectin GSV alone. Pre-developed reagents for the human IGF-I receptor (Applied Biosystems, product no. 4319442F) and 18S ribosomal RNA (Product no. 4319413E) containing primers and TaqMan (Reg. Trademark) fluorescent probes were used in a multiplex PCR reaction to simultaneously amplify both products in each sample. An ABI Prism™ 7700 sequence detector (Applied Biosystems) was used for the analysis. IGF-I receptor mRNA levels were then normalised to 18S ribosomal RNA.

Biological Effects

The effect of antisense and control oligonucleotides on IGF-IR mRNA levels were initially studied at concentrations of 6, 13, 25, 50, 100 and 200 nM. These concentrations were chosen because they covered a range that would allow a comparison of data with previous in vitro benchmarking experiments using 2'MOE gapmers in HaCaT keratinocytes.

FIG. 8 shows the IGF-I receptor mRNA levels for two experiments in which HaCaT keratinocytes were transfected with 2' MOE gapmers (ISIS 175317, ISIS 323737, ISIS 323744, ISIS 323762, ISIS 323767, ISIS 129691 or ISIS 306064) or C5-proynes oligonucleotides (DT1064 or 6416). Relative to GSV-treated cells, all five 2'MOE gapmer ASOs potently suppressed IGF-IR mRNA levels (FIG. 9). Maximal target knockdown was similar for each 2'MOE ASO (range 71-77%). Table 6 shows the maximum efficacy of the IGF-IR ASO leads.

In contrast, IGF-IR mRNA levels for the two 2'MOE gapmer control oligonucleotides (ISIS 129691 and ISIS 306064) were similar to the levels of the GSV-treated cells, indicating that the effect of the 2'MOE gapmer ASOs on IGF-IR mRNA levels was sequence-specific (FIG. 8). The effect of DT1064 on IGF-IR suppression was maximal at 77% at 100 nM. However, transfection of HaCaT cells with the C-5 propyne mismatch control oligonucleotide (6416) also suppressed IGF-IR mRNA levels by up to 46% at the same concentration. This is consistent with previous data.

Since maximal or near-maximal suppression of IGF-IR mRNA levels was seen with the ASOs in the concentration range from 25 to 200 nM it was difficult to discriminate between the efficacy of the five 2'MOE ASOs. Therefore it was decided to test their effect at lower concentrations. FIG. 10 shows IGF-IR

TABLE 6

Maximum efficacy of ISIS IGF-IR ASO leads

| 2' MOE gapmer IGF-1R ASO | IGF-IR mRNA levels (% cytofectin GSV-treated cells) |
|---|---|
| ISIS 323762 | 23.1 |
| ISIS 323767 | 24.3 |
| ISIS 175317 | 26.8 |
| ISIS 323737 | 27.5 |
| ISIS 323744 | 29.5 |

Figure 2B:
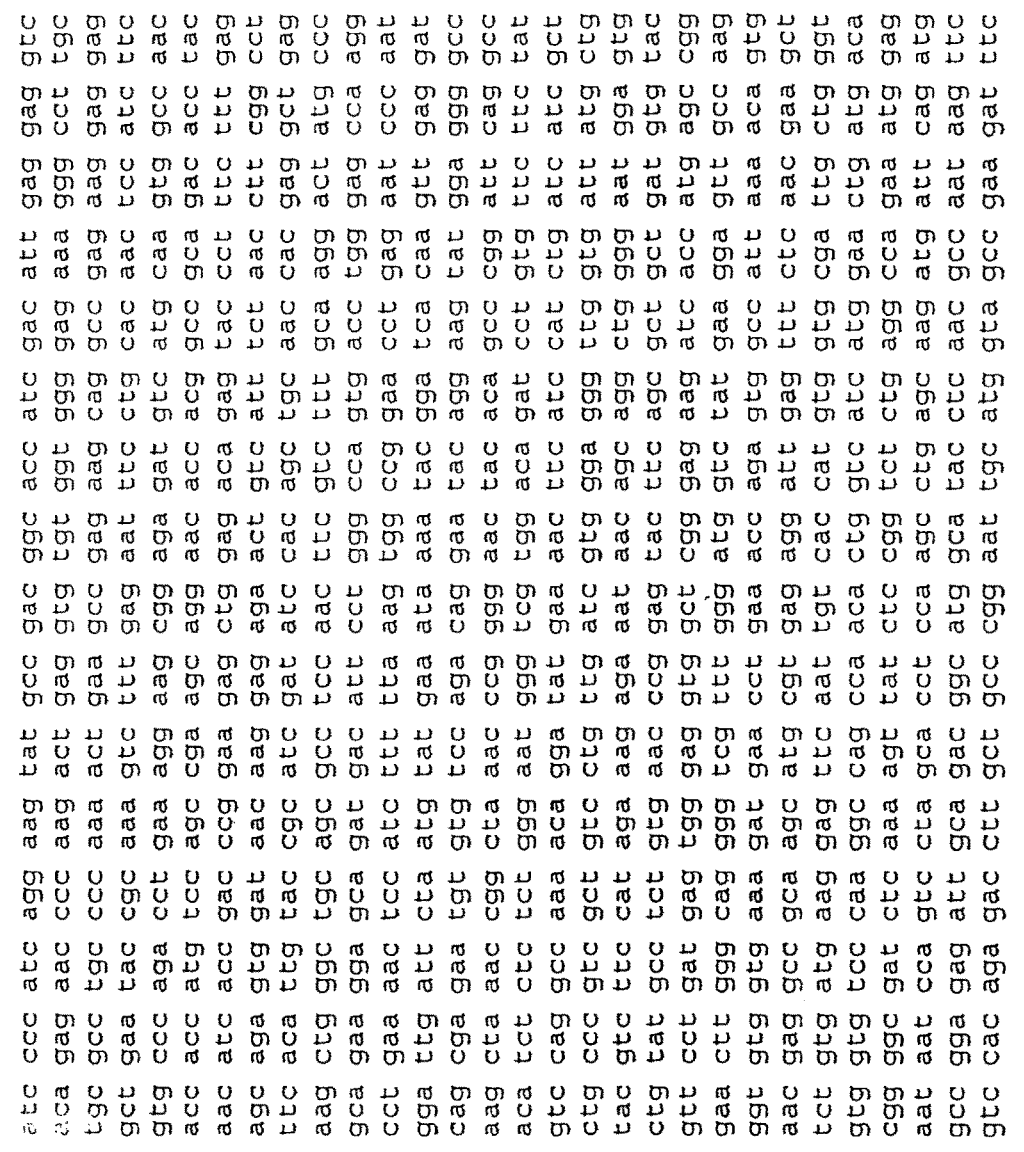

Calculated from maximum efficacy IGF-IR mRNA levels (% of cytofectin GSV-treated cells) reported in FIG. 2.

mRNA levels from a single experiment in which HaCaT cells were treated with oligonucleotides at 0.4, 1.6, 3, 6, 25, or 100 nM. As in the earlier experiments at the higher concentrations, all five 2'MOE ASOs specifically suppressed IGF-IR mRNA levels, and did so with similar potency. The maximal inhibition of IGF-IR mRNA was 87% for ISIS 175317, similar to that of the recently identified 2'MOE gapmer ASOs (range 79-85% of GSV). The response to ASO treatment was concentration dependent in this range. Treatment of HaCaT keratinocytes with 25 nM DT1064 suppressed IGF-IR mRNA levels by 81%, similar to the 2'MOE gapmer ASOs.

FIG. 11 shows the concentration-response curves for the IGF-IR targeted 2'MOE ASOs (same data as FIG. 10). With the possible exception of ISIS 323767, these data indicate similar potencies of ISIS 175317 and the 2'MOE gapmers. This is reflected in the $EC_{50}$ calculated from the concentration-response curves and listed in Table 7. The $EC_{50}$ for DT1064 was 3.2 nM (C.I. 2.1-4.7). It is important to note that the $EC_{50}$ values presented in Table 7 were calculated from a single experiment and are given as an estimate only. Additional concentration-response experiments would be required to give a more accurate estimate of the $EC_{50}$ values for the ASOs.

TABLE 7

Mean $EC_{50}$ (95% confidence intervals) for 2'MOE gapmer ASO suppression of IGF-IR mRNA levels in HaCaT keratinocytes

| 2'MOE gapmer ASO | $EC_{50}$ [nM] |
|---|---|
| ISIS 175317 | 2.6 (1.8-3.6) |
| ISIS 323744 | 2.8 (2.2-3.6) |
| ISIS 323737 | 3.2 (0.4-25.8) |
| ISIS 323762 | 3.3 (2.4-4.3) |
| ISIS 323767 | 4.2 (2.4-7.4) |

The concentration response experiments reported here were performed twice at the higher concentration range and showed no difference in maximum efficacy (Table 6). The concentration response experiment was performed once at the lower concentration range. Across all of the concentrations studied (0.4 to 200 nM), none of the four leads used in this Example appeared to exhibit greater IGF-IR mRNA knockdown than ISIS 175317 in HaCaT keratinocytes (FIGS. 9 and 11). Examination of the concentration-response curves showed similar potency between ISIS 175317 and the four leads as assessed by $EC_{50}$ (FIG. 11).

Antisense Oligonucleotide

Details of the IGF-IR ASO used in this Example are provided in Table 5. The underline nucleotides are 2'MOE modifications. All cytosine bases are methylated.

TABLE 5

IGF-IR ASO

| Chemistry | Identification | Sequence |
|---|---|---|
| 2'MOE gapmer, phosphorothioate throughout | ISIS 175317 (SEQ ID NO: 125) | <u>CGAAG</u>GAAACAATAC<u>TCCGA</u> |

ISIS 175317 (SEQ ID NO:125) was manufactured to research-grade quality by Isis Pharmaceuticals, California, USA.

Collection of Psoriatic Skin Biopsies

Psoriatic skin biopsies were collected from eleven volunteers under ehtical conditions (Protocol 22023A of the Royal Children's Hospital Ethics in Human Research Committee, Melbourne, Australia). Three 8 mm, full thickness, punch biopsies were collected from the same lesion in each volunteer by a dermatologist. The area from which the biopsies were taken was not cleaned or disinfected prior to biopsy collection. Biopsies were immediately plcated on guaze (wet with PBS) and stored on ice until used (~2h). At the time of collection, the severity of psoriasis in the biopsies was scored using the PRS (parameter rating scale) component of the PASI (psoriasis area severity index) score (Fredriksson et al., 1978 supra). In brief, ertherma (redness), induration (swelling) and desquanmation (flaking) were each scored from 0 (absent) to 4 (severe) to give a PRS score of 0 to 12.

Ex Vivo Maintenance of Psoriatic Skin Biopsies

Biopsies were maintained for 24 h as previously described (Russo et al., 1994 supra; White et al., 2002 supra). Briefly, subcutaneous fat was removed from the biopsies and they were then placed, dermis down, on a BACTO™ agar plug (Becton Dickinson, Franlin Lakes, USA) formed in the middle of a triangular stainless steel mesh. The steel mesh was designed to fit the center well of a 60 mm FALCON (Reg. Trademark) center-well organ culture dish (Becton Dickinson) so that the agar plug was suspended over the center well. The center well was filled with Dulbecco's modified Eagles medium (containing 10$ v/v foetal calf serum, 501 U/ml penicillin, 50 ug/ml streptomycin) to the level of the agar plug and the outer well was filled with PBS to maintain humidity. Biopsies were incubated at 37° C. in an atmosphere of 5% v/v $CO_2$. The tissue apparatus arrangement is shown in FIG. 1.

Drug Formulation

Lyophilised ISIS 175317 (SEQ ID NO:125) was resuspended in sterile distilled water and the concentration of the solution was determined by its optical density at 260 nm. For formulation in cream, ASO's were dried (DNA Mini vacuum drier, Medos Company, Melbourne, Australia) then dissolved in an appropriate amount of cream (Isis Pharmaceuticals, USA) to give a final concentration of 10% w/w. The cream contained:

isopropyl myristate (10% w/w)
pehnoxyethanol (2.5% w/w)
glyceryl monostearate (10% w/w)
methylparaben (0.5% w/w)
polyoxyl 40 stearate (15% w/w)
propylparaben (0.5% w/w)
hydroxypropyl methylcellulose (0.5% w/w)
purified water (59.8% w/w)
monobasic sodium phosphate monohydrate (0.3$ w/w)
dibasic sodium phosphate heptahydrate (0.9% 2/2)

Drug Application

After a 30-minute pre-incubation of the biopsy at 37° C., 30 mg of pre-weighed drug or vehicle was applied directly to an approximately 4 mm diameter central region of each biopsy with a small spatula. A thin ring around the edge of the biopsy was kept free of ISIS 175317 (SEQ ID NO:125) or vehicle in order to avoid the cream touching the exposed edge of the sample. Previous studies in this laboratory using FIT-CASOs applied in this way, have shown that in approximately 20% of cases, ASOs contact the edges of the biopsy.

Experimental Groups

Three biopsies were collected from each volunteer. One of the biopsies was treated with vehicle (Isis cream) and the other two with 10% ISIS 175317 (SEQ ID NO: 125) in the cream. This treatment regimen allows paired (vehicle-treated biopsy paired to the average of the two ISIS 175317 (SEQ ID NO: 125)-treated biopsies) analysis of the data, and control for possible confounding effects caused by inter-subject variations in IGF-IR mRNA levels. Two biopsies from each patient were treated with ISIS 175317 (SEQ ID NO: 125) to increase the likelihood of detecting any drug effect.

Separation of Epidermis from Dermis

At the end of the treatment period (24 h), tissue samples were incubated in 0.5 M EDTA (pH 7.4) at 60° C. for 90 sec to disrupt the epidermal-dermal junction and allow separation of the epidermis and dermis by blunt dissection (Dusserre et al., 1992 supra). The separated epidermis and dermis were snap frozen in liquid nitrogen and stored at −70° C. until the RNA was extracted.

Measurement of IGF-IR mRNA Levels by Real-Time PCR

Tissues were mechanically crushed in a stainless steel mortar and pestle that had been chilled in liquid nitrogen. Total RNA was extracted using a Rneasy (Reg. Trademark) Mini kit (Qiagen Inc., Valencia, Calif., USA). Total RNA (100 to 700 ng) was reverse transcribed using the GeneAmp RNA PCR kit (Applied Biosystems, Foster City, Calif., USA), according to the manufacturer's instructions. The amount of starting RNA was matched as closely as practicable for each set of biopsies and all samples were reverse-transcribed in the same reaction. Semi-quantitative real-time PCR was used to determine the amount of IGF-IR mRNA in biopsies relative to 18S RNA. Pre-developed reagents for human IGF-IR (Applied Biosystems, product no. 4319442F) and 18S (product no. 4319413E) containing primers and TaqMan (Reg. Trademark) fluorescent probes were used in a multiplex PCR reaction to simultaneously amplify both products in each sample. Each sample was assayed in duplicate. An ABI Prism 7700 sequence detector (Applied Biosystems) was used for the analysis. IGF-IR mRNA levels were normalised to 18S.

Statistical Analysis

For statistical analysis, biopsies from each individual were paired. Each vehicletreated biopsy was paired to the average of the two ISIS 175317 (SEQ ID NO:125)-treated biopsies. For comparison of IGF-IR mRNA levels in ISIS 175317 (SEQ ID NO:125)-treated and vehicle-treated biopsies, a parametric paired t-test was used. This test assumes that the underlying population has a Gaussian distribution. These data did not differ significantly ($P>0.1$) from that expected if sampling was from a population with a Gaussian distribution as assessed by a modified Kolmogorov-Smirnov test (Dallal et al., 1986 supra). Furthermore, dot plots of the differences in IGF-IR mRNA levels between vehicle and ISIS 175317 (SEQ ID NO: 125) treated biopsies appeared to be from a population with a Gaussian distribution. For all other comparisons, the non-parametric Wilcoxon matched pairs test was used. This test makes no assumptions about the underlying population distribution. Statistical analysis was performed using GraphPad Prism version 3.00 for Windows (GraphPad Software, San Diego, Calif. USA). All data are presented as mean±one standard deviation.

Measurement of IGF-IR, GAPDH, HPRT, Insulin Receptor (IR), Caspase 3 & Bax mRNA Levels by Real-Time PCR Tissues were mechanically crushed in a stainless steel mortar and pestle that had been chilled in liquid nitrogen. Total RNA was extracted using a Rneasy (Reg. Trademark) Mini kit (Qiagen Inc., Valencia, Calif., USA). Total RNA (100 to 700 ng) was reverse transcribed using the GeneAmp (Reg. Trademark). RNA PCR kit (Applied Biosystems, Foster City, Calif., USA), according to the manufacturer's instructions. The amount of starting RNA was matched as closely as practicable for each set of biopsies and all samples were reverse-transcribed in the same reaction.

Semi-quantitative real-time PCR was used to determine the amount of IGF-IR, GAPDH, HPRT, Insulin receptor (IR), Caspase 3 & Bax mRNA in biopsies relative to 18S RNA. Pre-developed reagents for the above mentioned genes (Applied Biosystems, product # 4319442F (IGF-IR), # 433764F (GAPDH), # 4333768F (HPRT), # 4318283F (Bax) and Applied Biosystems 'assay-on-demand' assay ID # Hs00263337_m1 (Caspase 3) and # Hs00169631_m1 (Insulin receptor)) were each individually used in a multiplex PCR reaction with a pre-developed reagent for 18S (Applied Biosystems, product no. 4319413E). These pre-developed reagents contained primers and TaqMan (Reg. Trademark) fluorescent probes and, when used in a multiplex PCR reaction, simultaneously amplified the target gene (IGF-IR, GAPDH, HPRT, Insulin receptor (IR), Caspase 3 or Bax) and 18S in each sample. Each sample was assayed in duplicate. An ABI Prism™ 7700 sequence detector (Applied Biosystems) was used for the analysis. IGF-IR, GAPDH, HPRT, Insulin receptor (IR), Caspase 3 and Bax mRNA levels were normalised to 18S.

Statistical Analysis

For statistical analysis, biopsies from each individual were paired. Each vehicle-treated biopsy was paired to the average of the two ISIS 175317 (SEQ ID NO: 125)-treated biopsies.

For comparison of the gene of interest's mRNA levels in ISIS 175317 (SEQ ID NO: 125)-treated and vehicle-treated biopsies, a parametric paired t-test was used. This test assumes that the underlying population has a Gaussian distribution. These data did not differ significantly ($P>0.1$) from that expected if sampling was from a population with a Gaussian distribution as assessed by a modified Kolmogorov-Smirnov test (Dallal et al., 1986). Furthermore, dot plots of the differences in the gene of interest's mRNA levels between vehicle and ISIS 175317 (SEQ ID NO: 125) treated biopsies appeared to be from a population with a Gaussian distribution.

Statistical analysis was performed using GraphPad Prism version 3.00 for Windows (GraphPad Software, San Diego, Calif. USA). All data is presented as mean±one standard deviation).

The results are shown in FIGS. 12 to 14 and clearly demonstrate the efficacy of the ISIS 175317 (SEQ ID NO:125) ASO in the cream to reduce IGF-IR and RNA in normal epiderms, dermis and psoriatic epidermis. The results in FIG. 14 clearly demonstrate the specificity of this ASO for IGF-IR.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

bibliography

Boukamp et al., *J. Cell Biol.* 106: 761-771, 1988;
Camacho-Hubner et al., *J. Biol. Chem.* 267: 11949-11956, 1992;
Clemmons, *Growth Regn.* 2:80, 1992;
Flanagan and Wagner, *Mol. Cell. Biochem.* 172: 213-225, 1997;
Flanagan et al., *Nat. Biotechnol.* 14: 1139-1145, 1996b;
Flanagan et al., *Nucleic Acids Res.* 24: 2936-2941, 1996a;
Fogarty et al., *Antisense Nucleic Acid Drug Development* 12: 369-377, 2002;
Fredriksson et al., *Dermatologica* 157: 238-244, 1978;
Hodak et al., *J. Invest. Dermatol.* 106: 564-570, 1996;
Jensen et al., *Br. J. Dermatol.* 139: 984-991, 1998;
Krane et al., *J. Exp. Med.* 175: 1081-1090, 1992;
Krane et al., *J. Invest. Dermatol.* 96: 419-424, 1991;
LeRoith et al., *Endocr. Rev.* 16: 143-163, 1995;
Mehta et al., *J. Invest. Dermatol.* 115: 805-812, 2000;
Neely et al., *J. Inv. Derm.* 96: 104, 1991;
Neely et al., *J. Invest. Dermatol.* 96: 104-110, 1991;
Oakes et al., *J. Clin. Endocrinol. Metab.* 73: 1368-1373, 1992
Pietrzkowski et al., *Mol. Cell. Biol.* 12: 3883-3889, 1992;
Porcu et al., *Mol. Cell. Biol.* 12: 5069-5077, 1992;
Rechler and Brown, *Growth Regulation* 2: 55-68, 1992;
Reiss et al., *Oncogene* 7: 2243-2248, 1992;
Resnicoff et al., *Cancer Res.* 54: 2218-2222, 1994;
Ristow and Messmer, *J. Cell Physiol.* 137: 277-284, 1988;
Ristow, *Dermatology* 195: 213-219, 1997;
Ristow, *Growth Regul.* 3: 129-137, 1993;
Rubin and Baserga, *Laboratory Investigation* 73: 311-331, 1995;
Russo et al., *Endocrinology* 135: 1437-1446, 1994;
Sara, *Physiological Reviews* 70: 591-614, 1990;
Schultz et al., *J. Immunol. Methods* 167: 1-13, 1994;
Ullrich et al., *EMBO J.* 5: 2503-2512, 1986;
van de Kerkhof, *Skin Pharmacol. Appl. Skin Physiol.* 11: 2-10, 1998;
White et al., *Antisense Nucleic Acid Drug Dev.* 10: 195-203, 2000;
White et al., *J. Invest. Dermatol.* 112: 887-892, 1999;
White et al., *Journal of Investigative Dermatology* 118: 1003-1007, 2002;
Wingens et al., *Lab Invest.* 79: 1415-1424, 1999;
Wraight et al., *J. Invest. Dermatol.* 103: 627-631, 1994;
Wraight et al., *J. Invest. Dermatol.* 108: 452-456, 1997;
Wraight et al., *Nat. Biotechnol.* 18: 521-526, 2000;
Xu et al., *J. Invest. Dermatol.* 106: 109-112, 1996;
Altschul et al., *J. Mol. Biol.* 215: 403-410, 1990;
Zhang and Madden, *Genome Res.* 7: 649-656, 1997;
Guo and Kempheus, *Cell* 81: 611-620, 1995;
Montgomery et al., *Proc. Natl. Acad. Sci. USA.* 95: 15502-15507, 1998;
Fire et al., *Nature* 391: 806-811, 1998;
Tijsterman et al., *Science,* 295; 694-697, 2002;
Timmons and Fire, *Nature* 395: 854, 1998;
Timmons et al., *Gene* 263: 103-112, 2001;
Tabara et al., *Science* 282: 430-431, 1998;
Montgomery et al., *Proc. Natl. Acad. Sci. USA* 95: 1998;
Tuschl et al., *Genes Dev.* 13: 3191-3197, 1999;
Elbashir et al., *Nature,* 411: 494-498, 2001;
Elbashir et al., *Genes Dev.* 15: 188-200, 2001;
Brazma and Vilo, *FEBS Lett.* 480: 17-24, 2000;
Celis et al., *FEBS Lett.* 480: 2-16, 2000;

Madden et al., *Drug Discov. Today* 5: 415-425, 2000;
Prashar and Weissman, *Methods Enzymol.* 303: 258-272, 1999;
Sutcliffe et al., *Proc. Natl. Acad. Sci. USA* 97: 1976-1981, 2000;
Jungblut et al., *Electrophoresis* 20: 2100-2110, 1999;
Fuchs et al., *Anal. Biochem.* 286: 91-98, 2000;
Larson et al., *Cytometry* 41: 203-208, 2000;
Jurecic and Belmont, *Curr. Opin. Microbiol.* 3: 316-321, 2000;
Carulli et al., *J. Cell Biochem. Suppl.* 31: 286-296, 1998;
Going and Gusterson, *Eur. J. Cancer* 35: 1895-1904, 1999;
To, *Comb. Chem. High Throughput Screen* 3: 235-241, 2000;
Nielsen et al., *Science* 254: 1497-1500, 1991;
Martin et al., *Helv. Chim. Acta*, 78: 486-504, 1995;
The Concise Encyclopedia Of Polymer Science And Engineering, pages 858-859,
Kroschwitz, J. I., ed. John Wiley & Sons, 1990;
Englisch et al., *Angewandte Chemie*, International Edition, 30: 613, 1991;
Sanghvi, Y. S., Chapter 15, *Antisense Research and Applications, pages* 289-302, Crooke,
S. T. and Lebleu, B., ed., CRC Press, 1993;
Scaringe, Ph.D. Thesis, University of Colorado, 1996;
Scaringe et al., *J. Am. Chem. Soc.* 120: 11820-11821; 1998;
Matteucci and Caruthers, *J. Am. Chem. Soc.* 103: 3185-3191, 1981;
Beaucage and Caruthers, *Tetrahedron Lett.* 22: 1859-1862, 1981;
Dahl et al., *Acta Chem. Scand.* 44: 639-641; 1990;
Reddy et al., *Tetrahedrom Lett.* 25: 4311-4314, 1994;
Wincott et al., *Nucleic Acids Res.* 23: 2677-2684, 1995;
Griffin et al., *Tetrahedron* 23: 2301-2313, 1967a;
Griffin et al., *Tetrahedron* 23: 2315-2331, 1967b;
Chiang et al., *J. Biol. Chem.* 266: 18162-18171, 1991;
Miura et al., *Clin. Chem.* 42: 1758-1764, 1996.

The invention claimed is:

1. A composition comprising an antisense compound consisting of a modified oligonucleotide consisting of 20 linked nucleosides and consisting of a nucleobase sequence recited in SEQ ID NO: 125, wherein said compound inhibits the expression of IGF-IR, and wherein said modified oligonucleotide consists of a ten deoxynucleotide region flanked on both the 5' and 3' end of said ten deoxynucleotide region with five 2'-O-(2-methoxyethoxy)nucleotides, wherein each internucleoside linkage in said modified oligonucleotide is a phosphorothioate linkage and each cytosine in said modified oligonucleotide is a 5-methylcytosine, said composition further comprising one or more pharmaceutically acceptable carriers and/or diluents.

2. A kit comprising the composition of claim 1 or an antisense compound consisting of a modified oligonucleotide consisting of 20 linked nucleosides and consisting of a nucleobase sequence recited in SEQ ID NO: 125, wherein said compound inhibits the expression of IGF-IR, and wherein said modified oligonucleotide consists of a ten deoxynucleotide region flanked on both the 5' and 3' end of said ten deoxynucleotide region with five 2'-O-(2-methoxyethoxy)nucleotides, wherein each internucleoside linkage in said modified oligonucleotide is a phosphorothioate linkage and each cytosine in said modified oligonucleotide is a 5-methylcytosine.

* * * * *

```
                            SEQUENCE LISTING

<160> NUMBER OF SEQ ID NOS: 171

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 1 cctttttattt gggatgaaat                                              20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 2
ccagacttca ttccttttat                                               20

<210> SEQ ID NO 3
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 3
tgatagtcgt tgcggatgtc                                               20

<210> SEQ ID NO 4
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 4
gctgctgata gtcgttgcgg                                               20

<210> SEQ ID NO 5
<211> LENGTH: 20
<212> TYPE: DNA
<213> ORGANISM: Artificial Sequence
```

```
<220> FEATURE:
<223> OTHER INFORMATION: antisense oligonucleotide

<400> SEQUENCE: 5
cttcagctgc tgatagtcgt                                               20

<210> SEQ ID NO 6
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 6
ccctcgatca ccgtgcagtt                                               20

<210> SEQ ID NO 7
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 7
ttggagatga gcaggatgtg                                               20

<210> SEQ ID NO 8
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 8
cggccttgga gatgagcagg                                               20

<210> SEQ ID NO 9
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 9
gtcctcggcc ttggagatga                                               20

<210> SEQ ID NO 10
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 10
cggtagtcct cggccttgga                                               20

<210> SEQ ID NO 11
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 11
ttgtagaaga gtttccagcc                                               20
```

```
<210> SEQ ID NO 12
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 12
tggtcatctc gaagatgacc                                              20

<210> SEQ ID NO 13
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 13
gagattggtc atctcgaaga                                              20

<210> SEQ ID NO 14
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 14
tccttgagat tggtcatctc                                              20

<210> SEQ ID NO 15
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 15
caatatcctt gagattggtc                                              20

<210> SEQ ID NO 16
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 16
aagcccaata tccttgagat                                              20

<210> SEQ ID NO 17
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 17
cccccgagta atgttcctca                                              20

<210> SEQ ID NO 18
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 18
```

-continued tctcaatcct gatggccccc                                              20

<210> SEQ ID NO 19
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 19
gttattggac accgcatcca                                              20

<210> SEQ ID NO 20
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 20
atgtagttat tggacaccgc                                              20

<210> SEQ ID NO 21
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 21
ccacaatgta gttattggac                                              20

<210> SEQ ID NO 22
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 22
cacaggtccc cacattcctt                                              20

<210> SEQ ID NO 23
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 23
ctggacacag gtccccacat                                              20

<210> SEQ ID NO 24
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 24
atggtggtct tctcacacat                                              20

<210> SEQ ID NO 25
<211> LENGTH: 20
<212> TYPE: DNA
<213> ORGANISM: Artificial Sequence

```
<220> FEATURE:
<223> OTHER INFORMATION: antisense oligonucleotide

<400> SEQUENCE: 25
tgttgatggt ggtcttctca                                              20

<210> SEQ ID NO 26
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 26
ctcattgttg atggtggtct                                              20

<210> SEQ ID NO 27
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 27
gttgtactca ttgttgatgg                                              20

<210> SEQ ID NO 28
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 28
cggtagttgt actcattgtt                                              20

<210> SEQ ID NO 29
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 29
agcagcggta gttgtactca                                              20

<210> SEQ ID NO 30
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 30
ggtccagcag cggtagttgt                                              20

<210> SEQ ID NO 31
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 31
tttgtggtcc agcagcggta                                              20
```

```
<210> SEQ ID NO 32
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 32
tgggcacatt ttctggcagc                                               20

<210> SEQ ID NO 33
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 33
ggagtaattc ccttctagct                                               20

<210> SEQ ID NO 34
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 34
tcccacagtt gctgcaagtt                                               20

<210> SEQ ID NO 35
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 35
atgttccagc tgttggagcc                                               20

<210> SEQ ID NO 36
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 36
ccaccatgtt ccagctgttg                                               20

<210> SEQ ID NO 37
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 37
gtccagggct tcagcccatg                                               20

<210> SEQ ID NO 38
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 38
```
gtgagggtca cagccttgac                                           20

<210> SEQ ID NO 39
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 39
ccatggtgag ggtcacagcc                                           20

<210> SEQ ID NO 40
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 40
ttggtgcgaa tgtacaagat                                           20

<210> SEQ ID NO 41
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 41
attttgtctt tggagcagta                                           20

<210> SEQ ID NO 42
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 42
aggaaattct caaagacttt                                           20

<210> SEQ ID NO 43
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 43
ctgcttcggc tggacatggt                                           20

<210> SEQ ID NO 44
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 44
tgttcctgct tcggctggac                                           20

<210> SEQ ID NO 45
<211> LENGTH: 20
<212> TYPE: DNA
<213> ORGANISM: Artificial Sequence

```
<220> FEATURE:
<223> OTHER INFORMATION: antisense oligonucleotide

<400> SEQUENCE: 45
ctgctctcaa agaaagggta                                              20

<210> SEQ ID NO 46
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 46
ccactctgct ctcaaagaaa                                              20

<210> SEQ ID NO 47
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 47
gttatccact ctgctctcaa                                              20

<210> SEQ ID NO 48
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 48
tccttgttat ccactctgct                                              20

<210> SEQ ID NO 49
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 49
ttgcagctgt ggatatcgat                                              20

<210> SEQ ID NO 50
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 50
cgtggttgca gctgtggata                                              20

<210> SEQ ID NO 51
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 51
agcctcgtgg ttgcagctgt                                              20
```

```
<210> SEQ ID NO 52
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 52
ttctcagcct cgtggttgca                                              20

<210> SEQ ID NO 53
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 53
ccagcttctc agcctcgtgg                                              20

<210> SEQ ID NO 54
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 54
gcagcccagc ttctcagcct                                              20

<210> SEQ ID NO 55
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 55
gcgctgcagc ccagcttctc                                              20

<210> SEQ ID NO 56
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 56
tttaaaaaga tggagttttc                                              20

<210> SEQ ID NO 57
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 57
gccactttaa aaagatggag                                              20

<210> SEQ ID NO 58
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 58
```

```
tcctgtctgg acacacattc                                              20

<210> SEQ ID NO 59
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 59
aagaacacag gatctgtcca                                              20

<210> SEQ ID NO 60
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 60
catagaagaa cacaggatct                                              20

<210> SEQ ID NO 61
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 61
ggaacgtaca catcagcagc                                              20

<210> SEQ ID NO 62
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 62
actccttcat agaccatccc                                              20

<210> SEQ ID NO 63
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 63
cggagataac ttttgagatc                                              20

<210> SEQ ID NO 64
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 64
gagaccggag ataacttttg                                              20

<210> SEQ ID NO 65
<211> LENGTH: 20
<212> TYPE: DNA
<213> ORGANISM: Artificial Sequence
```

```
<220> FEATURE:
<223> OTHER INFORMATION: antisense oligonucleotide

<400> SEQUENCE: 65
attttgactg tgaaatcttc                                               20

<210> SEQ ID NO 66
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 66
gcgatctccc agaggacgac                                               20

<210> SEQ ID NO 67
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 67
tgtagtagaa ggagacctcc                                               20

<210> SEQ ID NO 68
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 68
gccttgtgtc ctgagtgtct                                               20

<210> SEQ ID NO 69
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 69
atccaaggat cagcaggtcg                                               20

<210> SEQ ID NO 70
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 70
gctgcttgca tattgaaaaa                                               20

<210> SEQ ID NO 71
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 71
aaaaagctgc ttgcatattg                                               20
```

```
<210> SEQ ID NO 72
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 72
gcccatgtca gttaagggtt                                                 20

<210> SEQ ID NO 73
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 73
ccagcgtgtc tctcaaatgg                                                 20

<210> SEQ ID NO 74
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 74
ggagtttaaa ggacagtgcc                                                 20

<210> SEQ ID NO 75
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 75
catcactgac ctctttctat                                                 20

<210> SEQ ID NO 76
<211> LENGTH: 1433
<212> TYPE: DNA
<213> ORGANISM: Homo sapiens

<400> SEQUENCE: 76
attcggggcg agggaggagg aagaagcgga ggaggcggct cccgctcgca gggccgtgca     60
cctgcccgcc cgcccgctcg ctcgctcgcc cgccgcgccg cgctgccgac cgccagcatg    120
ctgccgagag tgggctgccc cgcgctgccg ctgccgccgc cgccgctgct gccgctgctg    180
ccgctgctgc tgctgctact gggcgcgagt ggcggcggcg gcggggcgcg cgcggaggtg    240
ctgttccgct gcccgcccctg cacacccgag cgcctggccg cctgcgggcc cccgccggtt    300
gcgccgcccg ccgcggtggc cgcagtggcc ggaggcgccc gcatgccatg cgcggagctc    360
gtccgggagc cgggctgcgg ctgctgctcg gtgtgcgccc ggctgaggg cgaggcgtgc    420 ggcgtctaca ccccgcgctg cggccagggg ctgcgctgct atccccaccc gggctccgag    480 ctgccctgc aggcgctggt catgggcgag ggcacttgtg agaagcgccg ggacgccgag    540
tatggcgcca gcccggagca ggttgcagac aatggcgatg accactcaga aggaggcctg    600
gtggagaacc acgtggacag caccatgaac atgttgggcg ggaggcag tgctggccgg    660 aagcccctca gtcgggtat gaaggagctg gccgtgttcc gggagaaggt cactgagcag    720
caccggcaga tgggcaaggg tggcaagcat caccttggcc tggaggagcc caagaagctg    780
```

```
cgaccacccc ctgccaggac tccctgccaa caggaactgg accaggtcct ggagcggatc      840
tccaccatgc gccttccgga tgagcggggc cctctggagc acctctactc cctgcacatc      900
cccaactgtg acaagcatgg cctgtacaac ctcaaacagt gcaagatgtc tctgaacggg      960
cagcgtgggg agtgctggtg tgtgaacccc aacaccggga agctgatcca gggagccccc     1020
accatccggg gggaccccga gtgtcatctc ttctacaatg agcagcagga ggcttgcggg     1080
gtgcacaccc agcggatgca gtagaccgca gccagccggt gcctggcgcc cctgccccc      1140 gccctctcc aaacaccggc agaaaacgga gagtgcttgg gtggtgggtg ctggaggatt      1200
ttccagttct gacacacgta tttatatttg aaagagacc agcaccgagc tcggcacctc      1260
cccggcctct ctcttcccag ctgcagatgc cacacctgct ccttcttgct ttccccgggg     1320
gaggaagggg gttgtggtcg gggagctggg gtacaggttt ggggaggggg aagagaaatt     1380 tttattttg aaccctgtg tccttttgc ataagattaa aggaaggaaa agt              1433
```

<210> SEQ ID NO 77
<211> LENGTH: 4989
<212> TYPE: DNA
<213> ORGANISM: Homo sapiens

<400> SEQUENCE: 77

```
ttttttttt ttttgagaaa gggaatttca tcccaaataa aaggaatgaa gtctggctcc       60
ggaggagggt ccccgacctc gctgtgggg ctcctgtttc tctccgccgc gctctcgctc      120
tggccgacga gtggagaaat ctgcgggcca ggcatcgaca tccgcaacga ctatcagcag     180
ctgaagcgcc tggagaactg cacggtgatc gagggctacc tccacatcct gctcatctcc     240
aaggccgagg actaccgcag ctaccgcttc cccaagctca cggtcattac cgagtacttg     300
ctgctgttcc gagtggctgg cctcgagagc ctcggagacc tcttccccaa cctcacggtc     360
atccgcggct ggaaactctt ctacaactac gccctggtca tcttcgagat gaccaatctc     420
aaggatattg ggctttacaa cctgaggaac attactcggg gggccatcag gattgagaaa     480
aatgctgacc tctgttacct ctccactgtg gactggtccc tgatcctgga tgcggtgtcc     540
aataactaca ttgtggggaa taagcccca aaggaatgtg gggacctgtg tccagggacc     600
atggaggaga gccgatgtg tgagaagacc accatcaaca atgagtacaa ctaccgctgc     660
tggaccacaa accgctgcca gaaaatgtgc ccaagcacgt gtgggaagcg ggcgtgcacc     720
gagaacaatg agtgctgcca ccccgagtgc ctgggcagct gcagcgcgcc tgacaacgac     780
acggcctgtg tagcttgccg ccactactac tatgccggtg tctgtgtgcc tgcctgcccg     840
cccaacacct acaggtttga gggctggcgc tgtgtggacc gtgacttctg cgccaacatc     900
ctcagcgccg agagcagcga ctccgagggg tttgtgatcc acgacggcga gtgcatgcag     960 gagtgccct cgggcttcat ccgcaacggc agccagagca tgtactgcat cccttgtgaa    1020
ggtccttgcc cgaaggtctg tgaggaagaa aagaaaacaa agaccattga ttctgttact    1080
tctgctcaga tgctccaagg atgcaccatc ttcaagggca atttgctcat taacatccga    1140
cgggggaata acattgcttc agagctggag aacttcatgg gctcatcga ggtggtgacg    1200 ggctacgtga agatccgcca ttctcatgcc ttggtctcct tgtccttcct aaaaaacctt    1260
cgcctcatcc taggagagga gcagctagaa gggaattact ccttctacgt cctcgacaac    1320
cagaacttgc agcaactgtg ggactgggac caccgcaacc tgaccatcaa agcagggaaa    1380 atgtacttg ctttcaatcc caattatgt gtttccgaaa tttaccgcat ggaggaagtg    1440
acggggacta aagggcgcca aagcaagg gacataaaca ccaggaacaa cggggagaga    1500
```

```
gcctcctgtg aaagtgacgt cctgcatttc acctccacca ccacgtcgaa gaatcgcatc    1560
atcataacct ggcaccggta ccggccccct gactacaggg atctcatcag cttcaccgtt    1620
tactacaagg aagcacccct taagaatgtc acagagtatg atgggcagga tgcctgcggc    1680
tccaacagct ggaacatggt ggacgtggac ctcccgccca acaaggacgt ggagcccggc    1740
atcttactac atgggctgaa gccctggact cagtacgccg tttacgtcaa ggctgtgacc    1800
ctcaccatgg tggagaacga ccatatccgt ggggccaaga gtgagatctt gtacattcgc    1860
accaatgctt cagttccttc cattcccttg gacgttcttt cagcatcgaa ctcctcttct    1920
cagttaatcg tgaagtggaa ccctccctct ctgcccaacg gcaacctgag ttactacatt    1980
gtgcgctggc agcggcagcc tcaggacggc tacctttacc ggcacaatta ctgctccaaa    2040
gacaaaatcc ccatcaggaa gtatgccgac ggcaccatcg acattgagga ggtcacagag    2100
aaccccaaga ctgaggtgtg tggtggggag aaagggcctt gctgcgcctg ccccaaaact    2160
gaagccgaga agcaggccga aaggaggag gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga cagagtac cctttctttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct tttaaagtg gccggaacct gagaatccca atggattgat tctaatgtat    2640
gaaataaaat acggatcaca agttgaggat cagcgagaat gtgtgtccag acaggaatac    2700
aggaagtatg gaggggccaa gctaaaccgg ctaaacccgg ggaactacac agcccggatt    2760
caggccacat ctctctctgg gaatgggtcg tggacagatc ctgtgttctt ctatgtccag    2820
gccaaaacag gatatgaaaa cttcatccat ctgatcatcg ctctgcccgt cgctgtcctg    2880
ttgatcgtgg gagggttggt gattatgctg tacgtcttcc atagaaagag aaataacagc    2940
aggctgggga atggagtgct gtatgcctct gtgaacccgg agtacttcag cgctgctgat    3000
gtgtacgttc ctgatgagtg ggaggtggct cgggagaaga tcaccatgag ccggaacctt    3060
gggcaggggt cgtttgggat ggtctatgaa ggagttgcca agggtgtggt gaaagatgaa    3120
cctgaaacca gagtggccat taaaacagtg aacgaggccg caagcatgcg tgagaggatt    3180
gagtttctca acgaagcttc tgtgatgaag gagttcaatt gtcaccatgt ggtgcgattg    3240
ctgggtgtgg tgtcccaagg ccagccaaca ctggtcatca tggaactgat gacacggggc    3300
gatctcaaaa gttatctccg gtctctgagg ccagaaatgg agaataatcc agtcctagca    3360
cctccaagcc tgagcaagat gattcagatg gccggagaga ttgcagacgg catggcatac    3420
ctcaacgcca ataagttcgt ccacagagac cttgctgccc ggaattgcat ggtagccgaa    3480
gatttcacag tcaaaatcgg agattttggt atgacgcgag atatctatga cagagactat    3540
taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccagggc ttgtccaacg agcaagtcct tcgcttcgtc    3720 atggaggcg gccttctgga caagccagac aactgtcctg acatgctgtt tgaactgatg    3780
cgcatgtgct ggcagtataa ccccaagatg aggccttcct tcctggagat catcagcagc    3840
atcaaagagg agatggagcc tggcttccgg gaggtctcct tctactacag cgaggagaac    3900
```

```
aagctgcccg agccggagga gctggacctg gagccagaga acatggagag cgtcccctg    3960 gaccctcgg cctcctcgtc ctccctgcca ctgcccgaca gacactcagg acacaaggcc    4020
gagaacggcc ccggccctgg ggtgctggtc ctccgcgcca gcttcgacga gagacagcct   4080
tacgcccaca tgaacggggg ccgcaagaac gagcgggcct tgccgctgcc ccagtcttcg   4140
acctgctgat ccttggatcc tgaatctgtg caaacagtaa cgtgtgcgca cgcgcagcgg   4200
ggtggggggg gagagagagt tttaacaatc cattcacaag cctcctgtac ctcagtggat   4260
cttcagttct gcccttgctg cccgcgggag acagcttctc tgcagtaaaa cacatttggg   4320
atgttccttt tttcaatatg caagcagctt tttattccct gcccaaaccc ttaactgaca   4380
tgggccttta agaaccttaa tgacaacact taatagcaac agagcacttg agaaccagtc   4440
tcctcactct gtccctgtcc ttccctgttc tccctttctc tctcctctct gcttcataac   4500
ggaaaaataa ttgccacaag tccagctggg aagccctttt tatcagtttg aggaagtggc   4560
tgtccctgtg gccccatcca accactgtac acacccgcct gacaccgtgg gtcattacaa   4620
aaaaacacgt ggagatggaa attttacct ttatctttca cctttctagg acatgaaat    4680 ttacaaaggg ccatcgttca tccaaggctg ttaccatttt aacgctgcct aattttgcca   4740
aaatcctgaa ctttctccct catcggcccg gcgctgattc ctcgtgtccg gaggcatggg   4800
tgagcatggc agctggttgc tccatttgag agacacgctg gcgacacact ccgtccatcc   4860
gactgcccct gctgtgctgc tcaaggccac aggcacacag gtctcattgc ttctgactag   4920
attattattt gggggaactg gacacaatag gtctttctct cagtgaaggt ggggagaagc   4980
tgaaccggc                                                           4989

<210> SEQ ID NO 78
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 78
cacaguugcu gcaag                                                      15

<210> SEQ ID NO 79
<211> LENGTH: 20
<212> TYPE: DNA
<213> ORGANISM: Artificial Sequence
<220> FEATURE:
<223> OTHER INFORMATION: antisense oligonucleotide control to human
      H-ras

<400> SEQUENCE: 79
tccgtcatcg ctcctcaggg                                                 20

<210> SEQ ID NO 80
<211> LENGTH: 20
<212> TYPE: DNA
<213> ORGANISM: Artificial Sequence
<220> FEATURE:
<223> OTHER INFORMATION: antisense oligonucleotide control to human JNK

<400> SEQUENCE: 80
gtgcgcgcga gcccgaaatc                                                 20

<210> SEQ ID NO 81
<211> LENGTH: 20
<212> TYPE: DNA
```

<213> ORGANISM: Artificial Sequence
<220> FEATURE:
<223> OTHER INFORMATION: antisense oligonucleotide control to mouse
      and rat c-raf

<400> SEQUENCE: 81
atgcattctg cccccaagga                                            20

<210> SEQ ID NO 82
<211> LENGTH: 21
<212> TYPE: DNA
<213> ORGANISM: Artificial Sequence
<220> FEATURE:
<223> OTHER INFORMATION: PCR primer to hIGF-RI

<400> SEQUENCE: 82
ccctttcttt gcagttttcc c                                          21

<210> SEQ ID NO 83
<211> LENGTH: 17
<212> TYPE: DNA
<213> ORGANISM: Artificial Sequence
<220> FEATURE:
<223> OTHER INFORMATION: PCR primer to hIGF-RI

<400> SEQUENCE: 83
cgtcgtcggc ctccatt                                               17

<210> SEQ ID NO 84
<211> LENGTH: 23
<212> TYPE: DNA
<213> ORGANISM: Artificial Sequence
<220> FEATURE:
<223> OTHER INFORMATION: PCR primer to hIGF-RI

<400> SEQUENCE: 84
ccttcctgcc tctccgggtt tga                                        23

<210> SEQ ID NO 85
<211> LENGTH: 20
<212> TYPE: DNA
<213> ORGANISM: Artificial Sequence
<220> FEATURE:
<223> OTHER INFORMATION: PCR primer to hIGF-RI

<400> SEQUENCE: 85
acatgggcgc gcgactaagt                                            20

<210> SEQ ID NO 86
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 86
atgcatacta cgaaaggccg                                            20

<210> SEQ ID NO 87
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 87
tattccacga acgtaggctg                                            20

<210> SEQ ID NO 88
<211> LENGTH: 15
<212> TYPE: RNA
<213> ORGANISM: Artificial Sequence
<220> FEATURE:
<223> OTHER INFORMATION: antisense oligonucleotide

<400> SEQUENCE: 88
uaacacgacg cgaau                                                      15

<210> SEQ ID NO 89
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 89
tccgtcatcg ctcctcaggg                                                 20

<210> SEQ ID NO 90
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 90
tccgtcatcg ctcctcaggg                                                 20

<210> SEQ ID NO 91
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 91
tcccgcctgt gacatgcatt                                                 20

<210> SEQ ID NO 92
<211> LENGTH: 21
<212> TYPE: DNA
<213> ORGANISM: Artificial Sequence
<220> FEATURE:
<223> OTHER INFORMATION: exemplified sense strand

<400> SEQUENCE: 92
cgagaggcgg acgggaccgt t                                               21

<210> SEQ ID NO 93
<211> LENGTH: 21
<212> TYPE: DNA
<213> ORGANISM: Artificial Sequence
<220> FEATURE:
<223> OTHER INFORMATION: exemplified antisense strand

<400> SEQUENCE: 93
ttgctctccg cctgccctgg c                                               21

<210> SEQ ID NO 94
<211> LENGTH: 19
<212> TYPE: DNA
<213> ORGANISM: Artificial Sequence
<220> FEATURE:
<223> OTHER INFORMATION: PCR probe to hGAPDH

<400> SEQUENCE: 94
gaaggtgaag gtcggagtc                                                19

<210> SEQ ID NO 95
<211> LENGTH: 20
<212> TYPE: DNA
<213> ORGANISM: Artificial Sequence
<220> FEATURE:
<223> OTHER INFORMATION: PCR probe to hGAPDH

<400> SEQUENCE: 95
gaagatggtg atgggatttc                                               20

<210> SEQ ID NO 96
<211> LENGTH: 20
<212> TYPE: DNA
<213> ORGANISM: Artificial Sequence
<220> FEATURE:
<223> OTHER INFORMATION: PCR probe to hGAPDH

<400> SEQUENCE: 96
caagcttccc gttctcagcc                                               20

<210> SEQ ID NO 97
<211> LENGTH: 5983
<212> TYPE: DNA
<213> ORGANISM: Homo sapiens

<400> SEQUENCE: 97
agtgtgtggc agcggcggcg gcggcgcggc gaggctgggg ctcttgttta ccagcattaa    60
ctcgctgagc ggaaaaaaaa agggaaaaaa cccgaggagg agcgagcgca ccaggcgaac   120
tcgagagagg cgggagagcg agagggacgc cgccagcgag cctgcccacg gccggcgctc   180
gcagaccctc ggccccgctc cccggatccc ccgcgccct ccacgcccct cccgcgcggg    240
ggcagctcca cggcgcgcct cgcctcggct gtgaccttca gcgagccgga gccccgcgc    300
agagcaggcg gcggcgggcg ggggccgggc ggggccggc gcggggcggg cggcggcgca    360
gagccgggcg gcgcggcggg agtgctgagc gcggcgcggc cggcccgccg ctttgtgtgt   420
gtcctggatt tgggaaggag ctccgccgcg cggcggcgct gagggaggag gcggcggcga   480
gcggagccag gaggaggagg aggaggaggg ggagccgctc attcattttg actccgcgtt   540
tctgcccctc gccggcctcg cctgtgaccc ggacttcggg gcgatcttgc gaactgcgtc   600
gcgccctccc gcggcggaag ctcgggcgtc cggccgcctc ccgcgcgcca gggccgggct   660
tgttttcct cgcctaggca gatttggget ttgccccctt tctttgcagt ttccccccct    720
tcctgcctct ccgggtttga aaatggaggc cgacgacgcc gacagcccgc cccggcgcgc   780
ctcgggttcc cgactccgcc gagccctggg ccgctgctgc cggcgctgag gggccgcccc   840
gcgccgcccg ccccgtccgc gcacccggag ggccccggcg gcggcccttc ggagtattgt   900
ttccttcgcc cttgttttg gagggggagc gaagactgag tttgagactt gtttcctttc    960
atttcctttt tttctttttct tttctttttt tttttttttt ttttttttga gaaagggaat  1020
ttcatcccaa ataaaaggaa tgaagtctgg ctccggagga gggtccccga cctcgctgtg  1080
ggggctcctg tttctctccg ccgcgctctc gctctggccg acgagtggag aaatctgcgg  1140
gccaggcatc gacatccgca acgactatca gcagctgaag cgcctggaga actgcacggt  1200
gatcgagggc tacctccaca tcctgctcat ctccaaggcc gaggactacc gcagctaccg  1260
cttccccaag ctcacggtca ttaccgagta cttgctgctg ttccgagtgg ctggcctcga  1320

```
gagcctcgga gacctcttcc ccaacctcac ggtcatccgc ggctggaaac tcttctacaa   1380
ctacgccctg gtcatcttcg agatgaccaa tctcaaggat attgggcttt acaacctgag   1440
gaacattact cgggggggcca tcaggattga gaaaaatgct gacctctgtt acctctccac   1500
tgtggactgg tccctgatcc tggatgcggt gtccaataac tacattgtgg ggaataagcc   1560
cccaaaggaa tgtggggacc tgtgtccagg gaccatggag gagaagccga tgtgtgagaa   1620
gaccaccatc aacaatgagt acaactaccg ctgctggacc acaaaccgct gccagaaaat   1680
gtgcccaagc acgtgtggga agcgggcgtg caccgagaac aatgagtgct gcaccccga    1740 gtgcctgggc agctgcagcg cgcctgacaa cgacacggcc tgtgtagctt gccgccacta   1800
ctactatgcc ggtgtctgtg tgcctgcctg cccgcccaac acctacaggt ttgagggctg   1860
gcgctgtgtg gaccgtgact tctgcgccaa catcctcagc gccgagagca gcgactccga   1920 ggggttgtg  atccacgacg gcgagtgcat gcaggagtgc ccctcgggct tcatccgcaa   1980
cggcagccag agcatgtact gcatcccttg tgaaggtcct tgcccgaagg tctgtgagga   2040
agaaaagaaa acaaagacca ttgattctgt tacttctgct cagatgctcc aaggatgcac   2100
catcttcaag gcaatttgc tcattaacat ccgacggggg aataacattg cttcagagct    2160
ggagaacttc atggggctca tcgaggtggt gacgggctac gtgaagatcc gccattctca   2220
tgccttggtc tccttgtcct tcctaaaaaa ccttcgcctc atcctaggag aggagcagct   2280
agaagggaat tactccttct acgtcctcga caaccagaac ttgcagcaac tgtgggactg   2340
ggaccaccgc aacctgacca tcaaagcagg gaaaatgtac tttgctttca atcccaaatt   2400
atgtgtttcc gaaatttacc gcatggagga agtgacgggg actaaagggc gccaaagcaa   2460 agggacata  aacaccagga acaacgggga gagagcctcc tgtgaaagtg acgtcctgca   2520
tttcacctcc accaccacgt cgaagaatcg catcatcata acctggcacc ggtaccggcc   2580
ccctgactac agggatctca tcagcttcac cgtttactac aaggaagcac cctttaagaa   2640
tgtcacagag tatgatgggc aggatgcctg cggctccaac agctggaaca tggtggacgt   2700
ggacctcccg cccaacaagg acgtggagcc cggcatctta ctacatgggc tgaagccctg   2760
gactcagtac gccgtttacg tcaaggctgt gaccctcacc atggtggaga cgaccatat   2820 ccgtgggcc aagagtgaga tcttgtacat tcgcaccaat gcttcagttc cttccattcc    2880
cttggacgtt ctttcagcat cgaactcctc ttctcagtta atcgtgaagt ggaaccctcc   2940
ctctctgccc aacggcaacc tgagttacta cattgtgcgc tggcagcggc agcctcagga   3000
cggctaccct taccggcaca attactgctc caaagacaaa atccccatca ggaagtatgc   3060
cgacggcacc atcgacattg aggaggtcac agagaacccc aagactgagg tgtgtggtgg   3120
ggagaaaggg ccttgctgcg cctgccccaa aactgaagcc gagaagcagg ccgagaagga   3180
ggaggctgaa taccgcaaag tctttgagaa tttcctgcac aactccatct tcgtgcccag   3240
acctgaaagg aagcggagag atgtcatgca agtggccaac accaccatgt ccagccgaag   3300
caggaacacc acggccgcag acacctacaa catcaccgac ccggaagagc tggagacaga   3360
gtaccctttc tttgagagca gagtggataa caaggagaga actgtcattt ctaaccttcg   3420
gcctttcaca ttgtaccgca tcgatatcca cagctgcaac cacgaggctg agaagctggg   3480
ctgcagcgcc tccaacttcg tctttgcaag gactatgccc gcagaaggag cagatgacat   3540
tcctgggcca gtgacctggg agccaaggcc tgaaaactcc atcttttaa  agtggccgga   3600 acctgagaat cccaatggat tgattctaat gtatgaaata aaatacggat cacaagttga   3660
ggatcagcga gaatgtgtgt ccagacagga atacaggaag tatggagggg ccaagctaaa   3720
```

```
ccggctaaac ccggggaact acacagcccg gattcaggcc acatctctct ctgggaatgg    3780
gtcgtggaca gatcctgtgt tcttctatgt ccaggccaaa acaggatatg aaaacttcat    3840
ccatctgatc atcgctctgc ccgtcgctgt cctgttgatc gtgggagggt tggtgattat    3900
gctgtacgtc ttccatagaa agagaaataa cagcaggctg gggaatggag tgctgtatgc    3960
ctctgtgaac ccggagtact tcagcgctgc tgatgtgtac gttcctgatg agtgggaggt    4020
ggctcgggag aagatcacca tgagccggga acttgggcag gggtcgtttg ggatggtcta    4080
tgaaggagtt gccaagggtg tggtgaaaga tgaacctgaa accagagtgg ccattaaaac    4140
agtgaacgag gccgcaagca tgcgtgagag gattgagttt ctcaacgaag cttctgtgat    4200
gaaggagttc aattgtcacc atgtggtgcg attgctgggt gtggtgtccc aaggccagcc    4260
aacactggtc atcatggaac tgatgacacg gggcgatctc aaaagttatc tccggtctct    4320
gaggccagaa atggagaata atccagtcct agcacctcca agcctgagca agatgattca    4380
gatggccgga gagattgcag acggcatggc atacctcaac gccaataagt tcgtccacag    4440
agaccttgct gcccggaatt gcatggtagc cgaagatttc acagtcaaaa tcggagattt    4500
tggtatgacg cgagatatct atgagacaga ctattaccgg aaaggaggca agggctgct    4560
gcccgtgcgc tggatgtctc ctgagtccct caaggatgga gtcttcacca cttactcgga    4620
cgtctggtcc ttcggggtcg tcctctggga gatcgccaca ctggccgagc agccctacca    4680
gggcttgtcc aacgagcaag tccttcgctt cgtcatggag ggcggccttc tggacaagcc    4740
agacaactgt cctgacatgc tgtttgaact gatgcgcatg tgctggcagt ataaccccaa    4800
gatgaggcct tccttcctgg agatcatcag cagcatcaaa gaggagatgg agcctggctt    4860
ccgggaggtc tccttctact acagcgagga gaacaagctg cccgagccgg aggagctgga    4920
cctggagcca gagaacatgg agagcgtccc cctggacccc tcggcctcct cgtcctccct    4980
gccactgccc gacagacact caggacacaa ggccgagaac ggccccggcc tggggtgct    5040
ggtcctccgc gccagcttcg acgagagaca gccttacgcc cacatgaacg ggggccgcaa    5100
gaacgagcgg gccttgccgc tgccccagtc ttcgacctgc tgatccttgg atcctgaatc    5160
tgtgcaaaca gtaacgtgtg cgcacgcgca gcggggtggg gggggagaga gagttttaac    5220
aatccattca caagcctcct gtacctcagt ggatcttcag ttctgccctt gctgcccgcg    5280
ggagacagct tctctgcagt aaaacacatt tgggatgttc cttttttcaa tatgcaagca    5340
gcttttatt ccctgcccaa acccttaact gacatgggcc tttaagaacc ttaatgacaa    5400
cacttaatag caacagagca cttgagaacc agtctcctca ctctgtccct gtccttccct    5460
gttctccctt tctctctcct ctctgcttca taacggaaaa ataattgcca caagtccagc    5520
tgggaagccc ttttatcag tttgaggaag tggctgtccc tgtggcccca tccaaccact    5580
gtacacaccc gcctgacacc gtgggtcatt acaaaaaaac acgtggagat ggaaattttt    5640
acctttatct ttcacctttc tagggacatg aaatttacaa agggccatcg ttcatccaag    5700
gctgttacca ttttaacgct gcctaatttt gccaaaatcc tgaactttct ccctcatcgg    5760
cccggcgctg attcctcgtg tccggaggca tgggtgagca tggcagctgg ttgctccatt    5820
tgagagacac gctggcgaca cactccgtcc atccgactgc ccctgctgtg ctgctcaagg    5880
ccacaggcac acaggtctca ttgcttctga ctagattatt atttggggga actggacaca    5940
ataggtcttt ctctcagtga aggtggggag aagctgaacc ggc                     5983
```

<210> SEQ ID NO 98
<211> LENGTH: 391

```
<212> TYPE: PRT
<213> ORGANISM: Homo sapiens

<400> SEQUENCE: 98

Asn Pro Glu Tyr Phe Ser Ala Ala Asp Val Tyr Val Pro Asp Glu Trp
1               5                   10                  15

Glu Val Ala Arg Glu Lys Ile Thr Met Ser Arg Glu Leu Gly Gln Gly
            20                  25                  30

Ser Phe Gly Met Val Tyr Glu Gly Val Ala Lys Gly Val Val Lys Asp
        35                  40                  45

Glu Pro Glu Thr Arg Val Ala Ile Lys Thr Val Asn Glu Ala Ala Ser
50                  55                  60

Met Arg Glu Arg Ile Glu Phe Leu Asn Glu Ala Ser Val Met Lys Glu
65                  70                  75                  80

Phe Asn Cys His His Val Val Arg Leu Leu Gly Val Val Ser Gln Gly
                85                  90                  95

Gln Pro Thr Leu Val Ile Met Glu Leu Met Thr Arg Gly Asp Leu Lys
            100                 105                 110

Ser Tyr Leu Arg Ser Leu Arg Pro Glu Met Glu Asn Asn Pro Val Leu
        115                 120                 125

Ala Pro Pro Ser Leu Ser Lys Met Ile Gln Met Ala Gly Glu Ile Ala
130                 135                 140

Asp Gly Met Ala Tyr Leu Asn Ala Asn Lys Phe Val His Arg Asp Leu
145                 150                 155                 160

Ala Ala Arg Asn Cys Met Val Ala Glu Asp Phe Thr Val Lys Ile Gly
                165                 170                 175

Asp Phe Gly Met Thr Arg Asp Ile Tyr Glu Thr Asp Tyr Tyr Arg Lys
            180                 185                 190

Gly Gly Lys Gly Leu Leu Pro Val Arg Trp Met Ser Pro Glu Ser Leu
        195                 200                 205

Lys Asp Gly Val Phe Thr Thr Tyr Ser Asp Val Trp Ser Phe Gly Val
210                 215                 220

Val Leu Trp Glu Ile Ala Thr Leu Ala Glu Gln Pro Tyr Gln Gly Leu
225                 230                 235                 240

Ser Asn Glu Gln Val Leu Arg Phe Val Met Glu Gly Gly Leu Leu Asp
                245                 250                 255

Lys Pro Asp Asn Cys Pro Asp Met Leu Phe Glu Leu Met Arg Met Cys
            260                 265                 270

Trp Gln Tyr Asn Pro Lys Met Arg Pro Ser Phe Leu Glu Ile Ile Ser
        275                 280                 285

Ser Ile Lys Glu Glu Met Glu Pro Gly Phe Arg Glu Val Ser Phe Tyr
290                 295                 300

Tyr Ser Glu Glu Asn Lys Leu Pro Glu Pro Glu Glu Leu Asp Leu Glu
305                 310                 315                 320

Pro Glu Asn Met Glu Ser Val Pro Leu Asp Pro Ser Ala Ser Ser Ser
                325                 330                 335

Ser Leu Pro Leu Pro Asp Arg His Ser Gly His Lys Ala Glu Asn Gly
            340                 345                 350

Pro Gly Pro Gly Val Leu Val Leu Arg Ala Ser Phe Asp Glu Arg Gln
        355                 360                 365

Pro Tyr Ala His Met Asn Gly Gly Arg Lys Asn Glu Arg Ala Leu Pro
370                 375                 380

Leu Pro Gln Ser Ser Thr Cys
385                 390
```

<210> SEQ ID NO 99
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: N = any base

<400> SEQUENCE: 99
nnnnnnnnnn nnnnnnnnnn                                           20

<210> SEQ ID NO 100
<211> LENGTH: 20
<212> TYPE: DNA
<213> ORGANISM: Homo sapiens

<400> SEQUENCE: 100
agtctcaaac tcagtcttcg                                           20

<210> SEQ ID NO 101
<211> LENGTH: 20
<212> TYPE: DNA
<213> ORGANISM: Homo sapiens

<400> SEQUENCE: 101
gttaatgctg gtaaacaaga                                           20

<210> SEQ ID NO 102
<211> LENGTH: 20
<212> TYPE: DNA
<213> ORGANISM: Homo sapiens

<400> SEQUENCE: 102
gaagtccggg tcacaggcga                                           20

<210> SEQ ID NO 103
<211> LENGTH: 20
<212> TYPE: DNA
<213> ORGANISM: Homo sapiens

<400> SEQUENCE: 103
aacaagagcc ccagcctcgc                                           20

<210> SEQ ID NO 104
<211> LENGTH: 20
<212> TYPE: DNA
<213> ORGANISM: Homo sapiens

<400> SEQUENCE: 104
atgctggtaa acaagagccc                                           20

<210> SEQ ID NO 105
<211> LENGTH: 20
<212> TYPE: DNA
<213> ORGANISM: Homo sapiens

<400> SEQUENCE: 105
tgctggtaaa caagagcccc                                           20

<210> SEQ ID NO 106
<211> LENGTH: 20
<212> TYPE: DNA
<213> ORGANISM: Homo sapiens

```
<400> SEQUENCE: 106
ggagtcaaaa tgaatgagcg                                            20

<210> SEQ ID NO 107
<211> LENGTH: 20
<212> TYPE: DNA
<213> ORGANISM: Homo sapiens

<400> SEQUENCE: 107
aatctgccta ggcgaggaaa                                            20

<210> SEQ ID NO 108
<211> LENGTH: 20
<212> TYPE: DNA
<213> ORGANISM: Homo sapiens

<400> SEQUENCE: 108
gctggtaaac aagagcccca                                            20

<210> SEQ ID NO 109
<211> LENGTH: 20
<212> TYPE: DNA
<213> ORGANISM: Homo sapiens

<400> SEQUENCE: 109
agcccaaatc tgcctaggcg                                            20

<210> SEQ ID NO 110
<211> LENGTH: 20
<212> TYPE: DNA
<213> ORGANISM: Homo sapiens

<400> SEQUENCE: 110
cctccatttt caaacccgga                                            20

<210> SEQ ID NO 111
<211> LENGTH: 20
<212> TYPE: DNA
<213> ORGANISM: Homo sapiens

<400> SEQUENCE: 111
gaaggtcaca gccgaggcga                                            20

<210> SEQ ID NO 112
<211> LENGTH: 20
<212> TYPE: DNA
<213> ORGANISM: Homo sapiens

<400> SEQUENCE: 112
tcgctgaagg tcacagccga                                            20

<210> SEQ ID NO 113
<211> LENGTH: 20
<212> TYPE: DNA
<213> ORGANISM: Homo sapiens

<400> SEQUENCE: 113
atccaggaca cacacaaagc                                            20

<210> SEQ ID NO 114
<211> LENGTH: 20
<212> TYPE: DNA
<213> ORGANISM: Homo sapiens
```

```
<400> SEQUENCE: 114
aagtccgggt cacaggcgag                                          20

<210> SEQ ID NO 115
<211> LENGTH: 20
<212> TYPE: DNA
<213> ORGANISM: Homo sapiens

<400> SEQUENCE: 115
aagtctcaaa ctcagtcttc                                          20

<210> SEQ ID NO 116
<211> LENGTH: 20
<212> TYPE: DNA
<213> ORGANISM: Homo sapiens

<400> SEQUENCE: 116
gtcgtcggcc tccattttca                                          20

<210> SEQ ID NO 117
<211> LENGTH: 20
<212> TYPE: DNA
<213> ORGANISM: Homo sapiens

<400> SEQUENCE: 117
gcagaaacgc ggagtcaaaa                                          20

<210> SEQ ID NO 118
<211> LENGTH: 20
<212> TYPE: DNA
<213> ORGANISM: Homo sapiens

<400> SEQUENCE: 118
gcggcgagct ccttcccaaa                                          20

<210> SEQ ID NO 119
<211> LENGTH: 20
<212> TYPE: DNA
<213> ORGANISM: Homo sapiens

<400> SEQUENCE: 119
taatgctggt aaacaagagc                                          20

<210> SEQ ID NO 120
<211> LENGTH: 20
<212> TYPE: DNA
<213> ORGANISM: Homo sapiens

<400> SEQUENCE: 120
tttcaaaccc ggagaggcag                                          20

<210> SEQ ID NO 121
<211> LENGTH: 20
<212> TYPE: DNA
<213> ORGANISM: Homo sapiens

<400> SEQUENCE: 121
taggcgagga aaacaagcc                                           20

<210> SEQ ID NO 122
<211> LENGTH: 20
<212> TYPE: DNA
<213> ORGANISM: Homo sapiens
```

```
<400> SEQUENCE: 122
ctcgctgaag gtcacagccg                                                    20

<210> SEQ ID NO 123
<211> LENGTH: 20
<212> TYPE: DNA
<213> ORGANISM: Homo sapiens

<400> SEQUENCE: 123
gcagcggccc agggctcggc                                                    20

<210> SEQ ID NO 124
<211> LENGTH: 20
<212> TYPE: DNA
<213> ORGANISM: Homo sapiens

<400> SEQUENCE: 124
gctcgctgaa ggtcacagcc                                                    20

<210> SEQ ID NO 125
<211> LENGTH: 20
<212> TYPE: DNA
<213> ORGANISM: Homo sapiens

<400> SEQUENCE: 125
cgaaggaaac aatactccga                                                    20

<210> SEQ ID NO 126
<211> LENGTH: 20
<212> TYPE: DNA
<213> ORGANISM: Homo sapiens

<400> SEQUENCE: 126
gaaacgcgga gtcaaaatga                                                    20

<210> SEQ ID NO 127
<211> LENGTH: 20
<212> TYPE: DNA
<213> ORGANISM: Homo sapiens

<400> SEQUENCE: 127
gaaacaatac tccgaagggc                                                    20

<210> SEQ ID NO 128
<211> LENGTH: 20
<212> TYPE: DNA
<213> ORGANISM: Homo sapiens

<400> SEQUENCE: 128
ccaaatccag gacacacaca                                                    20

<210> SEQ ID NO 129
<211> LENGTH: 20
<212> TYPE: DNA
<213> ORGANISM: Homo sapiens

<400> SEQUENCE: 129
tcggcctcca ttttcaaacc                                                    20

<210> SEQ ID NO 130
<211> LENGTH: 20
<212> TYPE: DNA
<213> ORGANISM: Homo sapiens
```

```
<400> SEQUENCE: 130
tccgggtcac aggcgaggcc                                              20

<210> SEQ ID NO 131
<211> LENGTH: 20
<212> TYPE: DNA
<213> ORGANISM: Homo sapiens

<400> SEQUENCE: 131
aatgaatgag cggctccccc                                              20

<210> SEQ ID NO 132
<211> LENGTH: 20
<212> TYPE: DNA
<213> ORGANISM: Homo sapiens

<400> SEQUENCE: 132
tgaaggtcac agccgaggcg                                              20

<210> SEQ ID NO 133
<211> LENGTH: 20
<212> TYPE: DNA
<213> ORGANISM: Homo sapiens

<400> SEQUENCE: 133
aaggtcacag ccgaggcgag                                              20

<210> SEQ ID NO 134
<211> LENGTH: 20
<212> TYPE: DNA
<213> ORGANISM: Homo sapiens

<400> SEQUENCE: 134
cccaaatcca ggacacacac                                              20

<210> SEQ ID NO 135
<211> LENGTH: 20
<212> TYPE: DNA
<213> ORGANISM: Homo sapiens

<400> SEQUENCE: 135
acaagtctca aactcagtct                                              20

<210> SEQ ID NO 136
<211> LENGTH: 20
<212> TYPE: DNA
<213> ORGANISM: Homo sapiens

<400> SEQUENCE: 136
ggtaaacaag agccccagcc                                              20

<210> SEQ ID NO 137
<211> LENGTH: 20
<212> TYPE: DNA
<213> ORGANISM: Homo sapiens

<400> SEQUENCE: 137
cgaagactga gtttgagact                                              20

<210> SEQ ID NO 138
<211> LENGTH: 20
<212> TYPE: DNA
<213> ORGANISM: Homo sapiens
```

```
<400> SEQUENCE: 138
tcgcctgtga cccggacttc                                               20

<210> SEQ ID NO 139
<211> LENGTH: 20
<212> TYPE: DNA
<213> ORGANISM: Homo sapiens

<400> SEQUENCE: 139
gcgaggctgg ggctcttgtt                                               20

<210> SEQ ID NO 140
<211> LENGTH: 20
<212> TYPE: DNA
<213> ORGANISM: Homo sapiens

<400> SEQUENCE: 140
gggctcttgt ttaccagcat                                               20

<210> SEQ ID NO 141
<211> LENGTH: 20
<212> TYPE: DNA
<213> ORGANISM: Homo sapiens

<400> SEQUENCE: 141
ggggctcttg tttaccagca                                               20

<210> SEQ ID NO 142
<211> LENGTH: 20
<212> TYPE: DNA
<213> ORGANISM: Homo sapiens

<400> SEQUENCE: 142
cgctcattca ttttgactcc                                               20

<210> SEQ ID NO 143
<211> LENGTH: 20
<212> TYPE: DNA
<213> ORGANISM: Homo sapiens

<400> SEQUENCE: 143
tttcctcgcc taggcagatt                                               20

<210> SEQ ID NO 144
<211> LENGTH: 20
<212> TYPE: DNA
<213> ORGANISM: Homo sapiens

<400> SEQUENCE: 144
tggggctctt gtttaccagc                                               20

<210> SEQ ID NO 145
<211> LENGTH: 20
<212> TYPE: DNA
<213> ORGANISM: Homo sapiens

<400> SEQUENCE: 145
cgcctaggca gatttgggct                                               20

<210> SEQ ID NO 146
<211> LENGTH: 20
<212> TYPE: DNA
<213> ORGANISM: Homo sapiens
```

<400> SEQUENCE: 146
tccgggtttg aaaatggagg                                                         20

<210> SEQ ID NO 147
<211> LENGTH: 20
<212> TYPE: DNA
<213> ORGANISM: Homo sapiens

<400> SEQUENCE: 147
tcgcctcggc tgtgaccttc                                                         20

<210> SEQ ID NO 148
<211> LENGTH: 20
<212> TYPE: DNA
<213> ORGANISM: Homo sapiens

<400> SEQUENCE: 148
tcggctgtga ccttcagcga                                                         20

<210> SEQ ID NO 149
<211> LENGTH: 20
<212> TYPE: DNA
<213> ORGANISM: Homo sapiens

<400> SEQUENCE: 149
gctttgtgtg tgtcctggat                                                         20

<210> SEQ ID NO 150
<211> LENGTH: 20
<212> TYPE: DNA
<213> ORGANISM: Homo sapiens

<400> SEQUENCE: 150
ctcgcctgtg acccggactt                                                         20

<210> SEQ ID NO 151
<211> LENGTH: 20
<212> TYPE: DNA
<213> ORGANISM: Homo sapiens

<400> SEQUENCE: 151
gaagactgag tttgagactt                                                         20

<210> SEQ ID NO 152
<211> LENGTH: 20
<212> TYPE: DNA
<213> ORGANISM: Homo sapiens

<400> SEQUENCE: 152
tgaaaatgga ggccgacgac                                                         20

<210> SEQ ID NO 153
<211> LENGTH: 20
<212> TYPE: DNA
<213> ORGANISM: Homo sapiens

<400> SEQUENCE: 153
ttttgactcc gcgtttctgc                                                         20

<210> SEQ ID NO 154
<211> LENGTH: 20
<212> TYPE: DNA
<213> ORGANISM: Homo sapiens

```
<400> SEQUENCE: 154
tttgggaagg agctcgccgc                                          20

<210> SEQ ID NO 155
<211> LENGTH: 20
<212> TYPE: DNA
<213> ORGANISM: Homo sapiens

<400> SEQUENCE: 155
gctcttgttt accagcatta                                          20

<210> SEQ ID NO 156
<211> LENGTH: 20
<212> TYPE: DNA
<213> ORGANISM: Homo sapiens

<400> SEQUENCE: 156
ggcttgtttt tcctcgccta                                          20

<210> SEQ ID NO 157
<211> LENGTH: 20
<212> TYPE: DNA
<213> ORGANISM: Homo sapiens

<400> SEQUENCE: 157
cggctgtgac cttcagcgag                                          20

<210> SEQ ID NO 158
<211> LENGTH: 20
<212> TYPE: DNA
<213> ORGANISM: Homo sapiens

<400> SEQUENCE: 158
gccgagccct gggccgctgc                                          20

<210> SEQ ID NO 159
<211> LENGTH: 20
<212> TYPE: DNA
<213> ORGANISM: Homo sapiens

<400> SEQUENCE: 159
ggctgtgacc ttcagcgagc                                          20

<210> SEQ ID NO 160
<211> LENGTH: 20
<212> TYPE: DNA
<213> ORGANISM: Homo sapiens

<400> SEQUENCE: 160
tcggagtatt gtttccttcg                                          20

<210> SEQ ID NO 161
<211> LENGTH: 20
<212> TYPE: DNA
<213> ORGANISM: Homo sapiens

<400> SEQUENCE: 161
tcattttgac tccgcgtttc                                          20

<210> SEQ ID NO 162
<211> LENGTH: 20
<212> TYPE: DNA
<213> ORGANISM: Homo sapiens
```

```
<400> SEQUENCE: 162
gcccttcgga gtattgtttc                                            20

<210> SEQ ID NO 163
<211> LENGTH: 20
<212> TYPE: DNA
<213> ORGANISM: Homo sapiens

<400> SEQUENCE: 163
tgtgtgtgtc ctggatttgg                                            20

<210> SEQ ID NO 164
<211> LENGTH: 20
<212> TYPE: DNA
<213> ORGANISM: Homo sapiens

<400> SEQUENCE: 164
ggtttgaaaa tggaggccga                                            20

<210> SEQ ID NO 165
<211> LENGTH: 20
<212> TYPE: DNA
<213> ORGANISM: Homo sapiens

<400> SEQUENCE: 165
ggcctcgcct gtgacccgga                                            20

<210> SEQ ID NO 166
<211> LENGTH: 20
<212> TYPE: DNA
<213> ORGANISM: Homo sapiens

<400> SEQUENCE: 166
gggggagccg ctcattcatt                                            20

<210> SEQ ID NO 167
<211> LENGTH: 20
<212> TYPE: DNA
<213> ORGANISM: Homo sapiens

<400> SEQUENCE: 167
cgcctcggct gtgaccttca                                            20

<210> SEQ ID NO 168
<211> LENGTH: 20
<212> TYPE: DNA
<213> ORGANISM: Homo sapiens

<400> SEQUENCE: 168
ctcgcctcgg ctgtgacctt                                            20

<210> SEQ ID NO 169
<211> LENGTH: 20
<212> TYPE: DNA
<213> ORGANISM: Homo sapiens

<400> SEQUENCE: 169
gtgtgtgtcc tggatttggg                                            20

<210> SEQ ID NO 170
<211> LENGTH: 20
<212> TYPE: DNA
<213> ORGANISM: Homo sapiens
```

```
<400> SEQUENCE: 170
agactgagtt tgagacttgt                                               20

<210> SEQ ID NO 171
<211> LENGTH: 20
<212> TYPE: DNA
<213> ORGANISM: Homo sapiens

<400> SEQUENCE: 171
ggctggggct cttgtttacc                                               20
```